US010349908B2

(12) United States Patent
Yun et al.

(10) Patent No.: US 10,349,908 B2
(45) Date of Patent: Jul. 16, 2019

(54) X-RAY INTERFEROMETRIC IMAGING SYSTEM

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US); Alan Francis Lyon, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 674 days.

(21) Appl. No.: 14/943,445

(22) Filed: Nov. 17, 2015

(65) Prior Publication Data

US 2016/0066870 A1    Mar. 10, 2016

Related U.S. Application Data

(63) Continuation of application No. 14/527,523, filed on Oct. 29, 2014, now abandoned.
(Continued)

(51) Int. Cl.
*A61B 6/00*      (2006.01)
*A61B 6/03*      (2006.01)
(Continued)

(52) U.S. Cl.
CPC .............. *A61B 6/484* (2013.01); *A61B 6/032* (2013.01); *A61B 6/035* (2013.01); *A61B 6/4007* (2013.01);
(Continued)

(58) Field of Classification Search
CPC ..... A61B 6/032; A61B 6/4035; A61B 6/4291; A61B 6/484; A61B 6/035; H01J 35/08; H01J 35/12
(Continued)

(56) References Cited

U.S. PATENT DOCUMENTS 1,203,495 A    10/1916    Coolidge
1,211,092 A    1/1917     Coolidge
(Continued)

FOREIGN PATENT DOCUMENTS

CN    102124537 A    7/2011
EP    0432568        6/1991
(Continued)

OTHER PUBLICATIONS

Takayoshi Shimura et al., "Hard x-ray phase contrast imaging using a tabletop Talbot-Lau interferometer with multiline embedded x-ray targets," Optics Letters vol. 38, No. 2, Jan. 15, 2013.*
(Continued)

*Primary Examiner* — Allen C. Ho
(74) *Attorney, Agent, or Firm* — Knobbe, Martens, Olson & Bear, LLP

(57) ABSTRACT

An x-ray interferometric imaging system includes an x-ray source with a target having a plurality of discrete structures arranged in a periodic pattern. The system further includes a beam-splitting x-ray grating, a stage configured to hold an object to be imaged, and an x-ray detector having a two-dimensional array of x-ray detecting elements. The object is positioned between the beam-splitting x-ray grating and the x-ray detector, the x-ray detector is positioned to detect the x-rays diffracted by the beam-splitting x-ray grating and perturbed by the object to be imaged.

22 Claims, 33 Drawing Sheets

Related U.S. Application Data

(60) Provisional application No. 61/898,019, filed on Oct. 31, 2013, provisional application No. 61/901,361, filed on Nov. 7, 2013, provisional application No. 61/981,098, filed on Apr. 17, 2014.

(51) Int. Cl.
  H01J 35/08 (2006.01)
  H01J 35/12 (2006.01)

(52) U.S. Cl.
  CPC .......... *A61B 6/4035* (2013.01); *A61B 6/4291* (2013.01); *A61B 6/502* (2013.01); *A61B 6/508* (2013.01); *H01J 35/08* (2013.01); *H01J 35/12* (2013.01); *G21K 2207/005* (2013.01)

(58) Field of Classification Search
  USPC ............................... 378/36, 37, 62, 130, 143
  See application file for complete search history.

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,266,138 A | 5/1981 | Nelson et al. |
| 4,277,112 A | 7/1981 | Heshmat |
| 4,426,718 A | 1/1984 | Hayashi et al. |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,768,339 A | 6/1998 | O'Hara |
| 5,772,903 A | 6/1998 | Hirsch |
| 5,778,039 A | 7/1998 | Hossain |
| 5,812,629 A * | 9/1998 | Clauser .................. A61B 6/032 378/37 |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 * | 10/2002 | Korenev .................. G21K 5/10 378/119 |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 * | 2/2007 | Momose .................. A61B 6/06 378/62 |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,349,525 B2 * | 3/2008 | Morton .................. H01J 35/08 378/124 |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 * | 6/2008 | Hebert .................. H01J 35/101 378/143 |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 * | 10/2008 | Baumann ............... A61B 6/032 378/145 |
| 7,440,542 B2 * | 10/2008 | Baumann ............... A61B 6/484 378/44 |
| 7,443,953 B1 | 10/2008 | Yun et al. |
| 7,453,981 B2 * | 11/2008 | Baumann ............... A61B 6/484 378/21 |
| 7,463,712 B2 | 12/2008 | Zhu et al. |
| 7,486,770 B2 * | 2/2009 | Baumann ............... A61B 6/032 378/145 |
| 7,492,871 B2 * | 2/2009 | Popescu .................. A61B 6/00 378/145 |

(56) References Cited

U.S. PATENT DOCUMENTS

| | | | |
|---|---|---|---|
| 7,499,521 B2 | 3/2009 | Wang et al. | |
| 7,515,684 B2 | 4/2009 | Gibson et al. | |
| 7,522,698 B2* | 4/2009 | Popescu | A61B 6/032 378/19 |
| 7,522,707 B2 | 4/2009 | Steinlage et al. | |
| 7,522,708 B2* | 4/2009 | Heismann | A61B 6/00 378/145 |
| 7,529,343 B2 | 5/2009 | Safai et al. | |
| 7,532,704 B2* | 5/2009 | Hempel | A61B 6/032 378/145 |
| 7,551,719 B2 | 6/2009 | Yokhin et al. | |
| 7,551,722 B2 | 6/2009 | Ohshima et al. | |
| 7,561,662 B2 | 7/2009 | Wang et al. | |
| 7,564,941 B2* | 7/2009 | Baumann | A61B 6/484 378/146 |
| 7,583,789 B1 | 9/2009 | Macdonald et al. | |
| 7,601,399 B2 | 10/2009 | Barnola et al. | |
| 7,639,786 B2* | 12/2009 | Baumann | A61B 6/484 378/145 |
| 7,646,843 B2* | 1/2010 | Popescu | A61B 6/032 356/521 |
| 7,672,433 B2 | 3/2010 | Zhong et al. | |
| 7,680,243 B2 | 3/2010 | Yokhin et al. | |
| 7,787,588 B1 | 8/2010 | Yun et al. | |
| 7,796,725 B1 | 9/2010 | Yun et al. | |
| 7,796,726 B1 | 9/2010 | Gendreau et al. | |
| 7,800,072 B2 | 9/2010 | Yun et al. | |
| 7,809,113 B2* | 10/2010 | Aoki | G01N 23/223 378/124 |
| 7,813,475 B1 | 10/2010 | Wu et al. | |
| 7,817,777 B2* | 10/2010 | Baumann | A61B 6/00 378/36 |
| 7,864,426 B2 | 1/2011 | Yun et al. | |
| 7,864,922 B2 | 1/2011 | Kawabe | |
| 7,873,146 B2 | 1/2011 | Okunuki et al. | |
| 7,876,883 B2 | 1/2011 | O'Hara | |
| 7,889,838 B2* | 2/2011 | David | A61B 6/4233 378/36 |
| 7,889,844 B2 | 2/2011 | Okunuki et al. | |
| 7,914,693 B2 | 3/2011 | Jeong et al. | |
| 7,920,673 B2 | 4/2011 | Lanza et al. | |
| 7,920,676 B2 | 4/2011 | Yun et al. | |
| 7,924,973 B2* | 4/2011 | Kottler | G01B 15/025 378/36 |
| 7,929,667 B1 | 4/2011 | Zhuang et al. | |
| 7,945,018 B2* | 5/2011 | Heismann | A61B 6/032 378/145 |
| 7,949,092 B2 | 5/2011 | Brons et al. | |
| 7,949,095 B2* | 5/2011 | Ning | A61B 6/032 378/4 |
| 7,974,379 B1 | 7/2011 | Case et al. | |
| 7,983,381 B2* | 7/2011 | David | A61B 6/032 378/4 |
| 7,991,120 B2 | 8/2011 | Okunuki et al. | |
| 8,005,185 B2* | 8/2011 | Popescu | A61B 6/06 378/19 |
| 8,009,796 B2* | 8/2011 | Popescu | A61B 6/032 378/19 |
| 8,009,797 B2* | 8/2011 | Ouchi | G01N 23/04 378/36 |
| 8,041,004 B2* | 10/2011 | David | A61B 6/484 378/36 |
| 8,036,341 B2 | 11/2011 | Lee | |
| 8,058,621 B2 | 11/2011 | Kommareddy et al. | |
| 8,068,579 B1 | 11/2011 | Yun et al. | |
| 8,073,099 B2* | 12/2011 | Niu | A61B 6/00 378/36 |
| 8,094,784 B2 | 1/2012 | Morton | |
| 8,139,711 B2* | 3/2012 | Takahashi | A61B 6/00 356/457 |
| 8,139,716 B2 | 3/2012 | Okunuki et al. | |
| 8,184,771 B2* | 5/2012 | Murakoshi | A61B 6/484 378/145 |
| 8,208,602 B2 | 6/2012 | Lee et al. | |
| 8,208,603 B2 | 6/2012 | Sato | |
| 8,233,587 B2* | 7/2012 | Sato | G21K 1/06 378/36 |
| 8,243,879 B2 | 8/2012 | Itoh et al. | |
| 8,243,884 B2 | 8/2012 | Rödhammer et al. | |
| 8,280,000 B2* | 10/2012 | Takahashi | A61B 6/484 378/62 |
| 8,306,183 B2* | 11/2012 | Koehler | A61B 6/00 378/36 |
| 8,306,184 B2 | 11/2012 | Chang et al. | |
| 8,351,569 B2* | 1/2013 | Baker | G01N 23/04 378/62 |
| 8,351,570 B2* | 1/2013 | Nakamura | G21K 1/06 378/145 |
| 8,353,628 B1 | 1/2013 | Yun et al. | |
| 8,360,640 B2 | 1/2013 | Reinhold | |
| 8,374,309 B2* | 2/2013 | Donath | A61B 6/032 378/145 |
| 8,406,378 B2 | 3/2013 | Wang et al. | |
| 8,416,920 B2 | 4/2013 | Okumura et al. | |
| 8,422,633 B2 | 4/2013 | Lantz et al. | |
| 8,451,975 B2* | 5/2013 | Tada | A61B 6/4291 378/207 |
| 8,422,637 B2 | 6/2013 | Okunuki et al. | |
| 8,509,386 B2 | 8/2013 | Lee et al. | |
| 8,520,803 B2 | 8/2013 | Behling | |
| 8,526,575 B1 | 9/2013 | Yun et al. | |
| 8,532,257 B2 | 9/2013 | Mukaide et al. | |
| 8,553,843 B2 | 10/2013 | Drory | |
| 8,559,594 B2* | 10/2013 | Ouchi | G01N 23/04 378/36 |
| 8,559,597 B2 | 10/2013 | Chen et al. | |
| 8,565,371 B2* | 10/2013 | Bredno | A61B 6/032 378/9 |
| 8,576,983 B2* | 11/2013 | Baeumer | G21K 1/06 378/145 |
| 8,591,108 B2* | 11/2013 | Tada | A61B 6/00 378/207 |
| 8,602,648 B1 | 12/2013 | Jacobsen et al. | |
| 8,632,247 B2* | 1/2014 | Ishii | A61B 6/00 378/207 |
| 8,666,024 B2 | 3/2014 | Okunuki et al. | |
| 8,666,025 B2 | 3/2014 | Klausz | |
| 8,699,667 B2 | 4/2014 | Steinlage et al. | |
| 8,735,844 B1 | 5/2014 | Khaykovich et al. | |
| 8,737,565 B1 | 5/2014 | Lyon et al. | |
| 8,744,048 B2 | 6/2014 | Lee et al. | |
| 8,755,487 B2* | 6/2014 | Kaneko | A61B 6/06 378/36 |
| 8,767,915 B2* | 7/2014 | Stutman | G01N 23/04 378/62 |
| 8,767,916 B2* | 7/2014 | Hashimoto | A61B 6/484 378/62 |
| 8,781,069 B2* | 7/2014 | Murakoshi | A61B 6/4233 378/36 |
| 8,824,629 B2* | 9/2014 | Ishii | G01N 23/04 378/62 |
| 8,831,174 B2* | 9/2014 | Kohara | A61B 6/06 378/62 |
| 8,831,175 B2 | 9/2014 | Silver et al. | |
| 8,831,179 B2 | 9/2014 | Adler et al. | |
| 8,855,265 B2* | 10/2014 | Engel | A61B 6/00 378/36 |
| 8,861,682 B2 | 10/2014 | Okunuki et al. | |
| 8,903,042 B2* | 12/2014 | Ishii | A61B 6/4233 378/207 |
| 8,908,824 B2* | 12/2014 | Kondoh | G01D 5/38 359/11 |
| 8,995,622 B2 | 3/2015 | Adler et al. | |
| 9,001,967 B2* | 4/2015 | Baturin | A61B 6/484 378/156 |
| 9,008,278 B2 | 4/2015 | Lee et al. | |
| 9,016,943 B2 | 4/2015 | Jacobsen et al. | |
| 9,020,101 B2 | 4/2015 | Omote et al. | |
| 9,063,055 B2* | 6/2015 | Ouchi | G01N 23/04 |
| 9,129,715 B2 | 9/2015 | Adler et al. | |

(56) References Cited

U.S. PATENT DOCUMENTS

| | | | |
|---|---|---|---|
| 9,222,899 B2* | 12/2015 | Yamaguchi | G02B 5/1842 |
| 9,257,254 B2* | 2/2016 | Ogura | H01J 35/08 |
| 9,263,225 B2* | 2/2016 | Morton | H01J 35/08 |
| 9,329,141 B2* | 5/2016 | Stutman | G01N 23/046 |
| 9,357,975 B2* | 6/2016 | Baturin | G01N 23/20075 |
| 9,390,881 B2* | 7/2016 | Yun | G21K 1/06 |
| 9,439,613 B2* | 9/2016 | Stutman | G01N 23/046 |
| 9,448,190 B2 | 9/2016 | Yun et al. | |
| 9,449,781 B2 | 9/2016 | Yun et al. | |
| 9,494,534 B2* | 11/2016 | Baturin | G01N 23/20075 |
| 9,543,109 B2* | 1/2017 | Yun | H01J 35/106 |
| 9,564,284 B2* | 2/2017 | Gerzoskovitz | H01J 35/12 |
| 9,570,265 B1 | 2/2017 | Yun et al. | |
| 9,594,036 B2* | 3/2017 | Yun | G01N 23/223 |
| 9,632,040 B2* | 4/2017 | Stutman | G01N 23/20075 |
| 9,719,947 B2* | 8/2017 | Yun | G01N 23/20075 |
| 9,757,081 B2* | 9/2017 | Proksa | A61B 6/032 |
| 9,761,021 B2* | 9/2017 | Koehler | G06T 11/006 |
| 9,823,203 B2* | 11/2017 | Yun | H01J 35/08 |
| 9,826,949 B2* | 11/2017 | Ning | A61B 6/032 |
| 9,837,178 B2* | 12/2017 | Nagai | G06T 5/20 |
| 9,842,414 B2* | 12/2017 | Koehler | A61B 6/484 |
| 9,861,330 B2* | 1/2018 | Rössl | A61B 6/484 |
| 9,874,531 B2* | 1/2018 | Yun | G01N 23/20075 |
| 9,881,710 B2* | 1/2018 | Roessl | G21K 1/06 |
| 9,916,655 B2* | 3/2018 | Stampanoni | A61B 6/483 |
| 9,939,392 B2* | 4/2018 | Wen | G01N 23/04 |
| 9,970,119 B2* | 5/2018 | Yokoyama | A61B 6/00 |
| 10,014,148 B2* | 7/2018 | Tang | H01J 35/065 |
| 10,028,716 B2* | 7/2018 | Rössl | A61B 6/484 |
| 10,045,753 B2* | 8/2018 | Teshima | C25D 5/02 |
| 10,068,740 B2* | 9/2018 | Gupta | A61B 6/40 |
| 10,074,451 B2* | 9/2018 | Kottler | A61B 6/484 |
| 10,076,297 B2* | 9/2018 | Bauer | A61B 6/032 |
| 10,085,701 B2* | 10/2018 | Hoshino | A61B 6/04 |
| 10,141,081 B2* | 11/2018 | Preusche | G21K 1/06 |
| 2001/0006413 A1 | 7/2001 | Burghoorn | |
| 2002/0085676 A1 | 7/2002 | Snyder | |
| 2003/0142790 A1 | 1/2003 | Zhou et al. | |
| 2003/0223536 A1 | 12/2003 | Yun et al. | |
| 2004/0120463 A1 | 6/2004 | Wilson et al. | |
| 2004/0140432 A1 | 7/2004 | Maldonado et al. | |
| 2005/0074094 A1 | 4/2005 | Jen et al. | |
| 2005/0123097 A1 | 6/2005 | Wang | |
| 2005/0163284 A1 | 7/2005 | Inazuru | |
| 2005/0282300 A1 | 12/2005 | Yun et al. | |
| 2006/0045234 A1 | 3/2006 | Pelc et al. | |
| 2006/0062350 A1 | 3/2006 | Yokhin | |
| 2007/0030959 A1 | 2/2007 | Ritter | |
| 2007/0071174 A1 | 3/2007 | Hebert et al. | |
| 2007/0108387 A1 | 5/2007 | Yun et al. | |
| 2007/0110217 A1 | 5/2007 | Ukita | |
| 2007/0183563 A1 | 8/2007 | Baumann | |
| 2007/0183579 A1 | 8/2007 | Baumann et al. | |
| 2007/0189449 A1 | 8/2007 | Baumann | |
| 2007/0248215 A1 | 10/2007 | Ohshima et al. | |
| 2008/0084966 A1 | 4/2008 | Aoki et al. | |
| 2008/0089484 A1 | 4/2008 | Reinhold | |
| 2008/0094694 A1 | 4/2008 | Yun et al. | |
| 2008/0159707 A1 | 7/2008 | Lee et al. | |
| 2008/0165355 A1 | 7/2008 | Yasui et al. | |
| 2008/0170662 A1 | 7/2008 | Reinhold | |
| 2008/0170668 A1 | 7/2008 | Kruit et al. | |
| 2008/0181363 A1 | 7/2008 | Fenter et al. | |
| 2008/0240344 A1 | 10/2008 | Reinhold | |
| 2008/0273662 A1 | 11/2008 | Yun | |
| 2009/0052619 A1 | 2/2009 | Endoh | |
| 2009/0092227 A1 | 4/2009 | David | |
| 2009/0154640 A1 | 6/2009 | Baumann et al. | |
| 2009/0316860 A1 | 12/2009 | Okunuki et al. | |
| 2010/0012845 A1 | 1/2010 | Baeumer et al. | |
| 2010/0027739 A1 | 2/2010 | Lantz et al. | |
| 2010/0040202 A1 | 2/2010 | Lee | |
| 2010/0046702 A1 | 2/2010 | Chen et al. | |
| 2010/0061508 A1 | 3/2010 | Takahashi | |
| 2010/0091947 A1 | 4/2010 | Niu | |
| 2010/0141151 A1 | 6/2010 | Reinhold | |
| 2010/0246765 A1 | 9/2010 | Murakoshi | |
| 2010/0260315 A1 | 10/2010 | Sato et al. | |
| 2010/0272239 A1 | 10/2010 | Lantz et al. | |
| 2010/0284513 A1 | 11/2010 | Kawabe | |
| 2011/0026680 A1 | 2/2011 | Sato | |
| 2011/0038455 A1 | 2/2011 | Silver et al. | |
| 2011/0058655 A1 | 3/2011 | Okumura et al. | |
| 2011/0064191 A1 | 3/2011 | Toth et al. | |
| 2011/0085644 A1 | 4/2011 | Verman | |
| 2011/0135066 A1 | 6/2011 | Behling | |
| 2011/0142204 A1 | 6/2011 | Zou et al. | |
| 2011/0235781 A1 | 9/2011 | Aoki et al. | |
| 2011/0243302 A1 | 10/2011 | Murakoshi | |
| 2011/0268252 A1 | 11/2011 | Ozawa et al. | |
| 2012/0041679 A1 | 2/2012 | Stampanoni | |
| 2012/0057669 A1 | 3/2012 | Vogtmeier et al. | |
| 2012/0163547 A1 | 6/2012 | Lee et al. | |
| 2012/0163554 A1 | 6/2012 | Tada | |
| 2012/0224670 A1 | 9/2012 | Kiyohara et al. | |
| 2012/0228475 A1 | 9/2012 | Pang et al. | |
| 2012/0269323 A1 | 10/2012 | Adler et al. | |
| 2012/0269324 A1 | 10/2012 | Adler | |
| 2012/0269325 A1 | 10/2012 | Adler et al. | |
| 2012/0269326 A1 | 10/2012 | Adler et al. | |
| 2012/0294420 A1 | 11/2012 | Nagai | |
| 2013/0011040 A1 | 1/2013 | Kido et al. | |
| 2013/0032727 A1 | 2/2013 | Kondoe | |
| 2013/0039460 A1 | 2/2013 | Levy | |
| 2013/0108012 A1 | 5/2013 | Sato | |
| 2013/0108022 A1 | 5/2013 | Kugland et al. | |
| 2013/0195246 A1 | 8/2013 | Tamura et al. | |
| 2013/0223594 A1 | 8/2013 | Sprong et al. | |
| 2013/0259207 A1 | 10/2013 | Omote et al. | |
| 2013/0279651 A1 | 10/2013 | Yokoyama | |
| 2013/0308112 A1 | 11/2013 | Clube et al. | |
| 2013/0308754 A1 | 11/2013 | Yamazaki et al. | |
| 2014/0023973 A1 | 1/2014 | Marconi et al. | |
| 2014/0037052 A1 | 2/2014 | Adler | |
| 2014/0064445 A1 | 3/2014 | Adler | |
| 2014/0072104 A1 | 3/2014 | Jacobsen et al. | |
| 2014/0079188 A1 | 3/2014 | Hesselink et al. | |
| 2014/0105363 A1 | 4/2014 | Chen et al. | |
| 2014/0146945 A1 | 5/2014 | Fredenberg et al. | |
| 2014/0153692 A1 | 6/2014 | Larkin et al. | |
| 2014/0177800 A1 | 6/2014 | Sato et al. | |
| 2014/0185778 A1 | 7/2014 | Lee et al. | |
| 2014/0205057 A1 | 7/2014 | Koehler et al. | |
| 2014/0211919 A1 | 7/2014 | Ogura et al. | |
| 2014/0226785 A1 | 8/2014 | Stutman et al. | |
| 2014/0241493 A1 | 8/2014 | Yokoyama | |
| 2014/0270060 A1 | 9/2014 | Date et al. | |
| 2014/0369469 A1 | 12/2014 | Ogura et al. | |
| 2015/0030126 A1 | 1/2015 | Radicke | |
| 2015/0030127 A1 | 1/2015 | Aoki et al. | |
| 2015/0043713 A1 | 2/2015 | Chen | |
| 2015/0049860 A1 | 2/2015 | Das | |
| 2015/0055743 A1 | 2/2015 | Vedantham et al. | |
| 2015/0055745 A1 | 2/2015 | Holzner et al. | |
| 2015/0092924 A1 | 4/2015 | Yun et al. | |
| 2015/0110252 A1 | 4/2015 | Yun et al. | |
| 2015/0117599 A1 | 4/2015 | Yun et al. | |
| 2015/0194287 A1 | 7/2015 | Yun et al. | |
| 2015/0243397 A1 | 8/2015 | Yun et al. | |
| 2015/0247811 A1 | 9/2015 | Yun et al. | |
| 2015/0260663 A1 | 9/2015 | Yun et al. | |
| 2015/0357069 A1 | 12/2015 | Yun et al. | |
| 2016/0064175 A1 | 3/2016 | Yun et al. | |
| 2016/0066870 A1 | 3/2016 | Yun et al. | |
| 2016/0106387 A1 | 4/2016 | Kahn et al. | |
| 2016/0178540 A1 | 6/2016 | Yun et al. | |
| 2016/0268094 A1 | 9/2016 | Yun et al. | |
| 2016/0320320 A1 | 11/2016 | Yun et al. | |
| 2016/0351370 A1 | 12/2016 | Yun et al. | |
| 2017/0047191 A1 | 2/2017 | Yun et al. | |
| 2017/0052128 A1 | 2/2017 | Yun et al. | |
| 2017/0162288 A1 | 6/2017 | Yun et al. | |
| 2017/0162359 A1 | 6/2017 | Tang et al. | |

(56) References Cited

U.S. PATENT DOCUMENTS

| | | | |
|---|---|---|---|
| 2017/0227476 | A1 | 8/2017 | Zhang et al. |
| 2017/0234811 | A1 | 8/2017 | Zhang et al. |
| 2017/0261442 | A1 | 9/2017 | Yun et al. |
| 2017/0336334 | A1 | 11/2017 | Yun et al. |
| 2018/0144901 | A1 | 5/2018 | Yun et al. |
| 2018/0261352 | A1 | 9/2018 | Matsuyama et al. |
| 2018/0306734 | A1 | 10/2018 | Morimoto et al. |

FOREIGN PATENT DOCUMENTS

| | | |
|---|---|---|
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2003-288853 | 10/2003 |
| JP | 2004-089445 | 3/2004 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-145111 | 6/2008 |
| JP | 2008-197495 | 8/2008 |
| JP | 2009-195349 | 9/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-032387 | 2/2012 |
| JP | 2012-187341 | 10/2012 |
| JP | 2012-254294 | 12/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/1125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
"Element Six CVD Diamond Handbook" (Element Six, Luxembourg, 2015).
"High performance benchtop EDXRF spectrometer with Windows® software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of XS-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.
"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nal'l Lab, Berkeley, CA, Dec. 2008).
"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nal'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published—2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.

(56) References Cited

OTHER PUBLICATIONS

Bech, "In-vivo dark-field and phase-contrast x-ray imaging," Scientific Reports 3, (2013), Article No. 03209.
Bech, "X-ray imaging with a grating interferometer," University of Copenhagan PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.

Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628- 635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Key and 20 Key Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the BESSSY full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.
Honma et al., "Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-RAY Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).

(56) References Cited

OTHER PUBLICATIONS

Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.

Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001).
Li et al., "Source-optic-crystal optimisation for compact monochromatic imaging," Proc. SPIE 5537 (2004), pp. 105-114.
Lohmann et al., "An interferometer based on the Talbot effect," Optics Communications vol. 2 (1971), pp. 413-415.
MacDonald et al., "An Introduction to X-ray and Neutron Optics," Ch. 19 of "Handbook of Optics vol. III, 2nd Ed." (McGraw Hill, New York, 2001).
MacDonald et al., "Polycapillary and Multichannel Plate X-Ray Optics," Ch. 30 of "Handbook of Optics vol. III, 2nd Ed.," (McGraw Hill, New York, 2001).
MacDonald et al., "Polycapillary X-ray Optics for Microdiffraction," J. Appl. Cryst., vol. 32 (1999) pp. 160-167.
MacDonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factor, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviera, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.

(56) References Cited

OTHER PUBLICATIONS

Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer etal., " Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, "Ueber eine neue Art von Strahlen (Wurzburg Verlag, Warzburg, Germany, 1896) also, in English," On a New Kind of Rays, Nature vol. 53 (Jan. 23 1896). pp. 274-276.
Rovezzi, "Study of the local order around magnetic impurities in semiconductors for spintronics." PhD Dissertation, Condensed Matter, Université Joseph-Fourier—Grenoble I, 2009, English <tel-00442852>.

(56) References Cited

OTHER PUBLICATIONS

Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical XRay Fluorescence Analysis," B. Beckhoff et al., eds. (Springer, Berlin Heidelberg, Germay, 2006), pp. 85-198.
Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published 2004 with product release).
Takahama, "RADspeed safire Digital General Radiography System Equipped with New Direct—Conversion FPD," Medical Now, No. 62 (2007).
Takeda et al., "Differential Phase X-ray Imaging Microscopy with X-ray Talbot Interferometer" Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science No. IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.

Tang et al., "Micro-computed tomography (Micro-CT): a novel approach for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot—Lau Interferometer", Jpn. J. Appl. Phys. vol. 47 (2008), pp. 7412-7414.
Wang et al., "Advantages, of intermediate X-ray energies in Zernicke phase constrast X-ray microscopy," Biotech. Adv., vol. 31 (2013) pp. 387-392.
Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD2015.
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.

(56) References Cited

OTHER PUBLICATIONS

Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1 248102-4.
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhang et al., "Fabrication of Diamond Microstructures by Using Dry and Wet Etching Methods", Plasma Science and Technology vol. 15(6) (Jun. 2013), pp. 552-554.
Hennekam et al., "Trace metal analysis of sediment cores using a novel X-ray fluorescence core scanning method," Quaternary Int'l, https://doi.org/10.1016/j.quaint.2018.10.018 (2018).
Malzer et al., "A laboratory spectrometer for high throughput X-ray emission spectroscopy in catalysis research," Rev. Sci. Inst. 89, 113111 (2018).
Viermetz et al., "High resolution laboratory grating-based X-ray phase-contrast CT," Scientific Reports 8:15884 (2018).
Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).
Office Action received in Japanese Application No. 2016-564245, dated Oct. 12, 2018.
Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.
Office Action received in Japanese Application No. 2016-564245, dated Oct. 23, 2018.

\* cited by examiner

X-RAY INTERFEROMETRIC IMAGING SYSTEM

CROSS-REFERENCE TO RELATED APPLICATIONS

This patent application is a Continuation of U.S. patent application Ser. No. 14/527,523, entitled "X-ray Interferometric Imaging System" and filed Oct. 29, 2014, and which in turn claims the benefit of U.S. Provisional Patent Application Nos. 61/898,019, entitled "X-ray Phase Contrast imaging System" and filed on Oct. 31, 2013; 61/901,361, entitled "An X-ray Source Consisting of an Array of Fine Sub-Sources" and filed on Nov. 7, 2013; and 61/981,098 entitled "Two Dimensional Phase Contrast Imaging Apparatus" and filed Apr. 17, 2014, all of which are incorporated herein by reference in their entirety.

FIELD OF THE INVENTION

The embodiments of the invention disclosed herein relate to interferometric imaging systems using x-rays, and in particular, interferometric imaging systems comprising high-brightness sources of x-rays for generating phase-contrast images. The high brightness x-ray sources may use anodes or targets comprising periodic microstructures of x-ray generating materials embedded in a thermally conducting substrate of low atomic number material.

BACKGROUND OF THE INVENTION

The initial discovery of x-rays by Röntgen in 1895 [W. C. Röntgen, "Eine Neue Art von Strahlen (Würzburg Verlag, 1896); "On a New Kind of Rays," Nature, Vol. 53, pp. 274-276 (Jan. 23 1896)] occurred when Röntgen was experimenting with electron bombardment of targets in vacuum tubes. The contrast between the absorption from bone containing calcium (atomic number Z=20) and soft tissue containing mostly carbon (Z=6), was immediately apparent because the absorption difference between the two materials at x-ray energies between 5 and 30 keV can differ by a factor of 10 or more, as illustrated in FIG. 1. These high energy, short wavelength photons are now routinely used for medical applications and diagnostic evaluations, as well as for security screening, industrial inspection, quality control and failure analysis, and for scientific applications such as crystallography, tomography, x-ray fluorescence analysis and the like.

Although x-ray shadowgraphs have become a standard medical diagnostic tool, there are problems with simple absorption contrast imaging. Notably, for tests such as mammograms, variations in biological tissue may result in only a subtle x-ray absorption image contrast, making unambiguous detection of tumors or anomalous tissue difficult.

In the past decade, a new kind of x-ray imaging methodology has emerged, based on x-ray phase contrast interferometry. The method relies on the well-known Talbot interference effect, originally observed in 1837 [H. F. Talbot, "Facts relating to optical science No. IV", Philos. Mag. vol. 9, pp. 401-407, 1836] and fully explained by Lord Rayleigh in 1881 [Lord Rayleigh, "On copying diffraction gratings and some phenomena connected therewith," Philos. Mag. vol. 11, pp. 196-205 (1881)].

This effect is illustrated in FIG. 2. For an absorbing grating G of period p, the diffraction pattern from a monochromatic beam of a wavelength $\lambda$ with sufficient coherence forms a repeating interference pattern that reconstructs the original grating pattern, (known as a "self-image") at multiples of a distance known as the Talbot Distance $D_T$. For the case when the incident beam is a plane wave (equivalent to a source located at infinity from the grating G), $D_T$ is given by:

$$D_T = \frac{2p^2}{\lambda} \qquad \text{[Eqn. 1]}$$

Between the grating G and the Talbot Distance, other periodic interference patterns emerge as well. The periodicity and the position of the Talbot fringes depend on the transmission properties of the grating G, including amount of phase-shift and percent of absorption, and grating line-to-space (opening) ratio, or duty factor. For example, for a periodic absorption grating, a fringe pattern that reconstructs of the original grating pattern with a lateral shift by half the grating period occurs at half the Talbot Distance $D_T/2$, and a fringe pattern with a period of half of the original grating period occurs at one quarter of the Talbot Distance $D_T/4$ and at three quarters of the Talbot Distance $3D_T/4$, as illustrated in FIG. 2. These 2-D interference patterns are sometimes called a "Talbot Carpet" because of the resemblance of these complex patterns to ornate oriental carpets. [Note: this image of an Optical Talbot Carpet in FIG. 2 is adapted from a file created by Ben Goodman and available at <http://commons.wikimedia.org/wiki/File:Optical_Talbot_Carpet-.png>.]

FIGS. 3 and 4 illustrate a prior art Talbot interferometric comprising a partially coherent source 200 (shown as a microfocus source) of x-rays 288 and a beam splitting grating $G_1$ 210 of period $p_1$ that establishes a set of Talbot interference fringe patterns 289. It should be noted that the coherence length of the x-ray source is preferably set to be comparable to or larger than the period $p_1$ of the beam splitting grating $G_1$ 210, so that the Talbot interference fringes will have high contrast. The beam splitting grating 210 may be an amplitude (also known an absorption or transmission) grating, creating intensity fringes as illustrated in FIG. 2, but is more typically a phase grating for efficient use of the illuminating x-rays, introducing periodic phase-shifts to the x-ray pattern that also form periodic Talbot fringes 289. Henceforth in this application, a transmission grating will be used to describe gratings in which the x-ray transmission through the grating lines is less than 10% and a phase grating will be used to describe gratings in which the phase shift through the grating lines is a fraction (e.g. ½) or odd integer multiple of $\pi$.

The Talbot fringes 289 are detected using an x-ray detector 290, preferably with a spatial resolution equal to or better than one third of the Talbot fringe period and having a high x-ray quantum detection efficiency. The detector 290 transforms the x-ray intensity pattern into electronic signals that are transmitted over a connector 291 to an image processing system 295. When an object is placed in the beam path, the image processing system 295 is used to process the x-ray intensity pattern intensity information 298 to obtain absorption, phase, and scattering contrast images.

In practice, the spatial resolution of the detector 290 (such as a flat panel detector, or a charge coupled device (CCD) detector coupled with a scintillator that converts x-rays to visible light) is often on the order of tens of micrometers or larger, and the Talbot fringes 289 may be too fine to detect directly with the detector 290. In this case, an analyzer grating $G_2$ 220 of period $p_2$ is often used to produce Moiré fringes. To record a complete set of images, the analyzer grating $G_2$ 220 will be moved in predetermined distances orthogonal to the grating period and relative to the detector to collect multiple interference patterns in a process called "phase-stepping", or less commonly, rotated at a small angle relative to $G_1$ to obtain a Moiré pattern in a single-shot image for Fourier analysis. The image(s) are then processed to reconstruct the wavefront and determine the shapes, structures, and composition of the objects that created them.

It should also be noted that, instead of physically moving the analyzer grating 220, the position of the x-ray source may also be displaced to create a translation of the interference images that allows the collection of phase-shift information. This can be accomplished electronically by moving the position of the electron beam that bombards the x-ray generating material that serves as the source for the x-rays [see, for example, H. Miao et al., "Motionless phase stepping in X-ray phase contrast imaging with a compact source", Proceedings of the National Academy of Sciences, vol. 110(48) pp. 19268-19272, 2013] or by physically moving the x-ray source relative to a fixed position of the analyzer grating 220.

These grating-based x-ray phase-contrast imaging (XPCI) techniques are generally referred to as "grating-based interferometry" (GBI).

As illustrated so far, the grating interferometer only produces interference fringes, and the analysis of these fringes will reveal the structure of the already known grating $G_1$ 210 or the wavefront of the illumination beam. However, when an object is introduced in the path of the x-ray beam, variations in the wavefront introduced by the object result in corresponding changes in the pattern of the Talbot interference fringes, generally known as Moiré fringes. Interferometric image reconstruction techniques may then be used to analyze the wavefront and reconstruct images representing the structure of the unknown object.

In FIG. 5, the prior art Talbot interferometer of FIGS. 3 and 4 is illustrated being used as an imaging technique for a biological sample, in this case, a mouse 240-M, placed between the source 200 and the beam splitting grating $G_1$ 210. The x-rays 288 from the coherent source 200 pass through the mouse 240-M and the beam splitting grating $G_1$ 210 and create a perturbed set of Talbot fringes 289-M. The local phase shifts create angular deviations that translate into changes of locally transmitted intensity when analyzed by the analyzer grating $G_2$ 220 and detector 290. Collecting multiple images from the x-ray detector 290 for situations where the analyzer grating $G_2$ 220 has been displaced by multiple predetermined positions allow a recording of the interference pattern 289-M.

As before, the detector 290 transforms the x-ray intensity pattern into electronic signals that transmitted over a connector 291 to an image processing system 295 used to produce one or more images 298-M with absorption, differential phase, phase, and scattering contrast information. Numerical processing of the images, including images collected by the system with and without the object under investigation, can be used to infer the shapes and structure of the objects that created them, including objects such as the mouse 240-M. The recorded intensity oscillations can be represented by a Fourier series, and with the proper image processing algorithms, differential phase shift and absorption signals can be extracted, and images corresponding to x-ray absorption, phase contrast, and scattering by the object can be synthesized. [See, for example, A. Momose et al., "Demonstration of x-ray Talbot interferometry", Jpn. J. Appl. Phys. 42, pp. L866-L868, 2003; A. Momose, U.S. Pat. No. 7,180,979, issued Feb. 20, 2007; and T. Weitkamp et al. "Hard X-ray phase imaging and tomography with a grating interferometer", Proc. SPIE vol 5535, pp. 137-142, 2004, and "X-ray phase imaging with a grating interferometer", Optics Express vol. 13(16), pp. 6296-6304, 2005.]

It should be noted that other configurations exist in which the object, such as a mouse 240-M, can be placed between the beam splitting grating $G_1$ 210-A and the analyzer grating $G_2$ 220 and detector 290, as illustrated in FIG. 6. Other configurations using various phase and amplitude gratings, or using detector 290 with higher resolution pixels without the analyzer grating 220, may also be known to those skilled in the art.

Aside from imaging the anatomy of mice, clinical applications of phase-contrast x-ray imaging may be found in mammography, where the density of cancerous tissue may have a distinct phase signature from healthy tissue [see, for example, J. Keyriläinen et al., "Phase contrast X-ray imaging of breast", Acta Radiologica vol. 51 (8) pp. 866-884, 2010], or for bone diseases like osteoporosis or osteoarthritis, in which the angular orientation of the bone structures may be an early indicator of bone disease [See, for example, P. Coan et al., "In vivo x-ray phase contrast analyzer-based imaging for longitudinal osteoarthritis studies in guinea pigs", Phys. Med. Biol. vol. 55(24), pp. 7649-62, 2010].

However, for the prior art configurations described so far, x-ray power is a problem. An x-ray source with a full-width half maximum diameter S given by $$S \leq \frac{\lambda L}{2\pi p_1} \quad \text{[Eqn. 2]}$$

where $p_1$ is the period of the beam splitting grating $G_1$ 210 and L the distance between the source 200 and the beam splitting grating $G_1$ 210, is required for the technique to produce high contrast fringes and Moiré patterns. For practical applications and system geometries, this implies a microfocus source. However, electron bombardment of the target also causes heating, and the x-ray power that can be achieved is limited by the maximum total electron power that can fall on the microspot without melting the x-ray generating material. A limited electron power means a limited x-ray power, and the low x-ray flux achievable with typical x-ray targets may lead to unacceptable long exposure times when used, for example, for mammography or other diagnostic tests involving live patients or animals. The total x-ray flux can be increased by distributing higher electron power over a larger area, but then the source becomes less coherent, degrading the image contrast.

Coherent x-rays of higher brightness and sufficient flux can be achieved by using a synchrotron or free-electron laser x-ray source, but these machines may occupy facilities that cover acres of land, and are impractical for use in clinical environments.

One innovation that has been shown to enable greater x-ray power employs an additional grating $G_0$ [see, for example, John F. Clauser, U.S. Pat. No. 5,812,629, issued Sep. 22, 1998]. Such a system is illustrated in FIG. 7. In this configuration, a source grating $G_0$ 308 with period $p_0$, which is typically an x-ray transmission grating, is used in front of an x-ray source 300. In this case, the x-ray source may be a high-power extended source with a large incident electron beam area (and not a microfocus source) that produces a higher total flux of x-rays.

The x-rays 388 pass through the grating $G_0$ 308 and emerge from the grating apertures as an array of individually spatially coherent (similar to a microfocus source described above) but mutually incoherent sub-sources of illumination for the beam splitting grating $G_1$. To ensure that each x-ray sub-source in $G_0$ contributes constructively to the image-formation process, the geometry of the setup should satisfy the condition:

$$p_0 = p_2 \frac{L}{D} \quad [\text{Eqn. 3}]$$

When the condition is met, the x-rays from the many apertures of $G_0$ produce the same (overlapping) Talbot interference pattern, and because the various mutually incoherent sources do not interfere with each other, these Talbot patterns will add as intensities. The effect at the detector 290 is therefore to simply increasing the signal (along with it the signal-to-noise ratio) over what a single coherent source can provide.

This configuration is called the Talbot-Lau interferometer [see Franz Pfeiffer et al., "Phase retrieval and differential phase-contrast imaging with low-brilliance X-ray sources", *Nature Physics* vol. 2, pp. 258-261, 2006; and also Described in U.S. Pat. No. 7,889,838 by Christian David, Franz Pfeiffer and Timm Weitkamp, issued Feb. 15, 2011].

FIG. 8 illustrates x-ray images of a live mouse collected using a Talbot-Lau interferometer, as reported by Martin Bech [M. Bech et al., "In-vivo dark-field and phase-contrast x-ray imaging", *Scientific Reports* 3, Article number: 3209, 2013, FIG. 1]. The x-ray energy used was 31 keV, and the gratings were fabricated by lithographically etching structures in silicon (Z=14). Absorption gratings $G_0$ for the source and $G_2$ for the analyzer were created by additionally coating the patterned silicon with gold (Z=79).

All of the images of FIG. 8 were reported as reconstructed from the same set of 5 interferometric images, each collected over an exposure time of 10 seconds. The raw images were Fourier processed and ramp corrected to obtain the three image modalities. FIG. 8A illustrates an intensity image based on x-ray attenuation, showing the absorption contrast between the bones and soft tissue. FIG. 8B illustrates a phase-contrast image, which clearly identifies soft tissue structures such as the trachea (illustrated with an arrow). FIG. 8C illustrates an additional dark-field contrast image due to x-ray scattering from fine features with linear dimensions less than the spatial resolution of the imaging system, which strongly highlights the fur and lungs.

Unfortunately, the current art of Talbot-Lau GBIs have many constraints for most practical applications such as clinical imaging, including a requirement that both the source grating $G_0$ and the analyzer grating $G_2$ have fine pitches and apertures with large aspect ratios.

The requirement for the source grating $G_0$ is to create fine individual well-separated x-ray sub-sources to minimize the reduction in image contrast due to unwanted transmission of x-rays through the aperture defining structures. However, for a 1:1 line-to-space ratio grating, simple x-ray shadowing dictates that the x-ray transmission through the grating is limited to less than 50%, and is reduced further when the angular shadowing (limiting the angular range of the x-rays from the source to reach the object) is included. Furthermore, the optimal line-to-space ratio for $G_0$ that reduces the radiation dose to the object (which is important to preclinical and clinical imaging applications) is closer to 3:1 rather than 1:1. In this case, about 75% of the x-rays from the source are blocked due to area shadowing alone, and when gratings with large aspect ratios are used, greater losses occur due to angular shadowing.

The requirement for the analyzer grating $G_2$ is to be able to sample the Talbot interference fringes with sufficient resolution without losing contrast. As a result, both the $G_0$ and $G_2$ gratings must have small apertures and be of thickness sufficient to minimize unwanted x-ray transmission, which limits the efficient use of the x-rays from the source. Furthermore, the loss from the analyzer grating $G_2$ further results in a significantly higher dose (relative to the same system without a $G_2$ grating) for the object under investigation to produce an image with good characteristics due to multiple exposures for phase-stepping and absorption of x-rays resulting in lower signal-to-noise. When the object under investigation is a live animal or human, higher doses of ionizing radiation are undesirable and generally discouraged.

If the aperture dimensions of the grating $G_0$ are larger, angular collimation can be reduced (although not the area shadowing) so that x-ray transmission is not reduced as severely, but this reduces the spatial coherence length of the x-ray beam downstream from the apertures, and leads a reduction in image contrast. Smaller apertures can increase the possible image contrast and resolution by improving spatial coherence, but decreases the overall number of x-rays in the system, thus requiring longer exposure times. Moreover, with smaller apertures, these fine gratings become more difficult to manufacture.

The problem is exacerbated when attempting to use a Talbot-Lau interferometer for higher energy x-rays, which are often desired to obtain sufficient transmission through an object and to reduce ration does. In general, as was illustrated in FIG. 1, the absorption of x-rays for biological tissue is far lower for x-rays with energy greater than 5 keV, and the use of higher energy x-rays will reduce the absorbed dose of potentially harmful ionizing radiation by orders of magnitude. However, 5 keV photons have a wavelength of 0.248 nm, and 50 keV have a wavelength 10 times smaller (0.0248 nm). Furthermore, building absorbing gratings such as $G_0$ and $G_2$ for these higher energy, shorter wavelength x-rays can present difficulties, as the thickness of the gratings must increase exponentially to maintain the same absorption factor for higher energy x-rays (the x-ray attenuation length is approximately proportional to $E_{kev}^3$).

The preceding problems of Talbot-Lau GBIs using linear gratings, which can be used for collecting interference data in one dimension only, become more severe if one wishes to generate phase-contrast images in two orthogonal directions. This is often required to make the image reconstruction robust and images more understandable, and because features parallel to the grating lines in the 1-D case are typically less accurately measured. One simple approach is to perform XPCI in two orthogonal directions and then subsequently register the two datasets properly. In addition to challenges associated with the imaging and registration processes, this approach may not be practical, especially when used with living subjects who may move or simply become impatient, and who will incur increased dosage (doubled) if the phase stepping must be performed in two directions. Simultaneous two-dimensional XPCI would be desirable, especially if data collection in a single exposure (shot) and at high x-ray energies is possible to reduce exposure times and the absorbed dosage.

There is therefore a need for an x-ray interferometric imaging system that offers the resolution and detection capabilities of the Talbot-Lau interferometer, but employing a brighter compact source of x-rays and, ideally, a brighter source of higher energy x-rays, especially one that could provide simultaneous two-dimensional phase-contrast imaging.

BRIEF SUMMARY OF THE INVENTION

We disclose here an x-ray interferometric imaging system in which the x-ray source comprises a target having a plurality of microstructured x-ray generating materials arranged within a periodic array pattern to form periodic sub-sources of x-rays. The system additionally comprises a beam-splitting grating $G_1$ that creates a Talbot interference pattern, and an x-ray detector to convert two-dimensional x-ray intensities into electronic signals.

If the spatial resolution of the detector is equal to or better than one third of the Talbot fringe period, the detector may record the fringes directly. The system may also comprise a second analyzer grating $G_2$ that may be placed in front of the detector to form additional interference fringes, and a means to translate the analyzer grating $G_2$ relative to the detector to create Moiré fringes at the detector. Additionally, the system may comprise a means of translating the phase grating $G_1$ relative to the analyzer grating $G_2$.

The x-ray source target comprises a plurality of microstructures of x-ray generating materials (such as molybdenum or tungsten) in close thermal contact with a thermally conducting substrate of a low atomic number material, such as diamond or beryllium. The x-ray generating microstructures may be arranged in a periodic pattern, with each periodic element of the pattern corresponding to a single discrete microstructure or alternatively, with each periodic element of the pattern comprising multiple discrete microstructures. One or more sources of electrons bombard the plurality of x-ray generating materials, which are generally arranged within a periodic array, so that the x-ray generated from each periodic array element serves as an individually coherent sub-source of x-rays of illumination for the beam splitting grating $G_1$. In some embodiments, the microstructures have lateral dimensions measured on the order of microns, and with a thickness on the order of one half of the electron penetration depth within the substrate material. In some embodiments, the microstructures are formed in a regular two-dimensional array.

The beam splitting grating $G_1$ may be a phase grating or an absorption grating. The analyzer grating $G_2$ is generally a transmission grating. Both gratings $G_1$ and $G_2$ may be fabricated as lithographically produced microstructures in silicon, and may comprise 1-D structures, 2-D structures, or combinations thereof.

A particular advantage of the invention is that high x-ray brightness and large x-ray power may be achieved by using an x-ray target in which the microstructures of a high Z material are in close thermal contact with, or embedded in, a substrate of low Z material and high thermal conductivity, such as beryllium or diamond. The ability of the substrate to draw heat away from the x-ray generating material allows higher electron density and power to be used, generating greater x-ray brightness and power from each of the sub-sources. This results in the creation of individual, well-separated spatially coherent x-ray sub-sources from the high Z material, while the use of a substrate with low Z and low mass density minimizes the production of x-rays from the substrate that can lead to a reduction in image contrast.

Figure 1:
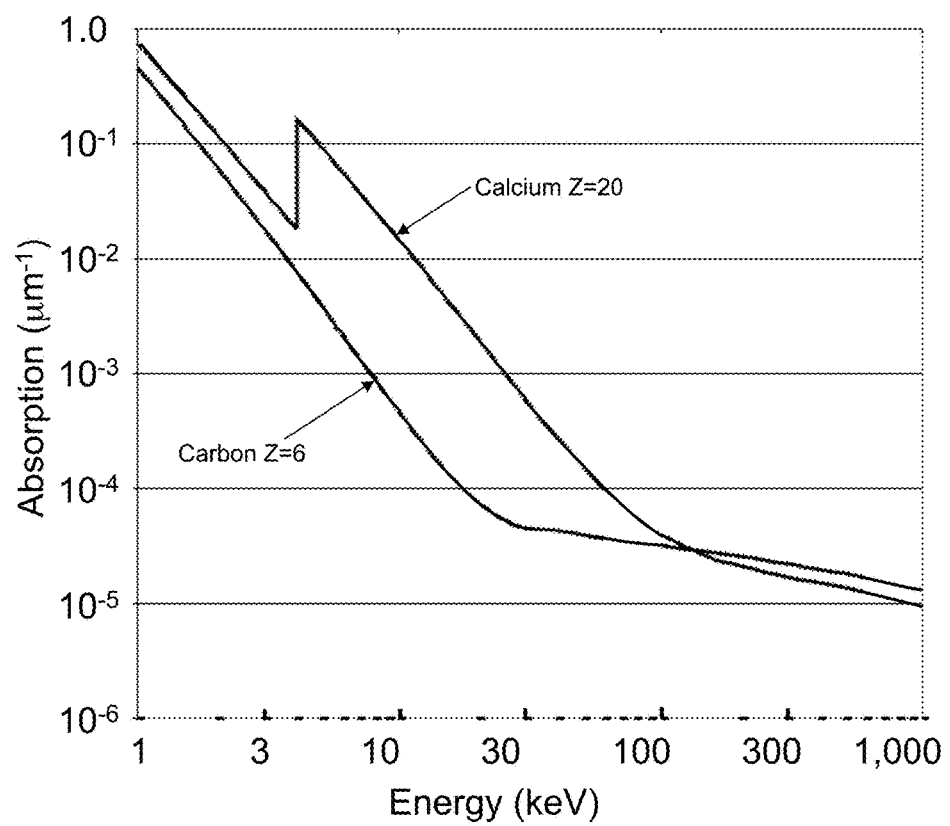
FIG. 1 illustrates a plot of the x-ray absorption of carbon and calcium as a function of x-ray energy.
Figure 2:
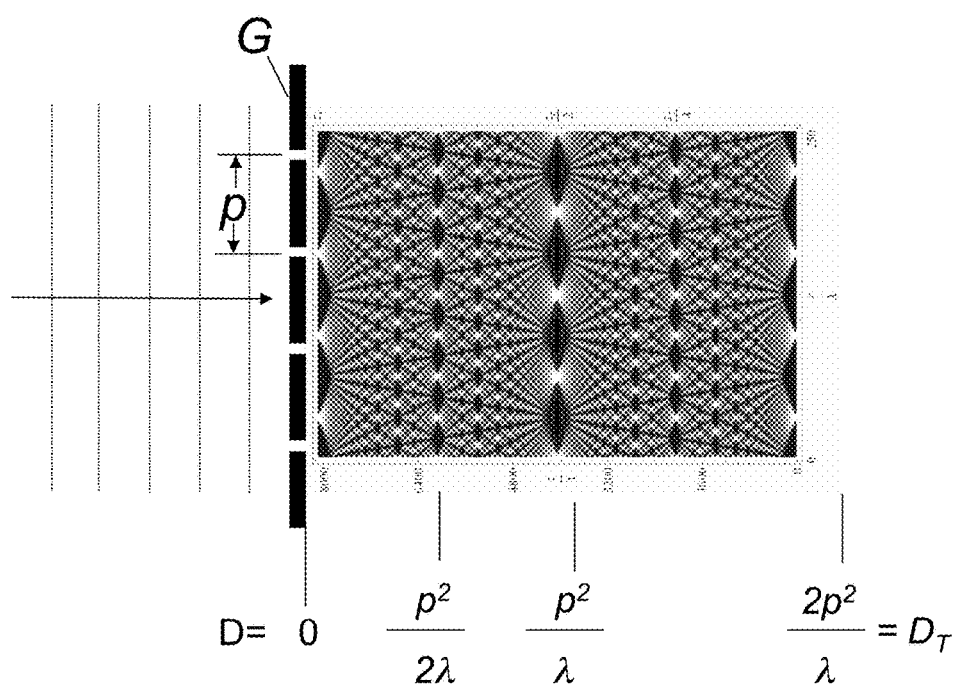
FIG. 2 illustrates a prior art Talbot interference pattern produced by a transmission grating.
Figure 3:
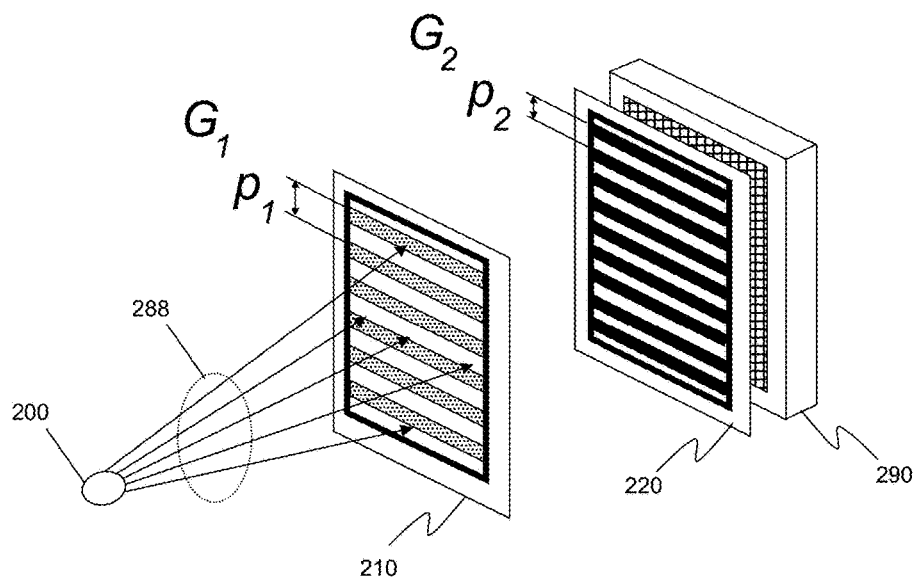
FIG. 3 illustrates a prior art x-ray grating interference system using a microfocus source.
Figure 4:
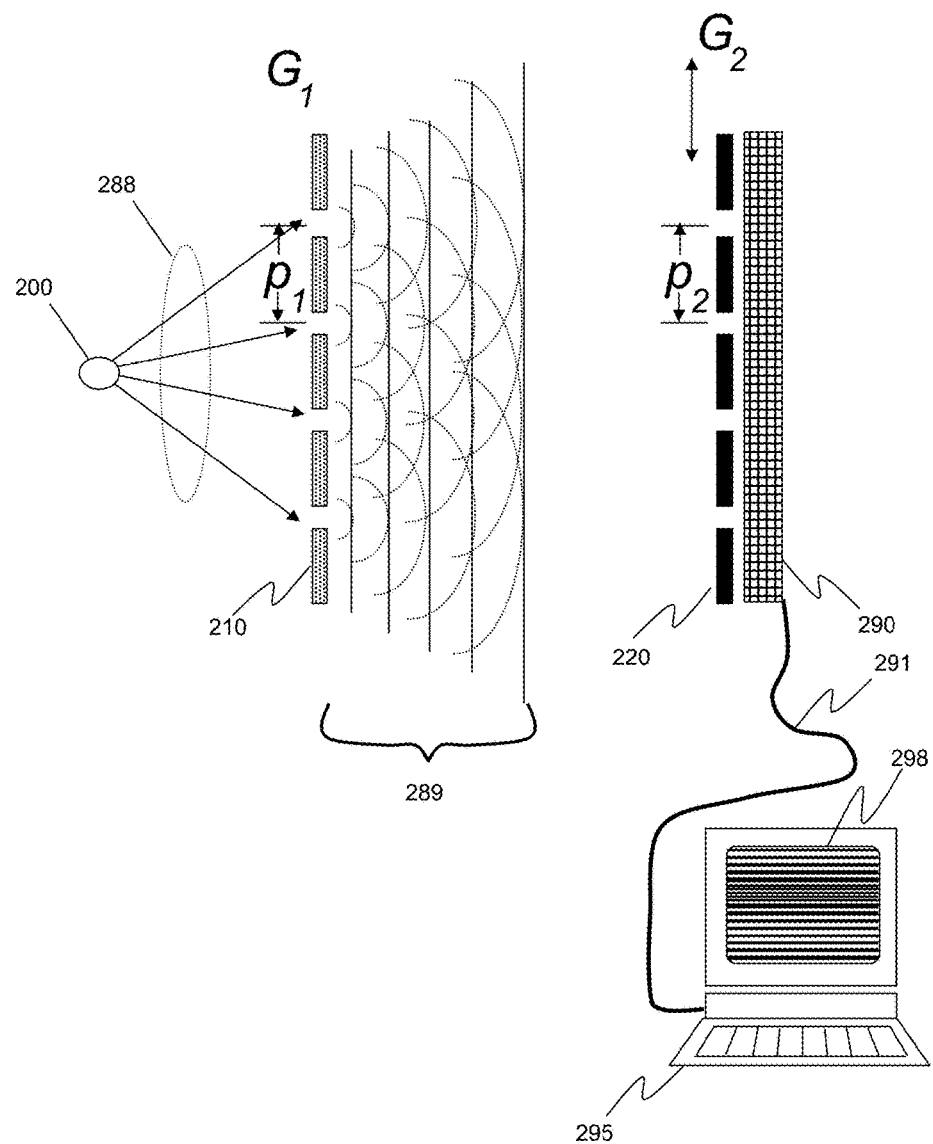
FIG. 4 illustrates a cross section view of the prior art x-ray grating interference system of FIG. 3.
Figure 5:
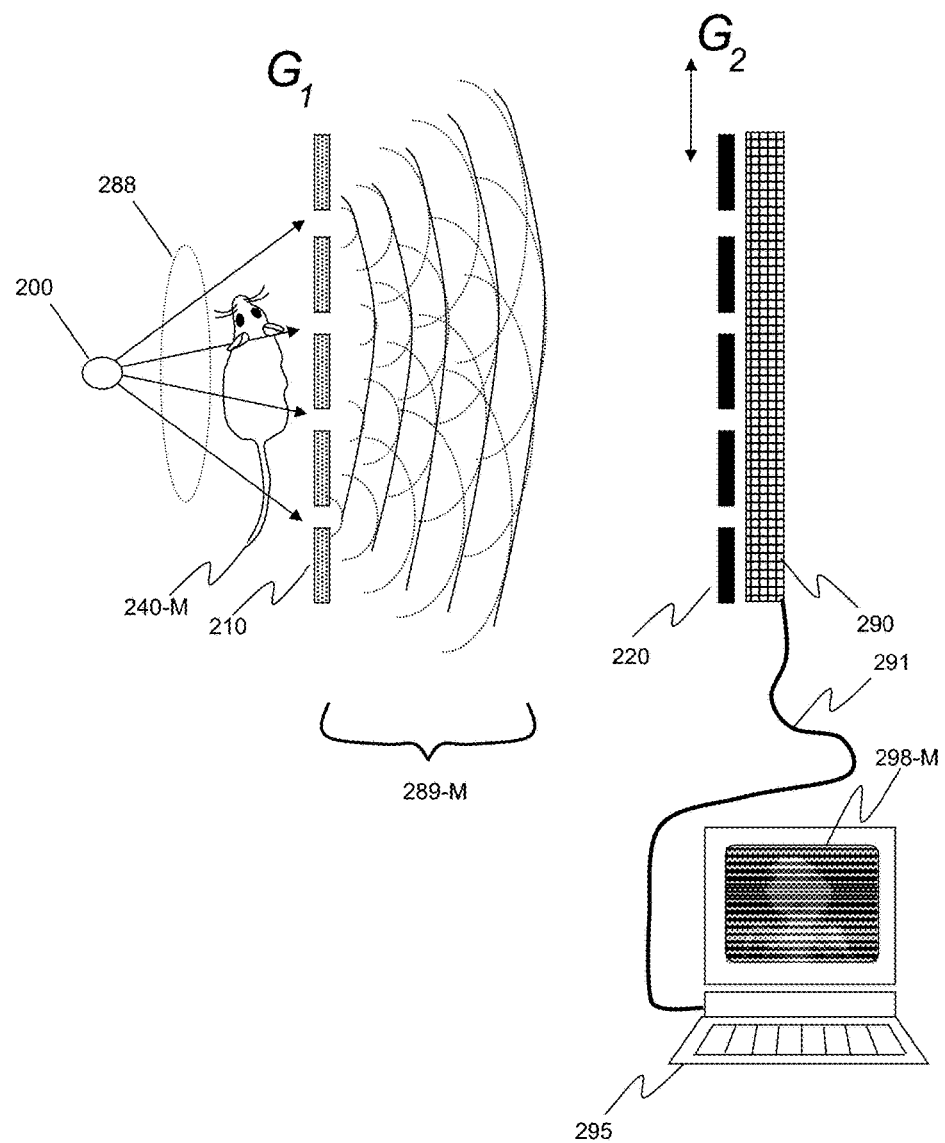
FIG. 5 illustrates the prior art x-ray grating interference system of FIG. 3 used to form an x-ray contrast image of a mouse.
Figure 6:
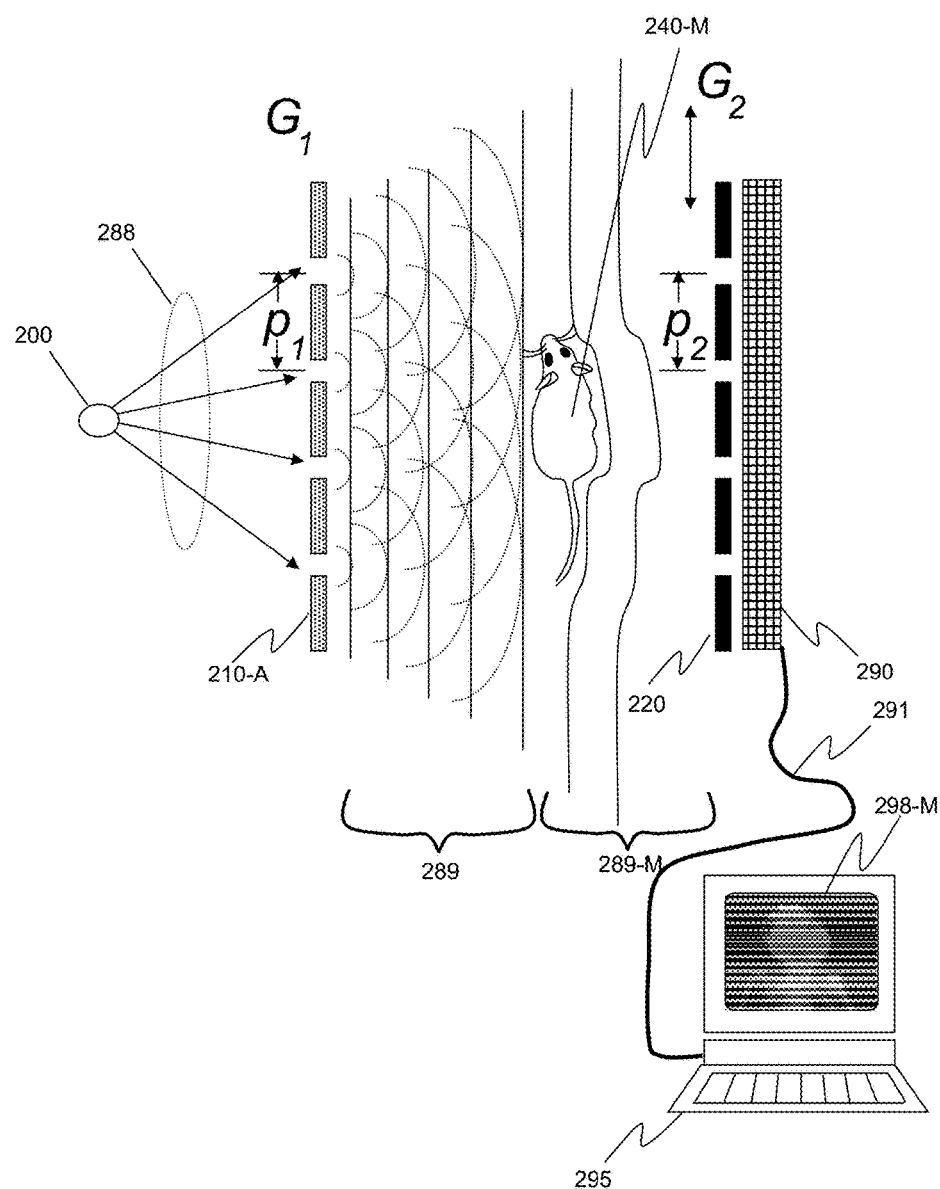
FIG. 6 illustrates a variation of the prior art x-ray grating interference system of FIG. 3 used to form an x-ray contrast image of a mouse.
Figure 7:
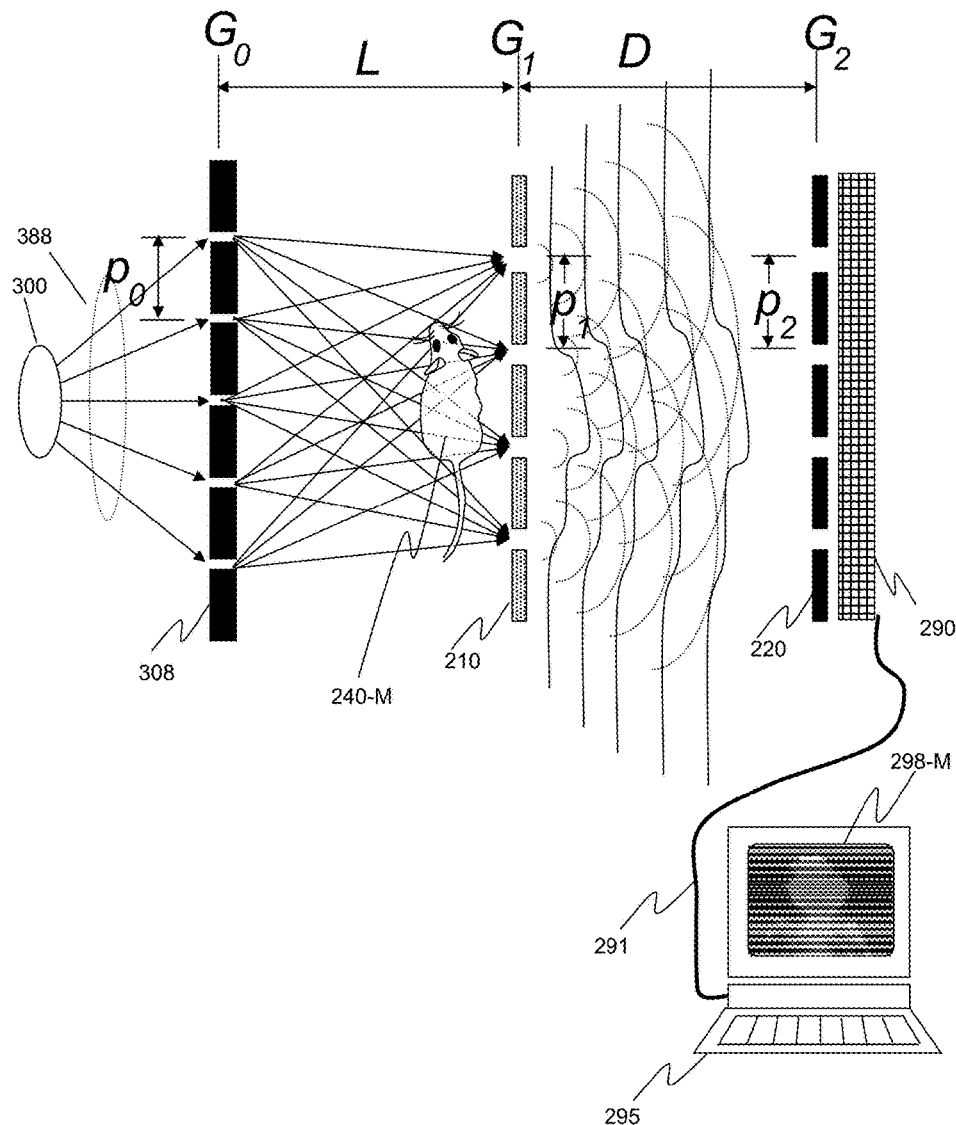
FIG. 7 illustrates a prior art Talbot-Lau interferometer being used to form an x-ray contrast image of a mouse.
Figures 8A, 8B, 8C:
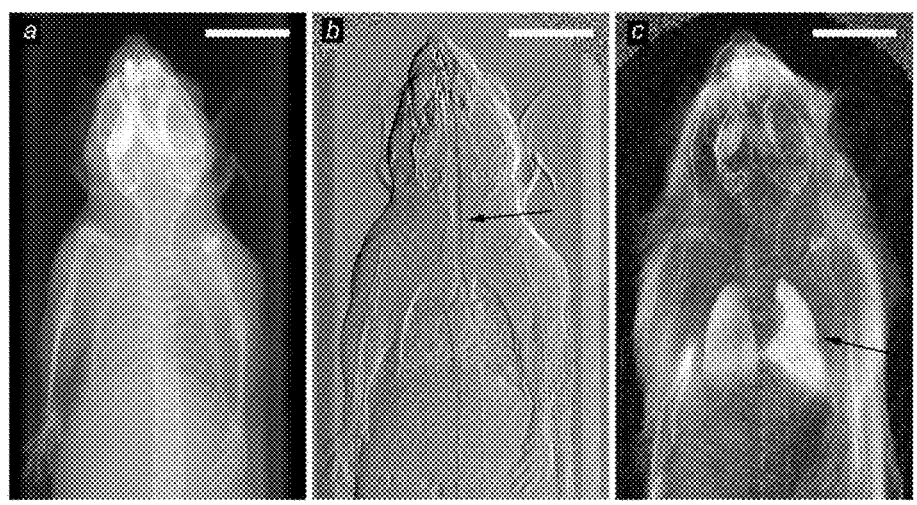
FIG. 8A illustrates a published x-ray absorption image of a mouse gathered using a prior art Talbot-Lau interference system.
FIG. 8B illustrates a published x-ray phase-contrast image of a mouse gathered using a prior art Talbot-Lau interference system.
FIG. 8C illustrates a published x-ray dark field scattering image of a mouse gathered using a prior art Talbot-Lau interference system.

Note: The illustrations in the Drawings disclosed in this Application are typically not shown to scale, and are meant to illustrate the principle of the invention and its function only, and not specific relationships between the microstructures in the target and the various grating periods $p_1$, $p_2$ and $p_3$. Please refer to the descriptions in the text of the Specification for specific details of the dimensions of these objects.

DETAILED DESCRIPTIONS OF EMBODIMENTS OF THE INVENTION

1. Descriptions of Various Embodiments of the Invention

Figure 9:
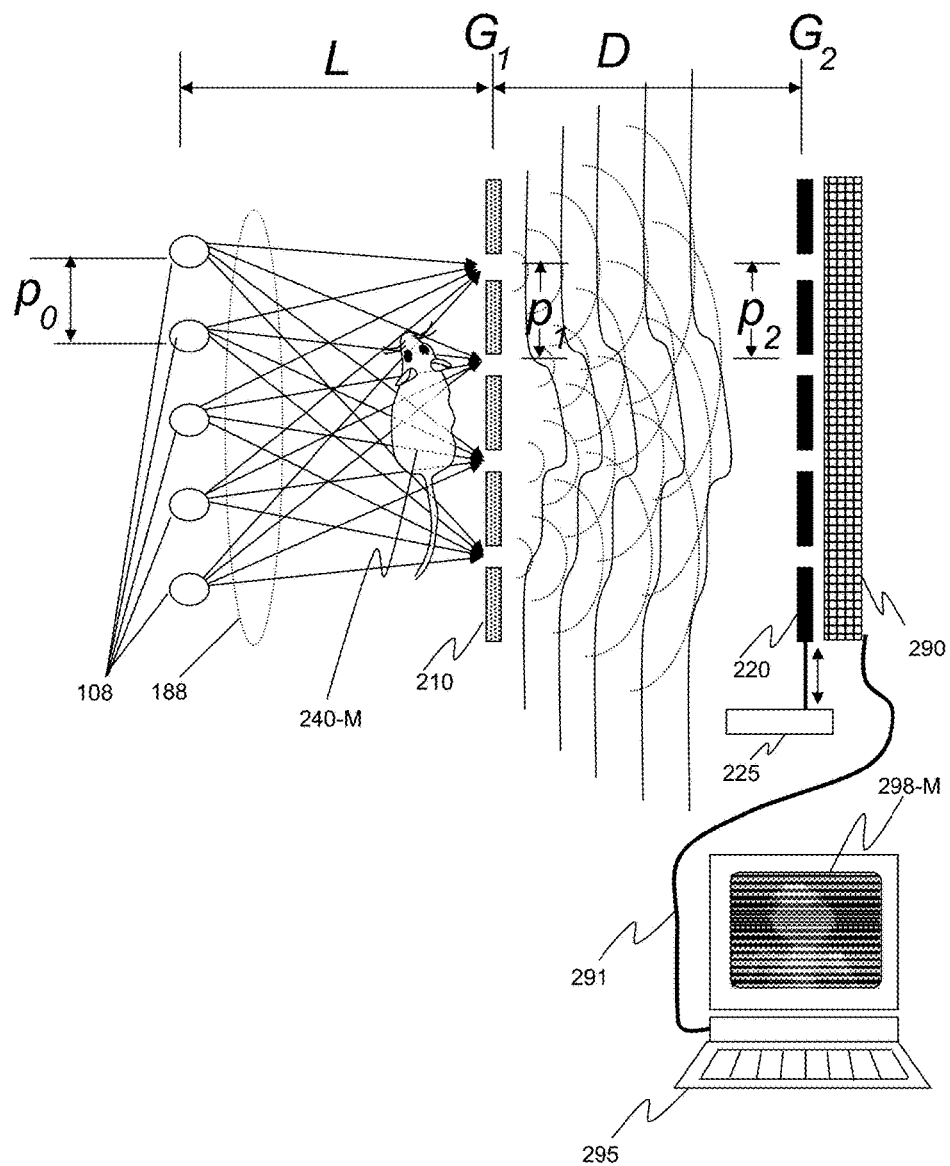
FIG. 9 illustrates a schematic cross-section view of an embodiment of an x-ray interferometric imaging system according to the invention.

One embodiment of the invention disclosed herein is an x-ray phase-contrast imaging (XPCI) system as illustrated in FIG. 9. The system bears some similarity to the prior art Talbot-Lau interferometer, in that it comprises a beam splitting grating $G_1$ 210 of period $p_1$ that establishes a Talbot interference pattern, and an x-ray detector 290 typically comprising an array of sensors to convert two-dimensional x-ray intensities into electronic signals. The beam splitting grating $G_1$ 210 may be a phase grating or a transmission grating, and may comprise 1-D periodic patterns (linear gratings), or may comprise more complex 2-D structures such as a grid that is periodic in two orthogonal directions. The system may also comprise an analyzer grating $G_2$ 220 of period $p_2$ that may be placed in front of the detector to form additional interference fringes, such as Moiré fringes. The system may additionally comprise a means 225 to translate the analyzer grating $G_2$ 220 relative to the detector, and a connector 291 to transmit electronic signals corresponding to the detected x-ray intensity to an image processing system 295 for processing.

However, instead of using an extended x-ray source and an additional grating $G_0$ to create a plurality of x-ray source spots, as was done in the Talbot-Lau system, the embodiments of the present invention use an x-ray source comprising a plurality of x-ray generating sub-sources 108 arranged in a periodic array that generate x-rays 188 from electron beam bombardment, such that each sub-source is individually coherent, but together function as a set of mutually incoherent or partially coherent sub-sources of illumination for the beam splitting grating $G_1$. As with the combination of the extended x-ray source and the source grating of the Talbot-Lau interferometer, these sub-sources 108 form the Talbot interference fringe patterns that are created by the beam splitting grating $G_1$ 210 and perturbed by an object 240-M, and may be recorded by detector 290. If the spatial resolution of the detector 290 has a spatial resolution equal to or better than one third of the Talbot fringe period, the detector may record the fringes directly. If a lower resolution detector is used, an analyzer grating $G_2$ 220 may also be used to create Moiré fringes, as was described for the Talbot-Lau interferometer.

The plurality of discrete x-ray sub-sources can be considerably brighter than the x-ray source of the Talbot-Lau system. Because the source comprises sub-sources that are self-coherent but may be mutually incoherent, there is no need for an attenuating transmission grating $G_0$ to create an array of sub-sources from an extended x-ray source.

A system according to the invention comprising multiple sub-sources in a structured target may be designated a Talbot-ST interferometer.

Figure 10:
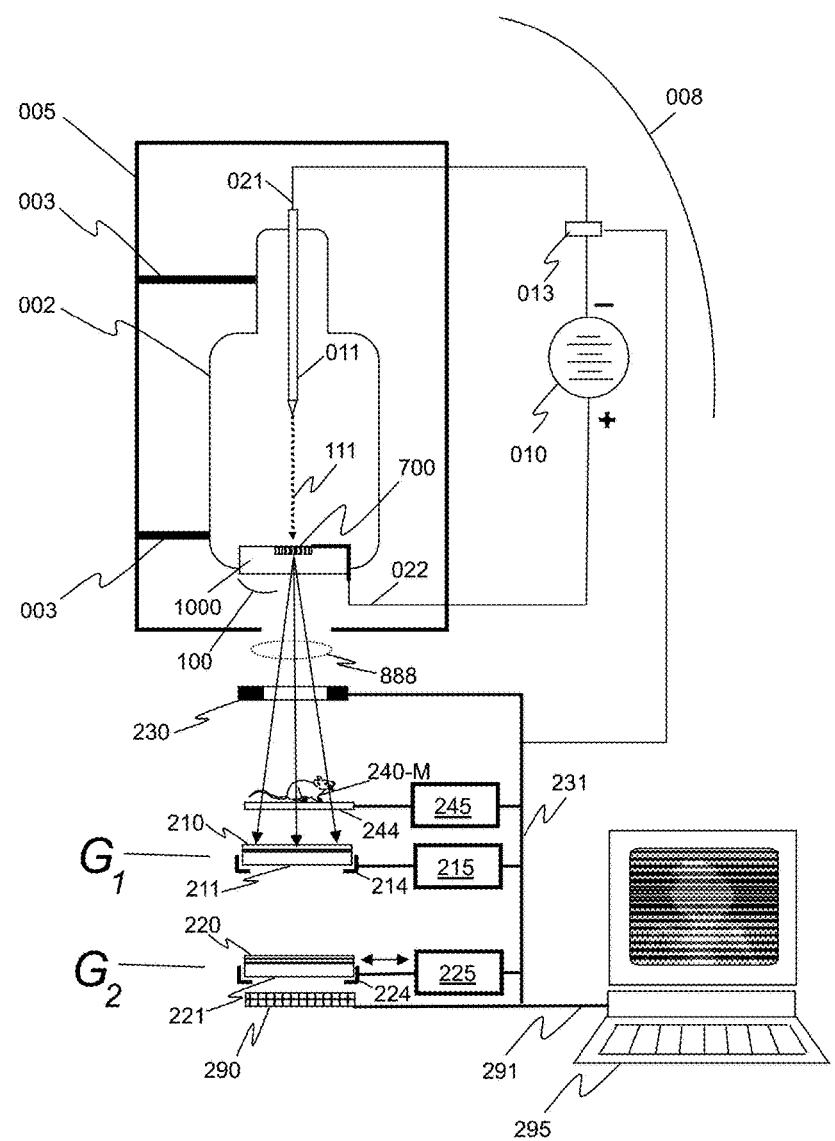
FIG. 10 illustrates a schematic cross-section view of an embodiment of the invention.
Figure 11:
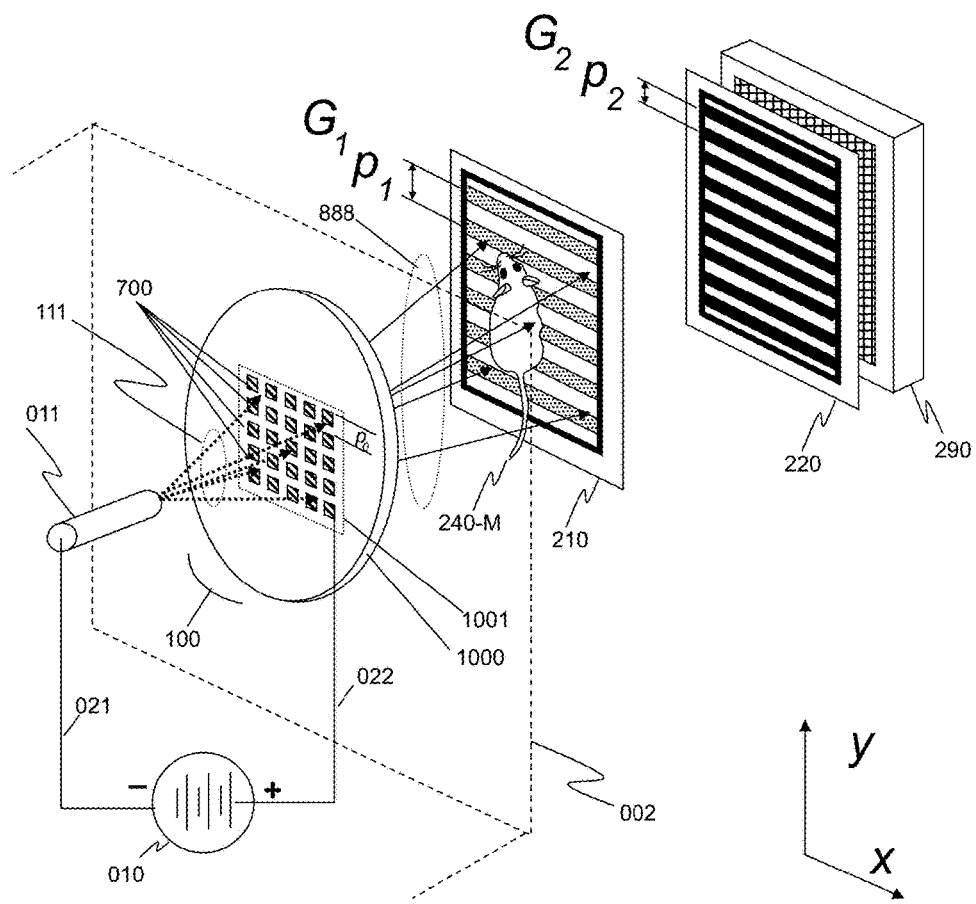
FIG. 11 illustrates a perspective view of the embodiment of the invention shown in FIG. 10, in which the x-ray target comprises two dimensional periodic array of x-ray generating microstructures.
Figure 12:
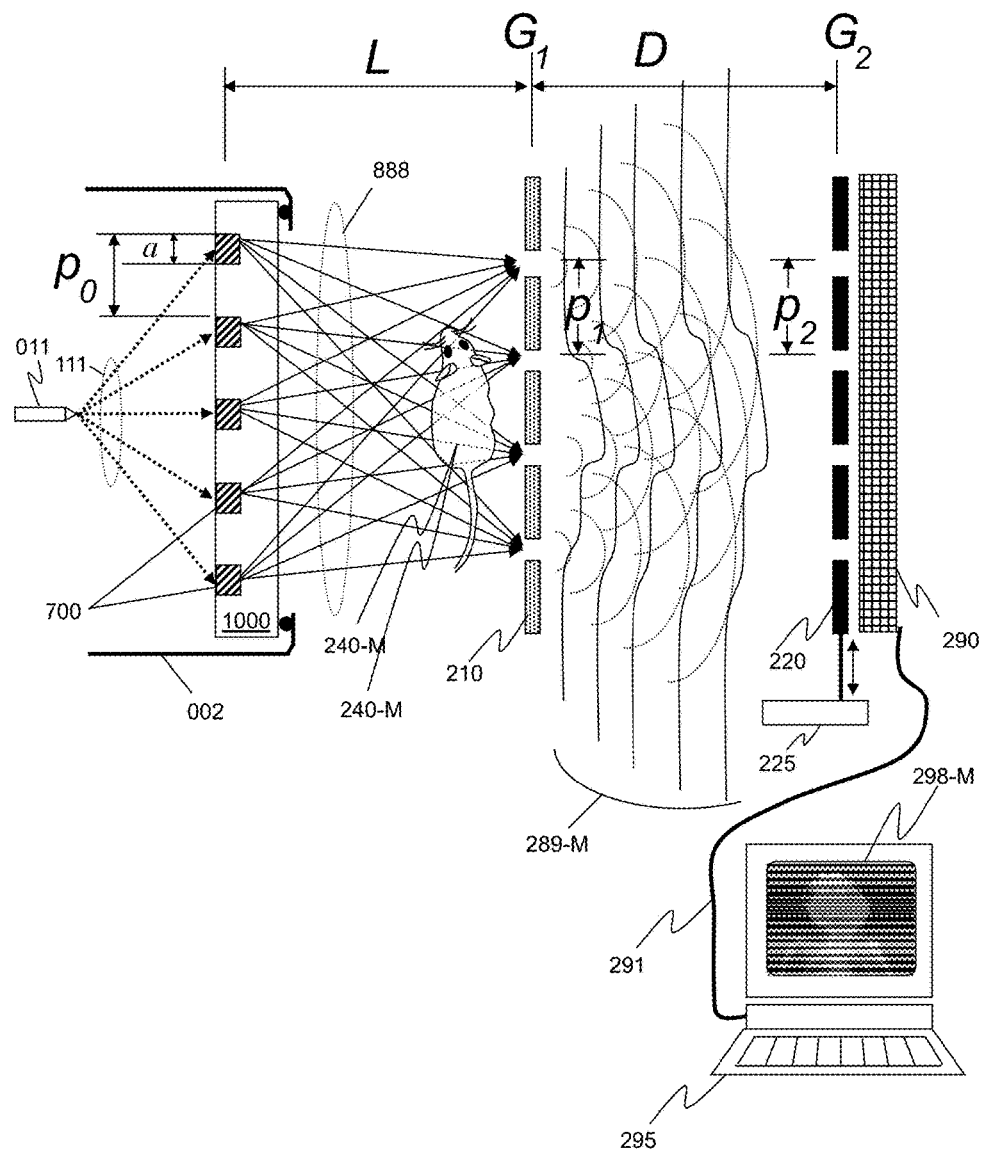
FIG. 12 illustrates a detailed schematic cross-section view of the embodiment of the invention shown in FIGS. 10 and 11.

FIGS. 10, 11 and 12 show a more detailed illustration of one embodiment of the invention, in which the array of sub-sources are formed using microstructures of x-ray generating material embedded in a thermally conducting substrate. In this embodiment, an x-ray source 008 illuminates an object 240-M and a beam-splitting grating $G_1$ 210, and the interference pattern they form is detected by a detector 290.

For the x-ray source 008, a high voltage power supply 010 provides electrons through a lead 021 to an electron emitter 011 in a vacuum chamber 002 held to a shielding housing 005 by supports 003. The electron emitter 011 emits electrons 111 towards a target 100. The target 100 comprises a substrate 1000 and a region that comprises a periodic array of discrete microstructures 700 comprising x-ray generating material (typically a high Z metallic material such as copper, molybdenum or tungsten) positioned on or embedded or buried in the substrate (typically a low Z material such as beryllium, diamond, silicon carbide). The discrete microstructures 700 may be any number of sizes or shapes, but are generally designed to be periodic arrays of right rectangular prisms with lateral dimensions on the order of microns in size in at least one dimension, such that the emission from each microstructure acts as a sub-source of x-rays with a spatial coherence length that is comparable to or larger than the grating period $p_1$ at the beam splitting grating $G_1$ 210. Additionally, the microstructures are preferably of a thickness (as typically measured orthogonal to the target surface) that is on the order of one half of the electron penetration depth within the substrate material.

The period $p_0$ of the microstructures 700 that form the x-ray sub-sources is related to the other geometric parameters in the system by:

$$p_0 = p_2 \frac{L}{D} \quad [\text{Eqn. 4}]$$

where L is the distance from the x-ray sub-sources 700 to the grating $G_1$ 210, and D is the distance from the grating $G_1$ to the detector/analyzer grating $G_2$ 220 with period $p_2$. In some embodiments, D will be set to be one of the fractional Talbot distances with interference fringes of high contrast (visibility), defined by:

$$\text{Contrast} = \frac{I_{max} - I_{min}}{I_{max} + I_{min}} \quad [\text{Eqn. 5}]$$

where $I_{max}$ and $I_{min}$ is the intensity peak and valley of the Talbot interference fringes without an object in the beam path, respectively.

For plane wave illumination (i.e. equivalent to the x-ray source being located at infinity) of a beam-splitting grating with a π phase-shift, the distance D is preferably given by:

$$D = D_N = N \frac{p_1^2}{8\lambda} = \frac{N}{16} D_T \quad [\text{Eqn. 6}]$$

where $D_N$ is the fractional Talbot distance for a plane wave illumination, λ is the mean x-ray wavelength, and N is referred to as a Talbot fractional order. The preferred value of D is dependent on the attenuating or phase shifting properties of the beam-splitting grating $G_1$, the line-space ratio of the beam-splitting grating $G_1$, and the source-to-grating distance L. For a π phase-shifting grating with a line-to-space ratio of 1:1, an odd integer fractional Talbot order N (N=1, 3, 5 . . . ) is preferred for determining the distance D. For an x-ray source located at a finite distance (e.g. L not infinity), D is increased to:

$$D = \frac{L \times D_N}{L - D_N} \quad [\text{Eqn. 7}]$$

The Talbot fringe period $p_f$ for a given fractional order is given by:

$$p_f = K\, p_1 \frac{L+D}{L} \quad [\text{Eqn. 8}]$$

where K is a parameter dependent on the attenuating or phase shifting properties of the beam-splitting grating $G_1$. K equals 0.5 when the beam-splitting grating is a π phase-shift grating, and equals 1 when the beam splitting grating is a π/2 phase shift grating.

Likewise, the Talbot fringe contrast is improved if a smaller x-ray sub-source size (i.e. more spatially coherent x-rays) is used, and in which the pitch $p_1$ used for the beam splitting grating $G_1$ is related to the size of the sub-source a and the distance L between them, satisfying the following requirement:

$$p_1 < \frac{\lambda L}{a} \quad [\text{Eqn. 9}]$$

where λ is a predetermined x-ray wavelength that will generally correspond to the wavelength of the monochromatic x-rays produced by the corresponding sub-source, or the mean x-ray wavelength for an x-ray sub-source with a broader spectrum.

In the vacuum chamber 002, electrons 111 bombard the target, and generate heat and x-rays 888 in the microstructures 700. The material in the substrate 1000 is selected such that it has relatively low energy deposition rate for electrons in comparison to the microstructures of the x-ray generating material, typically by selecting a low Z material for the substrate, and therefore will not generate a significant amount of heat and x-rays. The substrate 1000 material may also be chosen to have a high thermal conductivity, typically larger than 100 W/(m °C.). The microstructures of the x-ray generating material are also typically embedded within the substrate, i.e. if the microstructures are shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

The microstructures are typically connected electrically with a lead 022 to the positive terminal of the high voltage source 010 to allow the target to serve as an anode in the electrical system. Alternatively, the target may be grounded while the cathode (electron emitter) is of negative charge, or the target may be connected to a positive terminal while the cathode is grounded, so long as the anode is of relative higher voltage than the cathode. Additionally, in some embodiments, electron optics such as electrostatic lenses or magnetic coils may be placed inside or outside of the vacuum chamber 002 around or near the path of electrons 111 to further direct and focus the electron beam.

The target 100 as illustrated may additionally serve as a window in the vacuum chamber 002 so that the x-ray generating material is facing the interior of the vacuum chamber and the electron source, but x-rays 888 are also propagate through the back side of the target 100 towards the beam-splitting grating $G_1$ 210. In other embodiments, a separate window is used, and additional x-ray filters may also be used Once generated by the source 008, the x-rays 888 may pass through an optional shutter 230, an x-ray spectral filter to obtain a desired spectral bandwidth with a desired wavelength, and an object 240-M to be investigated. The x-rays then diffract off the beam splitting grating $G_1$ 210, which may additionally be mounted on a substrate 211, and then fall on the analyzer grating $G_2$ 220, which may also be mounted on a substrate 221. The final interference pattern will be detected by an array detector 290 that provides electrical signals corresponding to the x-ray intensity through a connector 291 to an image processing system 295 for analysis.

In addition to the x-ray source and interference detection system, means to move the object 240-M and the various gratings relative to each other, to the detector, and to the source may be used. In FIG. 10, the image processing system 295 may also be connected through a network 231 to a means 245 of controlling a stage 244 that sets the position and angle of the object 240-M, to a means 215 of controlling a mount 214 that sets the position and angle of the beam splitting grating $G_1$ 210, and to a means 225 of controlling a mount 224 that sets the position and angle of the analyzer grating $G_2$ 220, as well as a possible connection to the shutter 230 or to a switch 013 for the high voltage supply 010 to allow the x-rays to be moved and modulated (such as being turned on and off). Software run by processors in the image processing system 295 may control the motion of the gratings $G_1$ 210, $G_2$ 220, the object 240-M, and also the x-ray exposure to allow the collection of the multiple images needed to obtain detailed amplitude, differential phase, phase-contrast, and scattering contrast images of the object 240-M.

Additional embodiments may also include controls that allow the electron beam to be moved or modulated. For example, embodiments may be designed that additionally comprise a means of translating the x-ray source anode relative to the analyzer grating $G_2$. Additional embodiments that also allow the position and angle of the x-ray detector 290 to be adjusted may also be designed.

Figure 13:
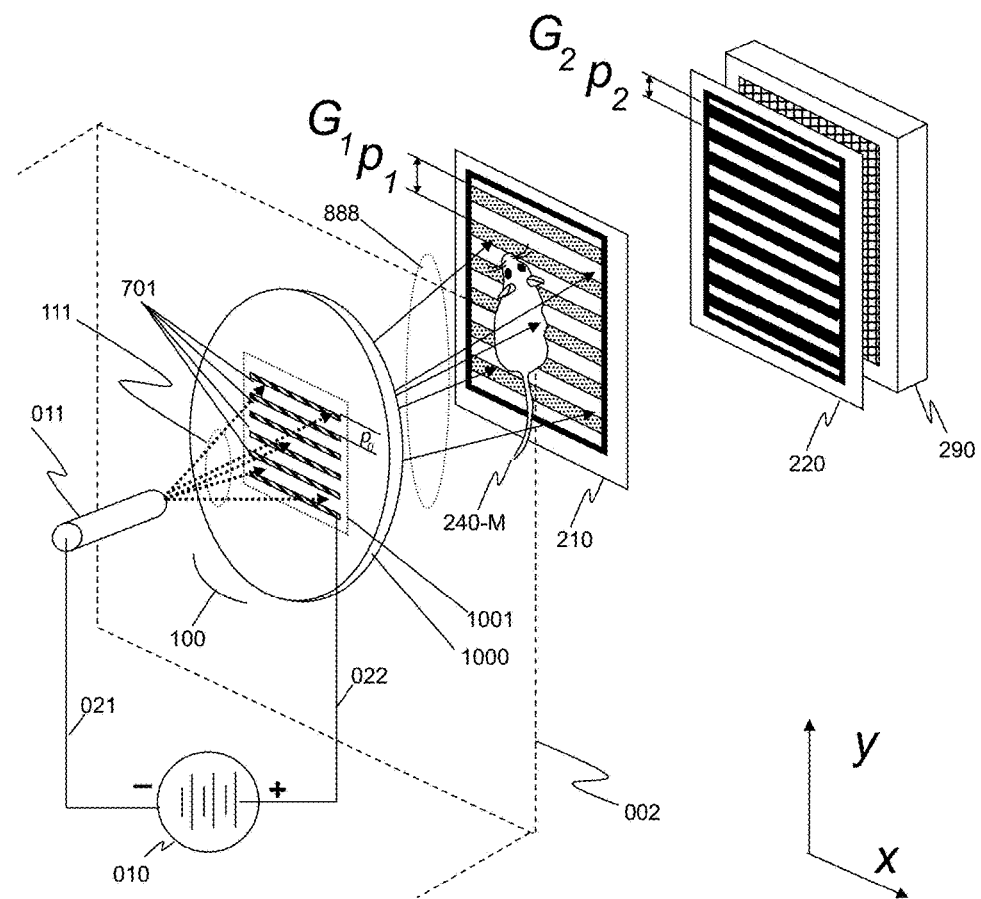
FIG. 13 illustrates a perspective view of an embodiment of the invention in which the x-ray target comprises of x-ray generating microstructures in the form of parallel lines.

FIG. 13 illustrates an embodiment of the invention in which the target 100 comprises a substrate 1000 and a plurality of microstructured line sources 701. These microstructured line sub-sources 701 will typically be a few microns wide in one direction (corresponding to the sub-source size parameter a, generally in the dimension orthogonal to the direction of the lines of the gratings $G_1$ 210 and $G_2$ 220, which corresponds to the y-direction in FIG. 13) but much longer (e.g. up to 1000 microns) in the direction parallel to the lines (which corresponds to the x-direction in FIG. 13). The pitch of the microstructures 701 as sub-sources as shown in FIG. 13 is $p_0$, and is related to the pitch of the analyzer/detector by Equation 4.

Figure 14:
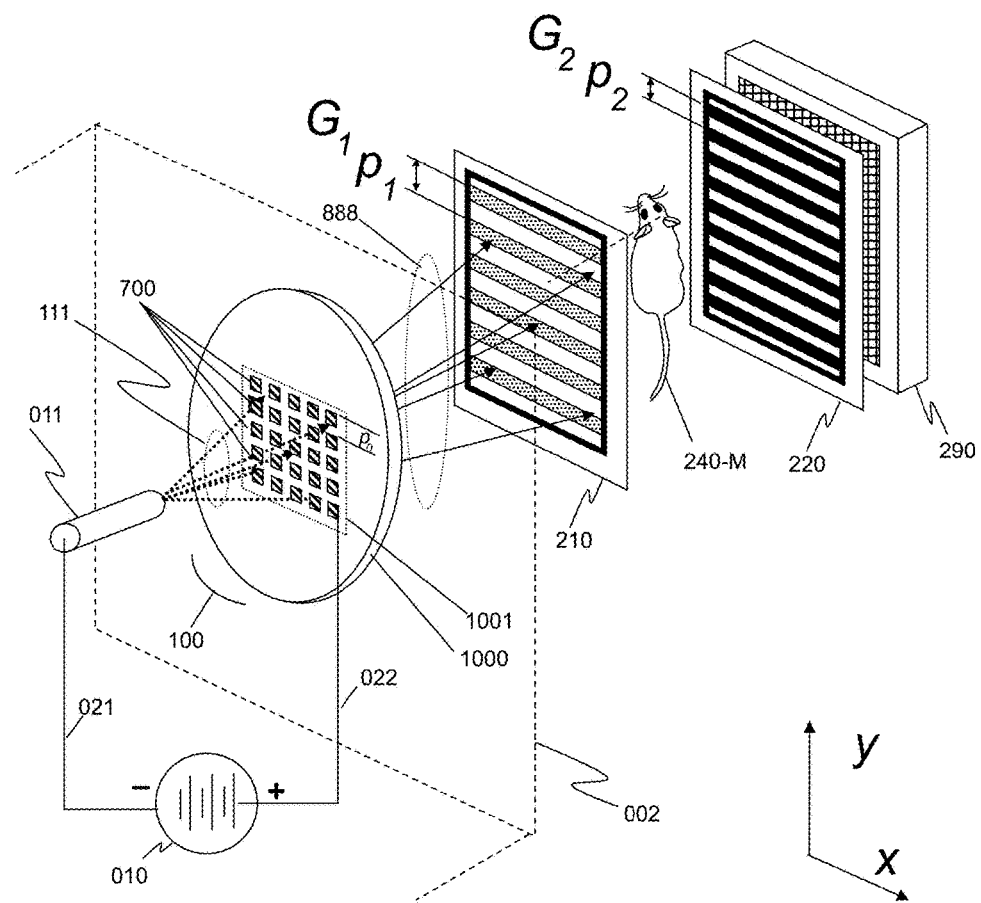
FIG. 14 illustrates a perspective view of an embodiment of the invention in which the object (a mouse) is placed between the gratings $G_1$ and $G_2$.

FIG. 14 illustrates an embodiment of the invention in which the object 240-M to be examined is placed between the gratings $G_1$ 210 and the detector 290. The microstructures 700 of x-ray generating material on the target as illustrated in FIG. 14 comprise sub-sources arranged in a 2-D periodic array in two orthogonal directions, but may be any periodic array that satisfies the coherence illumination condition of the beam-splitting grating $G_1$ 210, including a grid, a mesh, a checkerboard, or other periodic structures.

If the gratings comprise one-dimensional structures, the microstructures 700 in the source target 100 need only be periodic in the same direction as the 1-D arrays of $G_1$ 210 and $G_2$ 220 (i.e. the lines of microstructures 701 are ideally parallel to the lines of the gratings) but can have arbitrary or non-periodic structure in the perpendicular direction.

Figure 15:
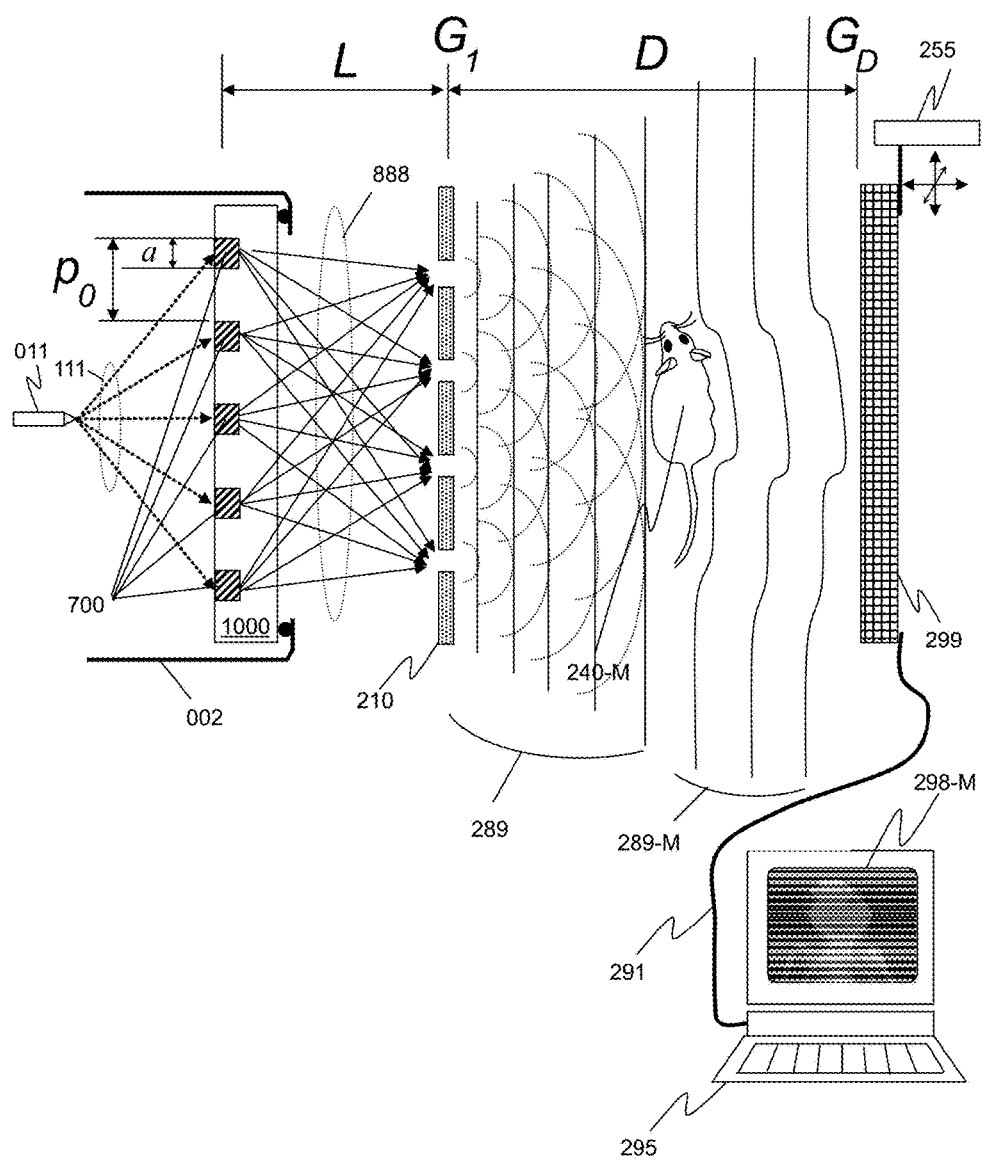
FIG. 15 illustrates a detailed schematic cross-section view of an embodiment of the invention in which a high-resolution detector is used without an analyzer grating.

FIG. 15 additionally illustrates an embodiment of the invention in which the there is no analyzer grating $G_2$ 220, but instead the detector 299 has a high resolution array $G_D$ with a pixel resolution equal to or better than one third ($\frac{1}{3}$) of the Talbot fringe period in the direction orthogonal to the grating lines. With this resolution, a single exposure image may be processed to obtain absorption, phase, and scattering contrast images simultaneously. This can be advantageous in that the intensity loss of 50% or more that typically occurs for x-rays passing through $G_2$ 220 is avoided, and the signal reaching the detector and therefore the signal-to-noise ratio is substantially higher.

In order to collect the multiple images for the calculation of detailed amplitude, differential phase, phase-contrast, and scattering contrast images for an object 240-M, the embodiment of FIG. 15 may additionally comprise a means 255 for translating the detector 290, not only in the two lateral directions parallel to the plane of the grating $G_1$, but also in direction defined along the path of x-ray propagation, to ensure that the detector 299 is placed at the correct multiple of the Talbot distance $T_D$.

Figure 16:
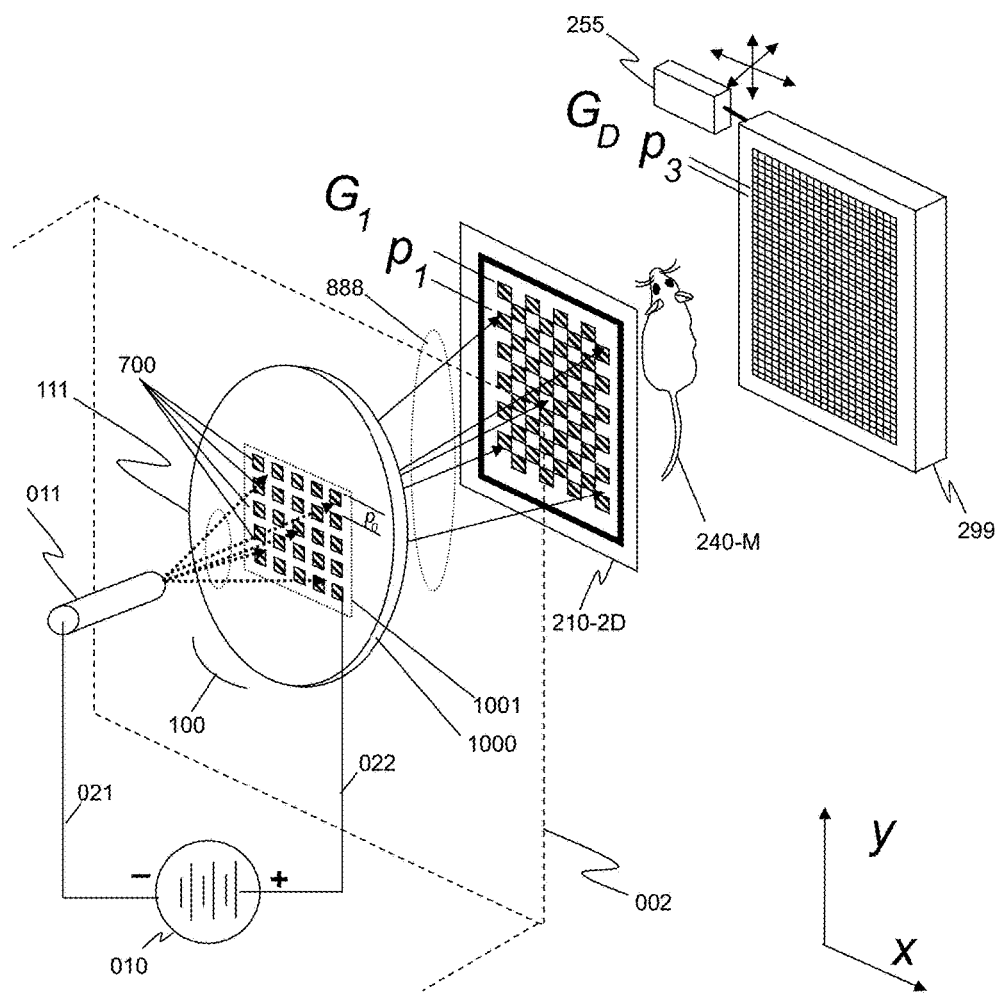
FIG. 16 illustrates a perspective view of an embodiment of the invention in which the object (a mouse) is placed between the grating $G_1$ and the detector, and the grating $G_1$ comprises a two-dimensional phase structure.

FIG. 16 illustrates an embodiment of the invention in which the beam splitting grating $G_1$ 210-2D comprises a two-dimensional periodic array, which may be either a transmission or a phase grating. When using a 2-D beam-splitting grating of this type, the patterns may be arranged in any one of a number of periodic patterns, including a mesh, a checkerboard, a circular 2-D array, or other periodic arrays.

FIG. 16 illustrates the use of a 2-D beam splitting grating $G_1$ 210-2D in conjunction with a high-resolution detector 299, as was also shown in FIG. 15. To simultaneously obtain a differential phase contrast, phase contrast, absorption, scattering contrast images in two orthogonal directions, the geometric parameters, including the x-ray sub-source size a, the period $p_1$ of the grating $G_1$ 210-2D and the distance L, need to satisfy the coherence illumination condition of the grating $G_1$ in both directions. As before, the detector 299 has spatial resolution equal to or better than $\frac{1}{3}$ of the Talbot fringe period in the two orthogonal directions in the image plane and is positioned to be aligned with the Talbot fringe pattern.

Such embodiments with 2-D patterns on the beam splitting grating $G_1$ 210-2D may also be used with the previously described lower resolution detector 290 in conjunction with a two-dimensional analyzer grating $G_2$ which may be phase stepped in two directions in any sequence so that the phase information is obtained in both orthogonal directions. Similar to the description of $G_1$ 210-2D above, this 2-D analyzer grating $G_2$ may be of any periodic structure such as a mesh, a checkerboard, or 2-D array of structures such as circles, triangles, squares, rectangles, etc.

Figure 17:
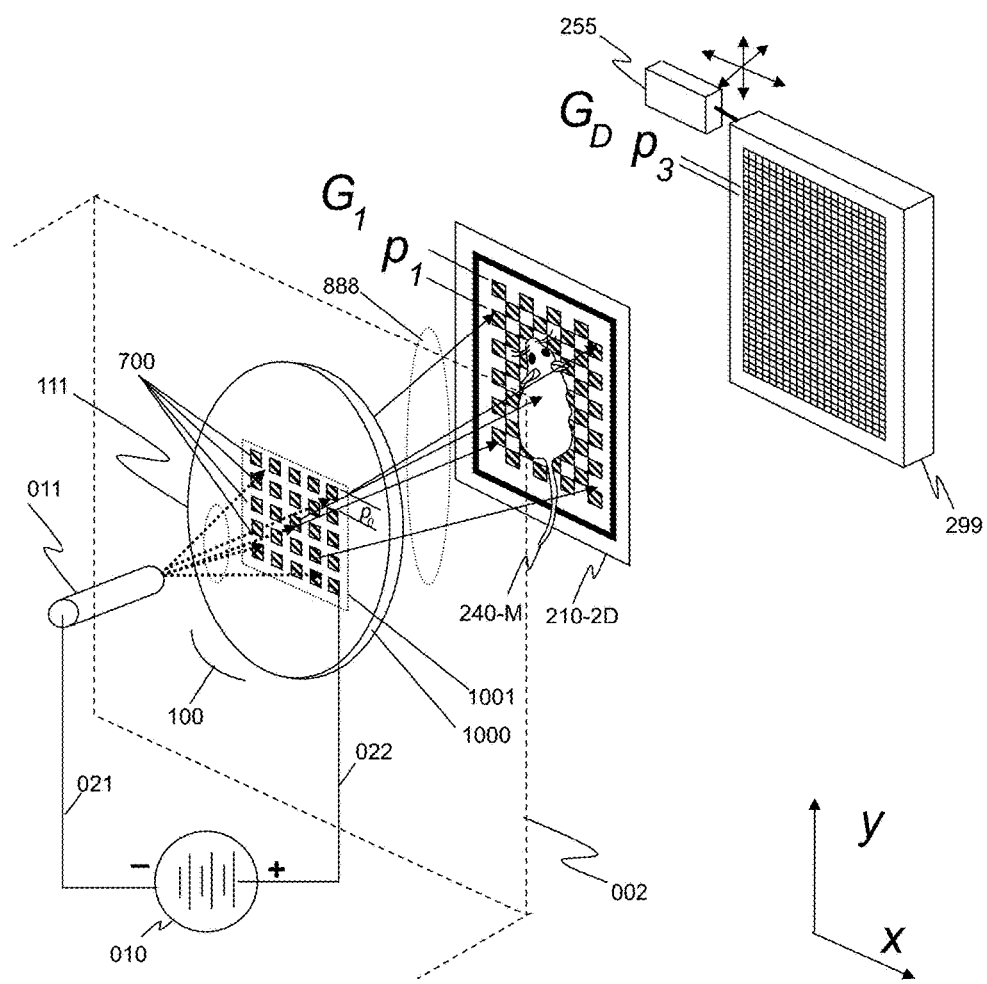
FIG. 17 illustrates a perspective view of an embodiment of the invention in which the object (a mouse) is placed between the source and the grating $G_1$, and the grating $G_1$ comprises a two-dimensional phase structure.

FIG. 17 represents an embodiment similar to FIG. 16, except that the object 240-M under examination is now placed between the x-ray source and the beam-splitting grating 210-2D.

Note that some of the embodiments are one-dimensional Talbot-Yun interferometers in which absorption, phase, and scattering information is obtained in one direction and incorporate one or more 1-D gratings in combination with a micro structured source target that is periodic in at least in the direction perpendicular to the grating line direction (but may be periodic in other directions as well). Other embodiments are two-dimensional Talbot-ST interferometers in which absorption, phase, and scattering information is obtained in two orthogonal directions (or all three dimensions by performing computed tomography using the 2-D Talbot-Yun setup).

Figure 18:
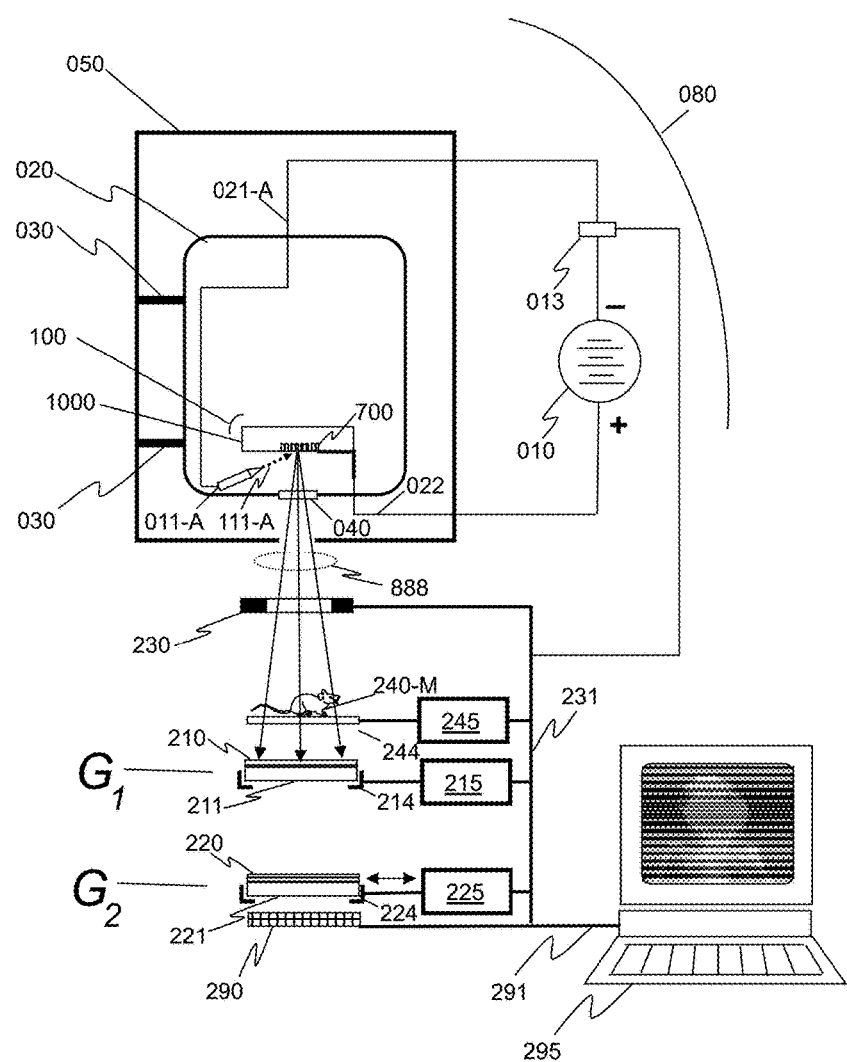
FIG. 18 illustrates a schematic cross-section view of an embodiment of the invention in which the target is mounted within the vacuum chamber.
Figure 19:
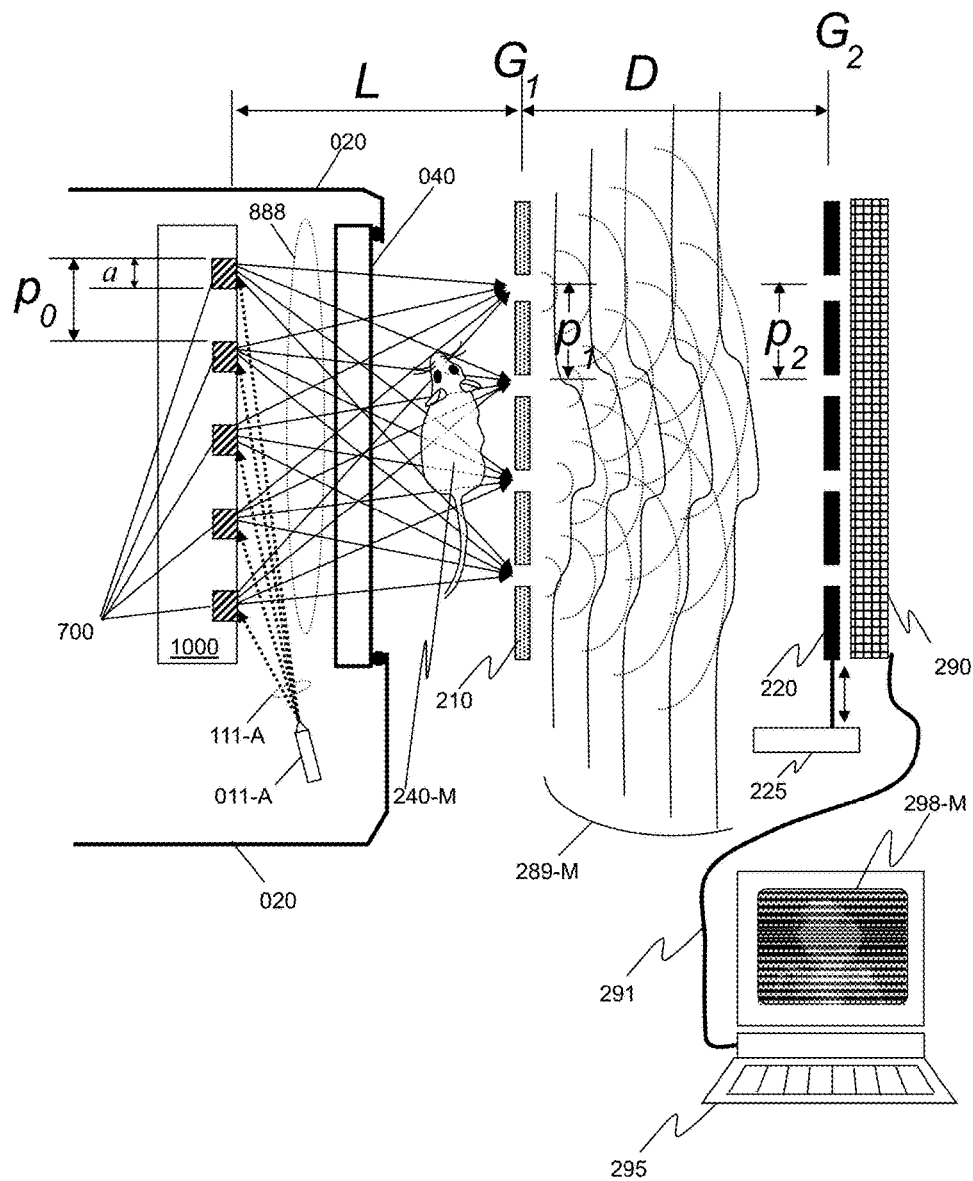
FIG. 19 illustrates a detailed schematic cross-section view of the embodiment of the invention shown in FIG. 18.

FIGS. 18 and 19 illustrate another embodiment of the invention in which the x-ray source 080 comprises a vacuum chamber 020 supported on mounts 030 within an x-ray shielding housing 050. The source 080 also comprises a target 100 comprising a substrate 1000 and a periodic pattern comprising x-ray sub-sources 700 mounted entirely within the vacuum chamber 020. As before, this embodiment also comprises a high voltage source 010, which has a negative terminal connected through a lead 021-A to an electron emitter 011-A, while the positive terminal is connected through one or more leads 022 to the microstructures in the target, allowing them to serve as an anode.

However, in this embodiment, the surface of the target 100 comprising the periodic array of x-ray sub-sources 700 comprising of x-ray generating material is facing a window 040 mounted in the wall of the vacuum chamber 020, and the electron emitter 011-A is aligned to emit a beam of electrons 111-A onto the surface of the target 100 comprising sub-sources 700 facing the window 040.

Figure 20:
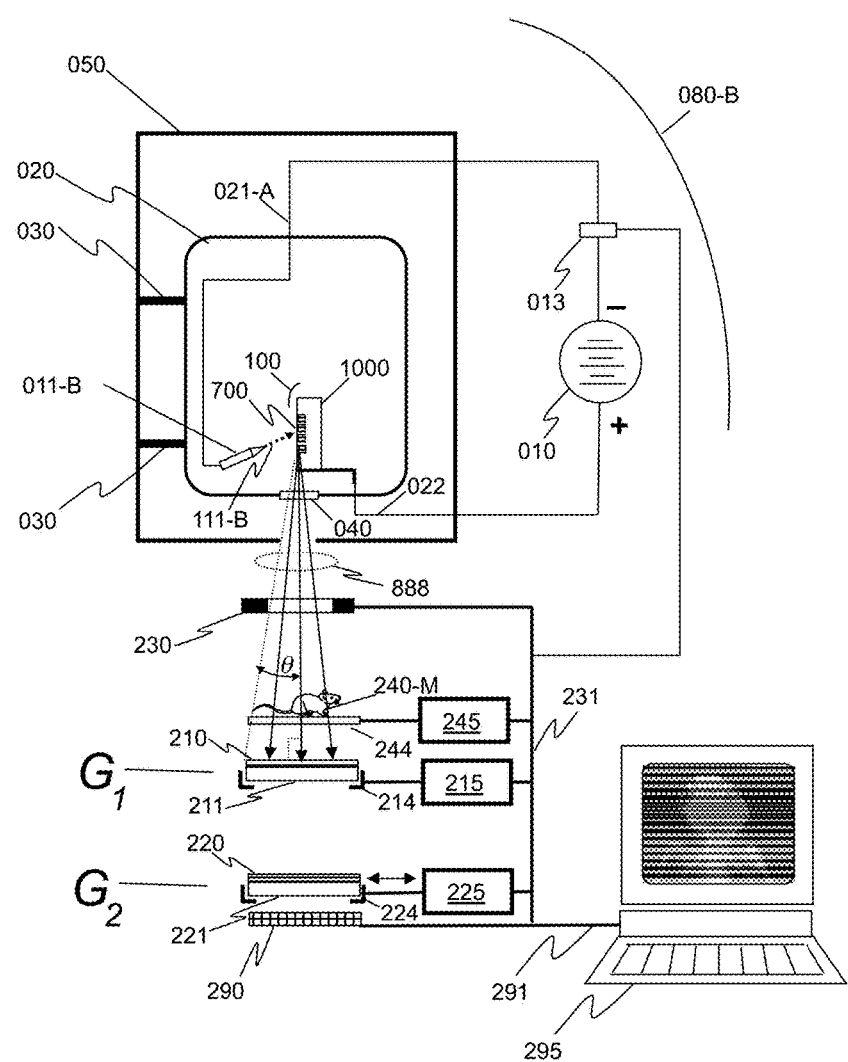
FIG. 20 illustrates a schematic cross-section view of an embodiment of the invention in which the target is mounted within the vacuum chamber and x-rays are generated using linear accumulation.
Figure 21:
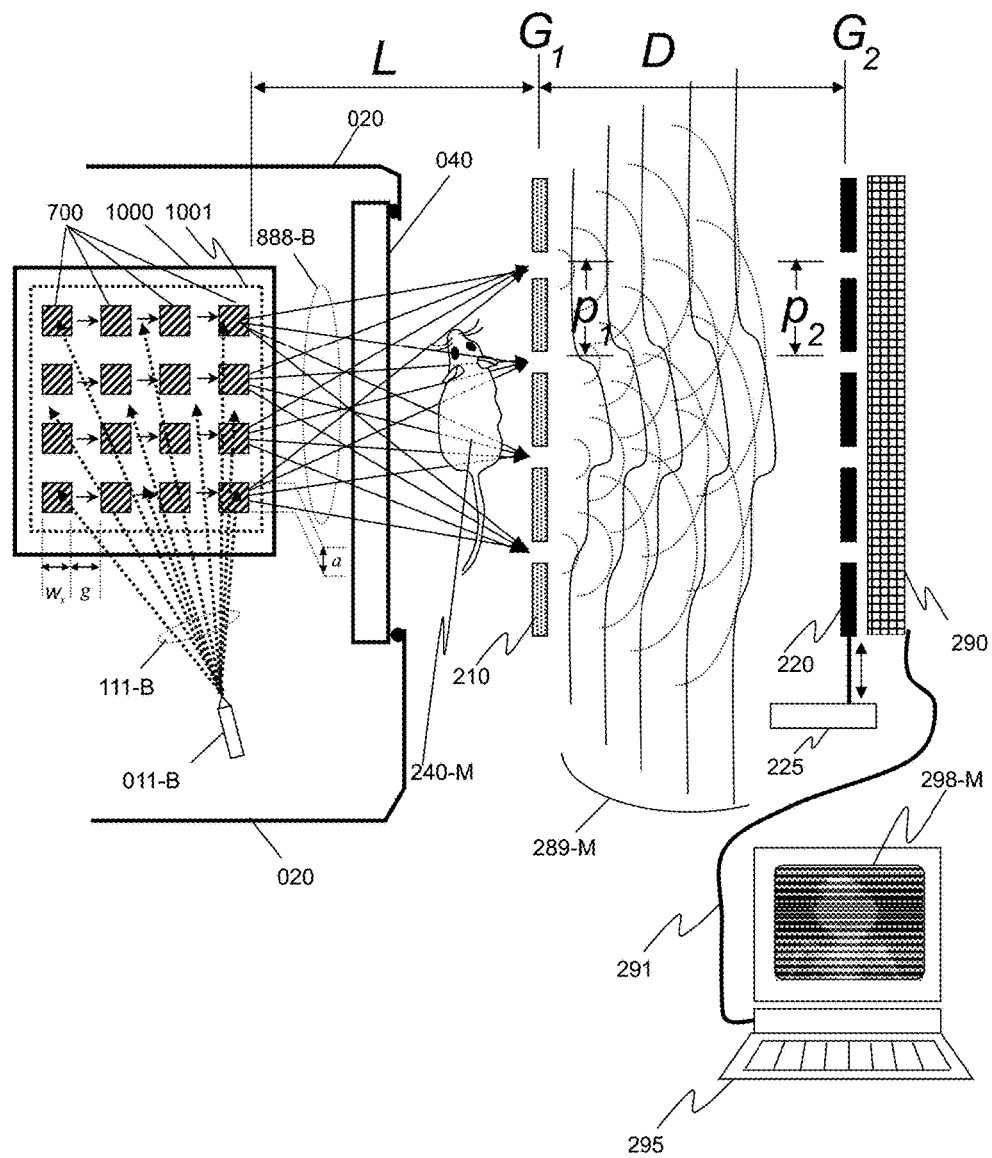
FIG. 21 illustrates a detailed schematic cross-section view of the embodiment of the invention shown in FIG. 20.

FIGS. 20 and 21 illustrate another embodiment of the invention in which the target 100 comprising a substrate 1000 and a periodic pattern comprising x-ray sub-sources 700 mounted entirely within the vacuum chamber 020. As before, this embodiment also comprises a high voltage source 010, which has a negative terminal connected through a lead 021-B to an electron emitter 011-B, while the positive terminal is connected through one or more leads 022 to the microstructures in the target, allowing them to serve as an anode.

However, in this embodiment, the surface of the target 100 comprising the periodic array of x-ray sub-sources 700 comprising x-ray generating material is oriented such that x-rays produced by some of the microstructures propagate towards other microstructures that are also producing x-rays, and a linear accumulation of x-rays 888-B from a plurality of microstructures 700 emerges from the target. The distance g between the microstructures and microstructures 700 emerges from the target. The distance g between the microstructures and the width $w_x$ in the propagation direction should be small enough such that the emission from the nth microstructure contributing to the accumulated x-rays can be considered as a single sub-source with dimension a of Eqn. 9, i.e.:

$$a \geq \tan \theta \cdot (n(g+w_x))  \quad \text{[Eqn. 10]}$$

where a is the sub-source dimension that meets the coherence requirements of the system, and $\theta$ is one half of the field-of-view angle for the system.

Linear accumulation of x-ray sources as used in this embodiment of the invention is described more fully in the co-pending U.S. Patent Application entitled X-RAY SOURCES USING LINEAR ACCUMULATION by the inventors of the present invention (U.S. patent application Ser. No. 14/490,672 filed Sep. 19, 2014), which is hereby incorporated by reference in its entirety. Any of the source designs and configurations disclosed in the above referenced co-pending Application may be considered for use as a component in any or all of the interferometric imaging systems disclosed herein.

Figure 22:
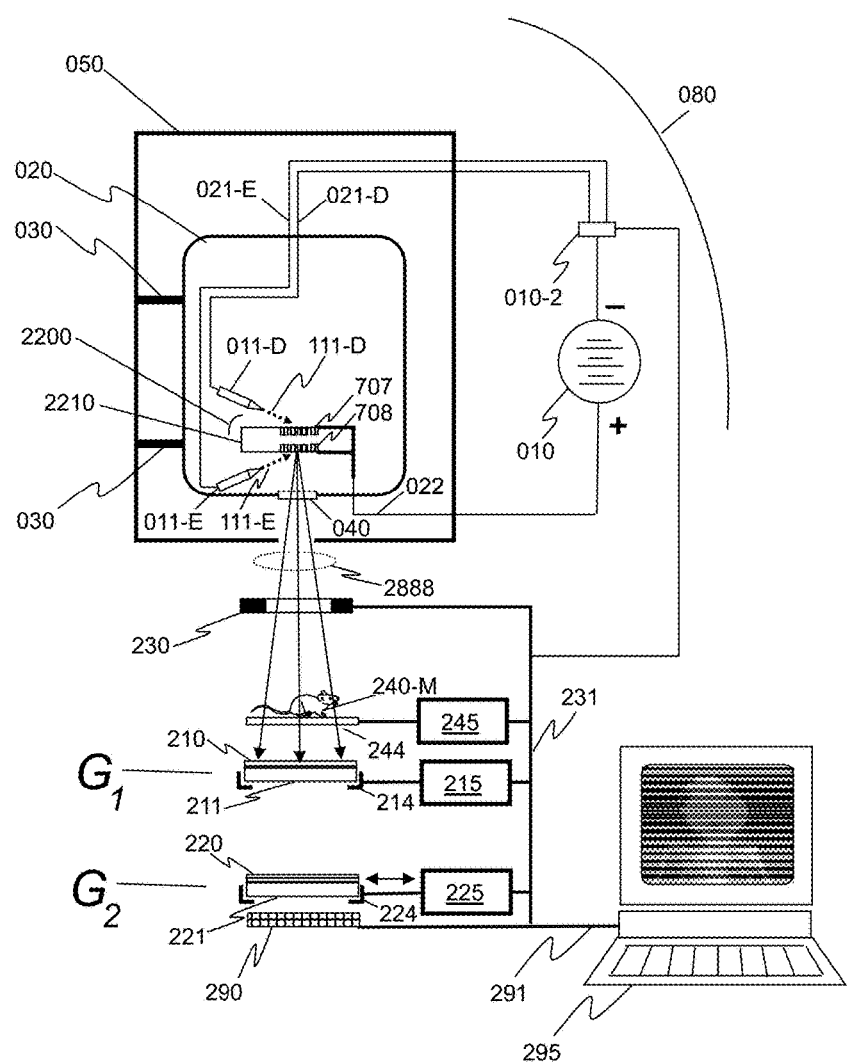
FIG. 22 illustrates a schematic cross-section view of an embodiment of the invention in which two electron beams bombard the target from both sides.
Figure 23:
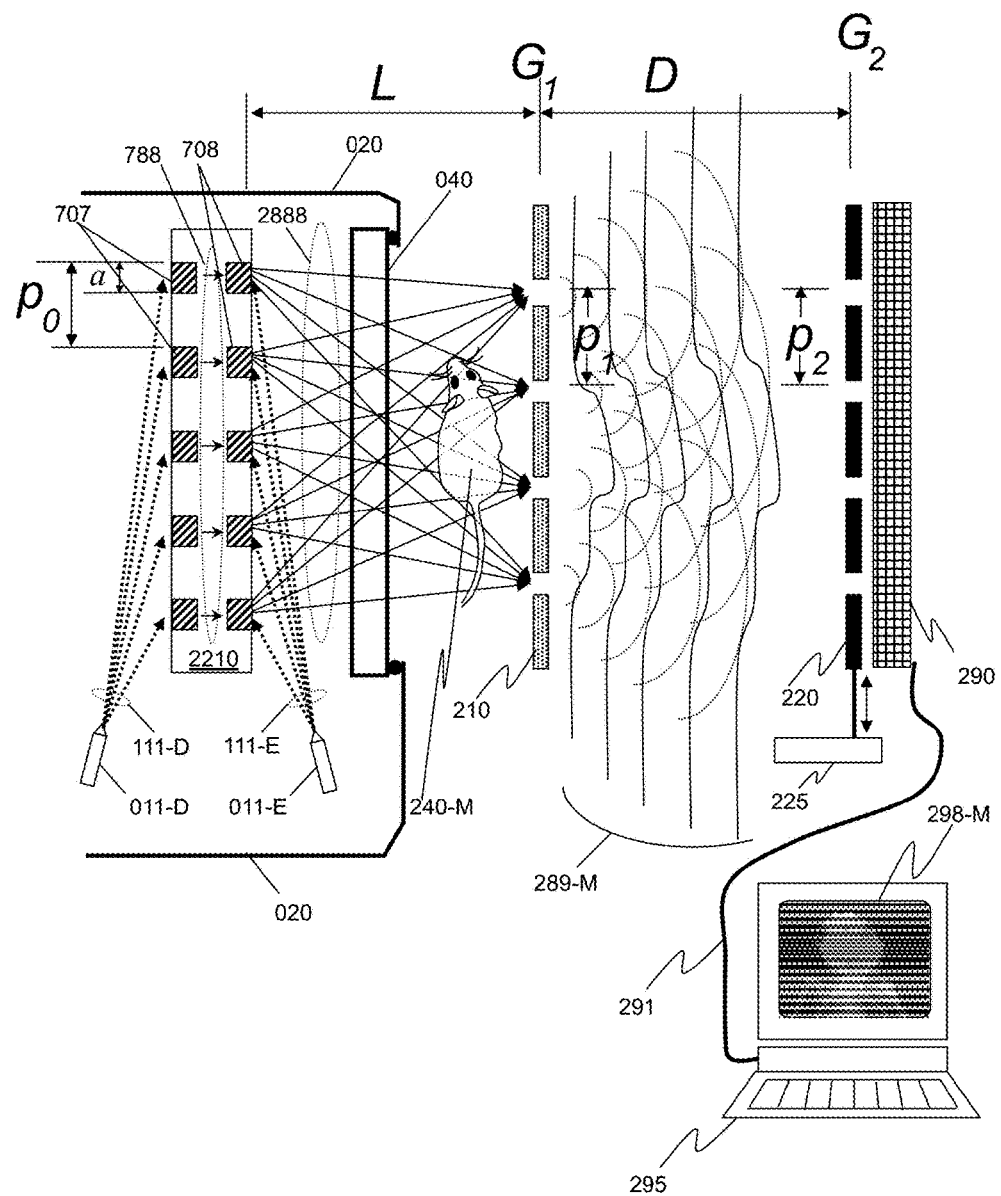
FIG. 23 illustrates a detailed schematic cross-section view of the embodiment of the invention shown in FIG. 22.

Likewise, FIGS. 22 and 23 illustrate another embodiment of the invention that utilizes linear accumulation of x-rays. In this embodiment, the x-ray source 080 includes a target 2200 comprising a substrate 2210 and a first set of sub-sources 707 and a second set of sub-sources 708 mounted entirely within the vacuum chamber 020. As before, this embodiment also comprises a high voltage source 010, but this high voltage source is connected to a junction 010-2 that provides high voltage to two electron emitters 011-D and 011-E through a leads 021-D and 021-E, respectively. As shown in FIGS. 22 and 23, the first electron emitter 021-D provides an electron beam 111-D that bombards the first set of sub-sources 707, while the second electron emitter 021-E provides an electron beam 111-E that bombards the second set of sub-sources 708. Some of the x-rays 788 generated by the first set of sub-sources 707 and the second set of sub-sources 708 along the x-ray imaging beam axis combine to produce x-rays 2888 from the target 2200 will be augmented by the linear accumulation of x-rays from these two sets of x-ray sub-sources.

It will also be known to those skilled in the art that other embodiments of the invention comprising an x-ray source in which the target/anode under bombardment by electrons is moved, translated, or rotated to distribute the heat load are also possible.

Note: The illustrations of FIGS. 10 through 23 are not shown to scale, and are meant to illustrate the principle of the invention and not specific relationships between the microstructures 700, the target 100 and the various grating periods $p_1$ and $p_2$. The microstructures 700, 701, 707, 708 etc. may be on the order of microns in size, while the object under examination 240-M may be centimeters in size. Likewise, although these are illustrated in which an object with dimensions on the order of centimeters (a mouse) is shown, the techniques described are not limited to such objects, but may be used to examine even larger structures, or microscopic structures as well, as long as a suitable resolution for the detector and other elements of the interferometer are suitably constructed.

2. Fabrication of X-Ray Targets

Targets such as those to be used in x-ray sources according to the invention disclosed herein have been described in detail in the co-pending U.S. Patent Application entitled STRUCTURED TARGETS FOR X-RAY GENERATION by the inventors of the present invention (U.S. patent application Ser. No. 14/465,816, filed Aug. 21, 2014), which is hereby incorporated by reference in its entirety. Any of the target designs and configurations disclosed in the above referenced co-pending Application may be considered for use as a component in any or all of the x-ray sources disclosed herein.

As described herein and in the above cited pending Patent Applications, the target used in the source of x-rays may comprise a periodic array of sub-sources. Each sub-source may be comprised of a single or multiple microstructures of x-ray generating material in thermal contact with, or preferably embedded in, a substrate selected for its thermal conductivity. When the microstructures are in good thermal contact with a substrate having a high thermal conductivity, higher electron current densities may be used to generate x-rays, since the excess heat will be drawn away into the substrate. The higher current densities will give rise to higher x-ray flux, leading to a higher brightness source. As described in the above co-pending patent Applications, sources with microstructures of x-ray generating material may have a brightness more than 10 times larger than simpler constructions made from the same materials. Additional configurations in which multiple sub-sources are aligned to contribute x-rays on the same axis can multiply the brightness further through linear accumulation of the x-ray sub-sources.

It should also be noted here that, when the word "microstructure" is used herein, it is specifically referring to microstructures comprising x-ray generating material. Other structures, such as the cavities used to form the x-ray microstructures, have dimensions of the same order of magnitude, and might also be considered "microstructures". As used herein, however, other words, such as "structures", "cavities", "holes", "apertures", etc. may be used for these structures when they are formed in materials, such as the substrate, that are not selected for their x-ray generating properties. The word "microstructure" will be reserved for structures comprising materials selected for their x-ray generating properties.

Likewise, it should be noted that, although the word "microstructure" is used, x-ray generating structures with dimensions smaller than 1 micron, or even as small as nano-scale dimensions (i.e. greater than 10 nm) may also be described by the word "microstructures" as used herein as long as the properties are consistent with the geometric factors for sub-source size and grating pitches set forth in the various embodiments.

It should also be noted that here that, when the word "sub-source" is used it may refer to a single microstructure of x-ray generating material, or an ensemble of smaller microstructures that function similarly to a single structure for the purposes of Talbot interferometry.

The fabrication of these microstructured targets may follow well known processing steps used for the creation of embedded structures in substrates. If the substrate is a material with high thermal conductivity such as diamond, conventional lithographic patterning using photoresists can produce micron sized structures, which may then be etched into the substrate using processes such as reactive ion etching (RIE). Deposition of the x-ray generating material into the etched structures formed in the substrate may then be carried out using standard deposition processes, such as electroplating, chemical vapor deposition (CVD), or atomic layer deposition.

The x-ray generating material used in the target should ideally have good thermal properties, such as a high melting point and high thermal conductivity, in order to allow higher electron power loading on the source to increase x-ray production. The x-ray generating material should additionally be selected for good x-ray production properties, which includes x-ray production efficiency (proportional to its atomic number) and in some cases, it may be desirable to produce a specific spectra of interest, such as a characteristic x-ray spectral line. For these reasons, targets are often fabricated using tungsten, with an atomic number Z=74.

Table I lists several materials that are commonly used for x-ray targets, several additional potential target materials (notably useful for specific characteristic lines of interest), and some materials that may be used as substrates for target materials. Melting points, and thermal and electrical conductivities are presented for values near 300° K (27° C.). Most values are cited from the *CRC Handbook of Chemistry and Physics*, 90th ed. [CRC Press, Boca Raton, Fla., 2009]. Other values are cited from various sources found on the Internet. Note that, for some materials, such as sapphire for example, thermal conductivities an order of magnitude larger may be possible when cooled to temperatures below that of liquid nitrogen (77° K) [see, for example, Section 2.1.5, Thermal Properties, of E. R. Dobrovinskaya et al., *Sapphire: Material, Manufacturing, Applications*, Springer Science+Business Media, LLC, 2009].

Figure 24:
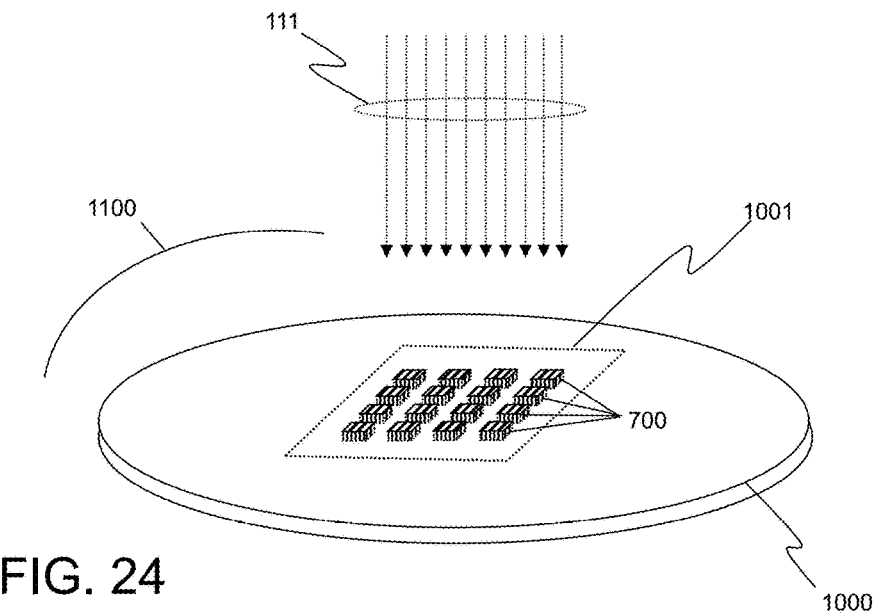
FIG. 24 illustrates a perspective view of a target comprising a grid of embedded rectangular target microstructures on a larger substrate that may be used in some embodiments of the invention.

FIG. 24 illustrates a target as may be used in some embodiments of the invention. In this figure, a substrate 1000 has a region 1001 that comprises an array of sub-sources 700 comprising microstructures of x-ray generating material (typically a metallic material), in which the sub-sources are arranged in a regular array of right rectangular prisms. In a vacuum, electrons 111 bombard the target from above, and generate heat and x-rays in the microstructures 700. The material in the substrate 1000 is selected such that it has relatively low x-ray production (efficiency is proportional to atomic number) and energy deposition rate (stopping power is proportional to density) for electrons in comparison to the x-ray generating microstructure material, and therefore will not generate a significant amount of heat and x-rays. This is typically achieved by selecting a low mass density and low atomic number (Z) material for the substrate.

TABLE I

Various Target and Substrate Materials and Selected Properties.

| Material (Elemental Symbol) | Atomic Number Z | Melting Point ° C. (1 atm) | Thermal Conductivity (W/(m ° C.)) | Electrical Conductivity (MS/m) |
|---|---|---|---|---|
| Common Target Materials: | | | | |
| Chromium (Cr) | 24 | 1907 | 93.7 | 7.9 |
| Iron (Fe) | 26 | 1538 | 80.2 | 10.0 |
| Cobalt (Co) | 27 | 1495 | 100 | 17.9 |
| Copper (Cu) | 29 | 1085 | 401 | 58.0 |
| Molybdenum (Mo) | 42 | 2623 | 138 | 18.1 |
| Silver (Ag) | 47 | 962 | 429 | 61.4 |
| Tungsten (W) | 74 | 3422 | 174 | 18.4 |
| Other Possible Target Materials: | | | | |
| Titanium (Ti) | 22 | 1668 | 21.9 | 2.6 |
| Gallium (Ga) | 35 | 30 | 40.6 | 7.4 |
| Rhodium (Rh) | 45 | 1964 | 150 | 23.3 |
| Indium (In) | 49 | 157 | 81.6 | 12.5 |
| Cesium (Cs) | 55 | 28 | 35.9 | 4.8 |
| Rhenium (Re) | 75 | 3185 | 47.9 | 5.8 |
| Gold (Au) | 79 | 1064 | 317 | 44.0 |
| Lead (Pb) | 82 | 327 | 35.3 | 4.7 |
| Other Potential Substrate Materials with low atomic number: | | | | |
| Beryllium (Be) | 4 | 1287 | 200 | 26.6 |
| Carbon (C): Diamond | 6 | * | 2300 | $10^{-19}$ |
| Carbon (C): Graphite $\parallel$ | 6 | * | 1950 | 0.25 |
| Carbon (C): Nanotube (SWNT) | 6 | * | 3180 | 100.0 |
| Carbon (C): Nanotube (bulk) | 6 | * | 200 | |
| Boron Nitride (BN) | B = 5 N = 7 | ** | 20 | $10^{-17}$ |
| Silicon (Si) | 14 | 1414 | 124 | $1.56 \times 10^{-9}$ |
| Silicon Carbide ($\beta$-SiC) | Si = 14 C = 6 | 2798 | 0.49 | $10^{-9}$ |
| Sapphire ($Al_2O_3$) $\parallel$ C | Al = 13 O = 8 | 2053 | 32.5 | $10^{-20}$ |

* Carbon does not melt at 1 atm; it sublimes at ~3600° C.
** BN does not melt at 1 atm; it sublimes at ~2973° C.

The substrate 1000 material may also be chosen to have a high thermal conductivity, typically larger than 100 W/(m ° C.), and the microstructures are typically embedded within the substrate, i.e. if the microstructures are shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

Note that the sub-source sizes and dimensions in some embodiments may be constrained by the same limitations as the periodicity $p_0$ of the grating $G_0$ in prior art. In other words, the spatial resolution achievable at the object position in the x-ray interferometric imaging systems as shown in FIGS. 9 through 23 is determined by the overall x-ray source size and the detector resolution, similar to the conditions described in the prior art interferometeric imaging systems, such as the Talbot-Lau system. Therefore, the maximum x-ray source size (width of each microstructure spot) is limited for a given detector resolution and a given imaging geometry as determined by the distance between the source and object and the distance between the object to the detector.

The line-to-space ratio of the arrays of sub-sources is a design parameter that should be considered in the design of any system. A large spatial coherence length is inversely proportional to the size of an x-ray source or sub-source. Because the fringe visibility of the Talbot interference fringes increases linearly with the relative ratio of the spatial coherence length of the illuminating x-ray beam to the period of the beam-splitting grating $p_1$ for a value of the ratio from 0.3 to 1, it is generally preferred to have a small source size. However, the x-ray production is inversely proportional to the area of the sub-source (e.g. a reduction in line width will lead to a decrease of x-ray production). Since the throughput of an imaging system is generally proportional to square of the contrast transfer function and only proportional to the x-ray flux, it is generally preferred to have a line-to-space ration less than 1:1. Some embodiments of the invention may use a line-to-space (i.e. x-ray generating material to substrate material) ratio between 1:5 and 1:2 (i.e. the relative area of the x-ray generating material may range from 20% to 33%).

A figure of merit (FOM) that may be helpful for the selection of materials for targets according to this invention is the ratio of x-rays produced by the microstructures to the x-rays produced by the electrons also bombarding the substrate. This figure of merit may be useful for the design of and selection of materials for the targets for the system, and should be taken into consideration in addition to the thermal conductivity of the substrate. As the electron energy deposition rate is proportional to the mass density and the x-ray production efficiency in a material is proportional to its atomic number, this figure of merit may be defined as follows:

$$FOM = \frac{Z_2 \times \rho_2}{Z_1 \times \rho_1} \qquad \text{[Eqn. 11]}$$

where Z is the atomic number and ρ is the density, and material 1 is the substrate and material 2 is the x-ray generating material.

A number of microstructures and substrate material combinations are listed below in Table II. Any of the following combinations may be used, but it is preferable that the materials are selected such that the FOM is greater than 12, and that the thermal conductivity of the substrate material is greater than 100 W/(m ° C.) at room temperature.

TABLE II

Figure of Merit for x-ray material/substrate combinations.

| Substrate material | | | Microstructure material | | | Figure of Merit $\frac{Z_2 \times \rho_2}{Z_1 \times \rho_1}$ |
|---|---|---|---|---|---|---|
| Material | Atomic # $Z_1$ | Mass density (g/cm³) | Material | Atomic # $Z_2$ | Mass density (g/cm³) | |
| SiC | 12.55 | 3.21 | Cu | 29 | 8.96 | 6 |
| Si | 14 | 2.33 | Cu | 29 | 8.96 | 8 |
| SiC | 12.55 | 3.21 | Mo | 42 | 10.2 | 11 |
| Diamond | 6 | 3.5 | Cu | 29 | 8.96 | 12 |
| Si | 14 | 2.33 | Mo | 42 | 10.2 | 13 |
| Diamond | 6 | 3.5 | Mo | 42 | 10.2 | 21 |
| SiC | 12.55 | 3.21 | W | 74 | 19.25 | 35 |
| Be | 4 | 1.85 | Cu | 29 | 8.96 | 35 |
| Si | 14 | 2.33 | W | 74 | 19.25 | 44 |
| Be | 4 | 1.85 | Mo | 42 | 10.2 | 59 |
| Diamond | 6 | 3.5 | W | 74 | 19.25 | 68 |
| Be | 4 | 1.85 | W | 74 | 19.25 | 193 |

Figure 25:
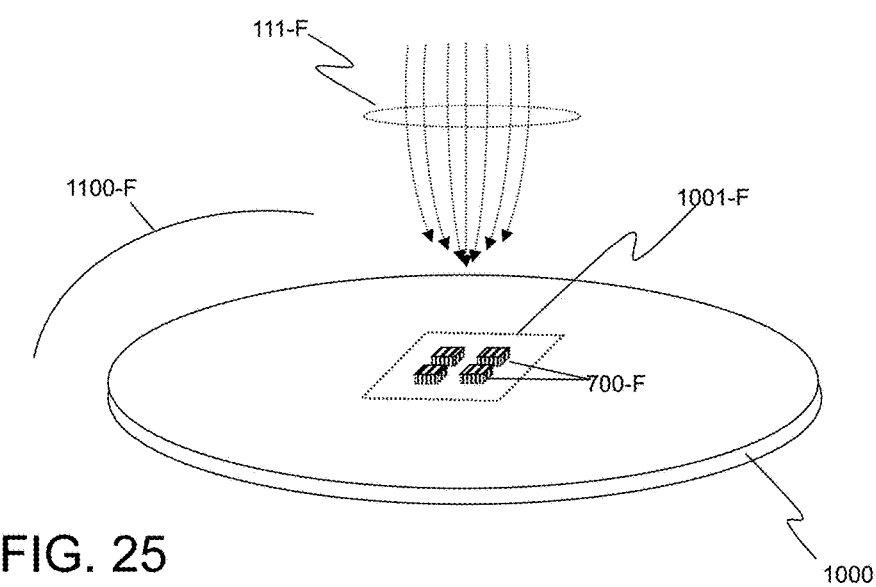
FIG. 25 illustrates a perspective view of a variation of a target comprising a grid of embedded rectangular target microstructures on a larger substrate for use with focused electron beam that may be used in some embodiments of the invention.

FIG. 25 illustrates another target as may be used in some embodiments of the invention in which the electron beam 111-F is directed by electrostatic lenses to form a more concentrated, focused spot. For this situation, the target 1100-F will still comprise a region 1001-F comprising an array of microstructures 700-F comprising x-ray material, but the size and dimensions of this region 1001-F can be matched to regions where electron exposure will occur. In these targets, the "tuning" of the source geometry and the x-ray generating material can be controlled such that the designs mostly limit the amount of heat generated to the microstructured region 1001-F, while also reducing the design and manufacturing complexity. This may be especially useful when used with electron beams focused to form a micro-spot, or by more intricate systems that form a more complex electron exposure pattern.

The depth of penetration of electrons into the material can be estimated by Pott's Law [P. J. Potts, Electron Probe Microanalysis, Ch. 10 of *A Handbook of Silicate Rock Analysis*, Springer Netherlands, 1987, p. 336)], which states that the penetration depth x in microns is related to the 10% of the value of the electron energy $E_0$ in keV raised to the 3/2 power, divided by the density of the material:

$$x(\mu m) = 0.1 \times \frac{E_0^{1.5}}{\rho} \qquad \text{[Eqn. 12]}$$

For less dense material, such as a diamond substrate, the penetration depth is much larger than for a material with greater density, such as most materials containing elements used for x-ray generation.

Using this formula, Table III illustrates some of the estimated penetration depths for some common x-ray target materials.

TABLE III

Estimates of penetration depth for 60 keV electrons into some materials.

| Material | Z | Density (g/cm$^3$) | Penetration Depth (μm) |
|---|---|---|---|
| Diamond | 6 | 3.5 | 13.28 |
| Copper | 29 | 8.96 | 5.19 |
| Molybdenum | 42 | 10.28 | 4.52 |
| Tungsten | 74 | 19.25 | 2.41 |

The majority of characteristic Cu K x-rays are generated within the penetration depth. The electron interactions below that depth typically generate few characteristic K-line x-rays but will contribute to the heat generation, thus resulting in a low thermal gradient along the depth direction. It is therefore preferable in some embodiments to set a maximum thickness for the microstructures in the target in order to limit electron interaction in the material and optimize local thermal gradients. One embodiment of the invention limits the depth of the micro structured x-ray generating material in the target to between one third and two thirds of the electron penetration depth in the substrate at the incident electron energy. In this case, the lower mass density of the substrate leads to a lower energy deposition rate in the substrate material immediately below the x-ray generating material, which in turn leads to a lower temperature in the substrate material below. This results in a higher thermal gradient between the x-ray generating material and the substrate, enhancing heat transfer. The thermal gradient is further enhanced by the high thermal conductivity of the substrate material.

For similar reasons, selecting the thickness of the microstructures to be less than one half of the electron penetration depth in the substrate is also generally preferred for efficient generation of bremsstrahlung radiation, because the electrons below that depth have lower energy and thus lower x-ray production efficiency.

Note: Other choices for the dimensions of the x-ray generating material may also be used. In targets as used in some embodiments of the invention, the depth of the x-ray material may be selected to be 50% of the electron penetration depth in the substrate. In other embodiments, the depth of the x-ray material may be selected to be 33% of the electron penetration depth in the substrate. In other embodiments, the depth for the microstructures may be selected related to the "continuous slowing down approximation" (CSDA) range for electrons in the material. Other depths may be specified depending on the x-ray spectrum desired and the properties of the selected x-ray material.

Figure 26A:
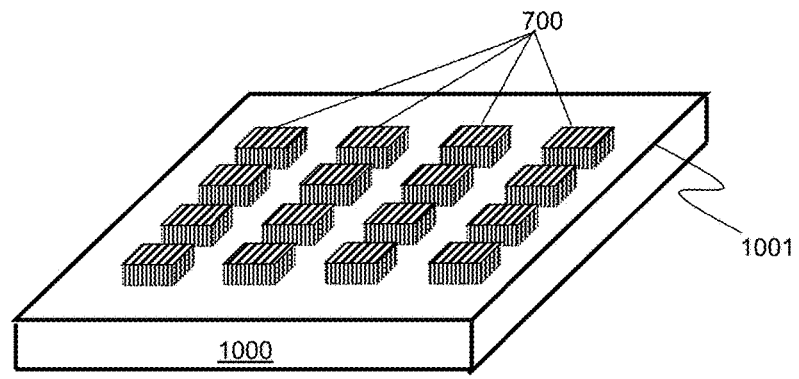
FIG. 26A illustrates a perspective view of a target comprising a grid of embedded rectangular target microstructures as used in some embodiments of the invention.
Figure 26B:
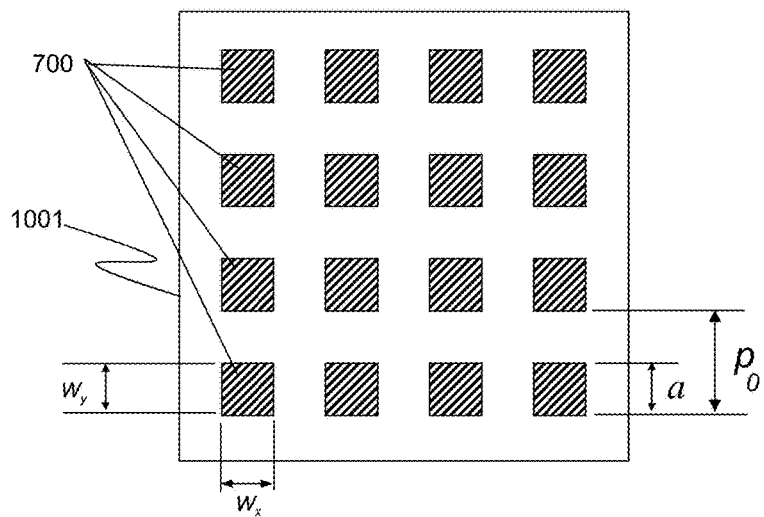
FIG. 26B illustrates a top view of the target of FIG. 26A.
Figure 26C:
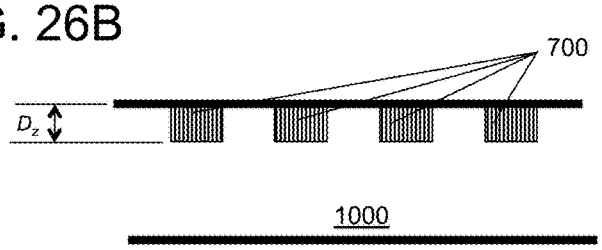
FIG. 26C illustrates a side/cross-section view of the target of FIGS. 26A and 26B.

FIG. 26 illustrates a region 1001 of a target as may be used in some embodiments of the invention that comprises an array of sub-sources 700 with microstructures in the form of right rectangular prisms comprising x-ray generating material arranged in a regular array. FIG. 26A presents a perspective view of the sixteen microstructures 700 for this target, while FIG. 26B illustrates a top down view of the same region, and FIG. 26C presents a side/cross-section view of the same region. (For the term "side/cross-section view" in this disclosure, the view meant is one as if a cross-section of the object had been made, and then viewed from the side towards the cross-sectioned surface. This shows both detail at the point of the cross-section as well as material deeper inside that might be seen from the side, assuming the substrate itself were transparent [which, in the case of diamond, is generally true for visible light].)

In these targets, the microstructures have been fabricated such that they are in close thermal contact on five of six sides with the substrate. As illustrated, the top of the microstructures 700 are flush with the surface of the substrate, but other targets in which the microstructure is recessed may be fabricated, and still other targets in which the microstructures present a topographical "bump" relative to the surface of the substrate may also be fabricated.

An alternative target as may be used in some embodiments of the invention may have several microstructures of right rectangular prisms simply deposited upon the surface of the substrate. In this case, only the bottom base of the prism would be in thermal contact with the substrate. For a structure comprising the microstructures embedded in the substrate with a side/cross-section view as shown in FIG. 26C with depth $D_z$ and lateral dimensions in the plane of the substrate of $W_x$ and $W_y$, the ratio of the total surface area in contact with the substrate for the embedded microstructures vs. deposited microstructures is $$\frac{A_{Embedded}}{A_{Deposited}} = 1 + 2D\frac{(W+L)}{(W \times L)} \quad [\text{Eqn. 13}]$$

With a small value for D relative to W and L, the ratio is essentially 1. For larger thicknesses, the ratio becomes larger, and for a cube (D=W=L) in which 5 equal sides are in thermal contact, the ratio is 5. If a cap layer of a material with similar properties as the substrate in terms of mass density and thermal conductivity is used, the ratio may be increased to 6.

Figure 27A:
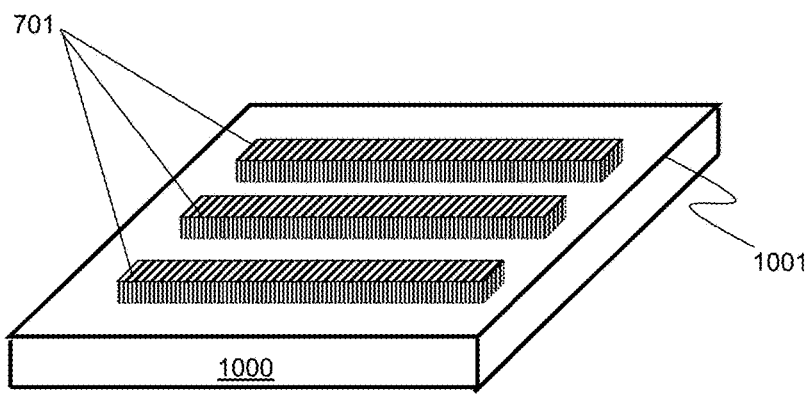
FIG. 27A illustrates a perspective view of a target comprising a set of embedded rectangular target microstructures forming a periodic linear pattern as used in some embodiments of the invention.
Figure 27B:
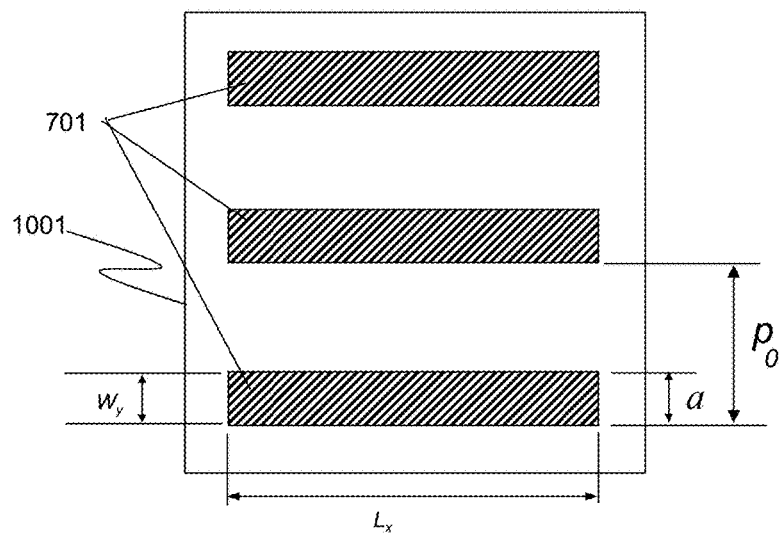
FIG. 27B illustrates a top view of the target of FIG. 27A.
Figure 27C:
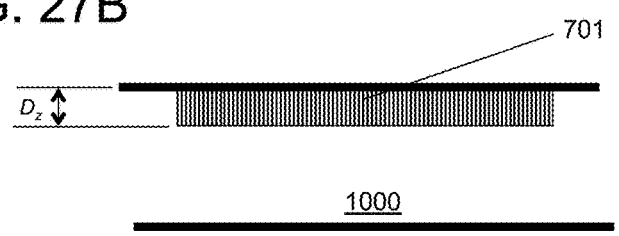
FIG. 27C illustrates a side/cross-section view of the target of FIGS. 27A and 27B.

FIG. 27 illustrates a region 1001 of a target as may be used in some embodiments of the invention, such as that previously illustrated in FIG. 13, that comprises an array of linear sub-sources 701 with microstructures in the form of right rectangular prisms comprising x-ray generating material arranged in a regular array. FIG. 27A presents a perspective view of the three microstructures 701 for this target, while FIG. 27B illustrates a top down view of the same region, and FIG. 27C presents a side/cross-section view of the same region.

In this embodiment, the lateral dimensions in the plane of the substrate are a width and length $W_x$ and $L_y$. The effective sub-source size a will correspond to the width $W_x$.

Figure 28:
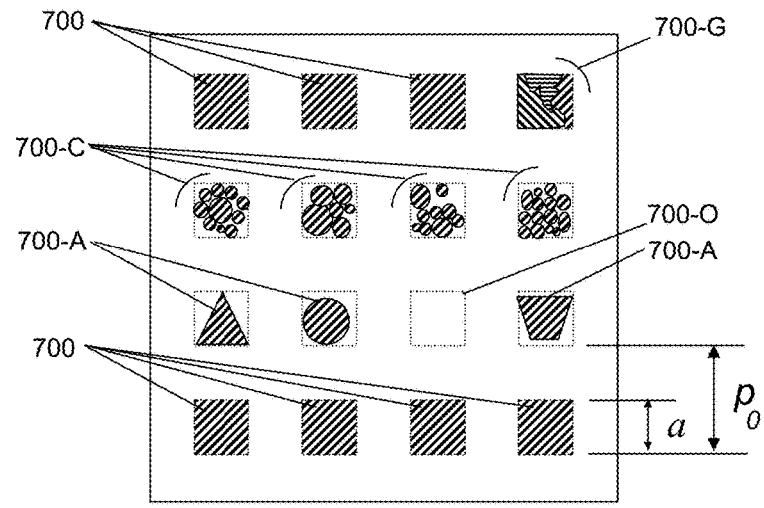
FIG. 28 illustrates variations in target structure for a target as shown in FIG. 26 that may arise from processing variations.
Figure 29:
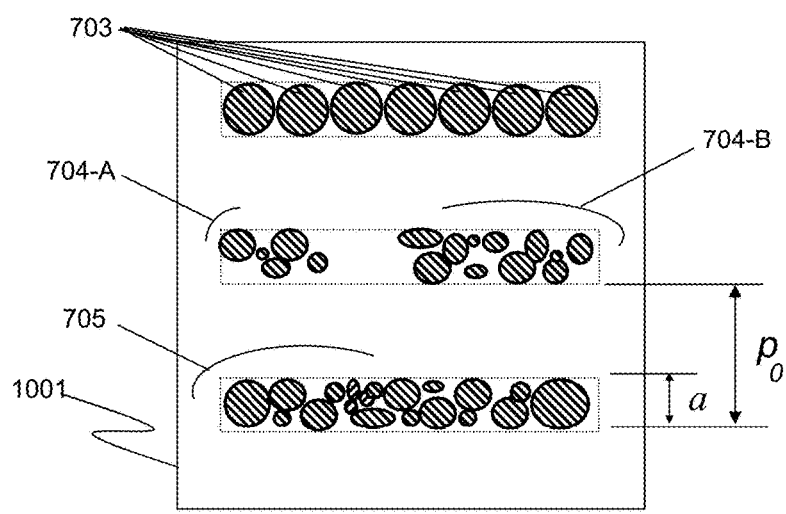
FIG. 29 illustrates variations in target structure for a target as shown in FIG. 27 that may arise from processing variations.

FIGS. 28 and 29 illustrate a practical issue that may arise in forming the targets such as those illustrated in FIGS. 26 and 27. FIG. 28 illustrates variations possible with the grid of x-ray generating microstructures 700 as illustrated in FIG. 26, and FIG. 29 illustrates variations possible with the linear x-ray generating microstructures 701 as illustrated in FIG. 27.

In FIG. 28, odd-shaped microstructures 700-A of other geometric shapes may be formed. Likewise, voids 700-O may also appear where certain structures may be expected. Other deposition processes, for example deposition using pre-formed particles of x-ray generating material may create ensemble clusters of particles 700-C that, when bombarded with electrons, may still act as x-ray sub-sources similar in function to those that are produced by a uniform structure. Also shown in FIG. 28 is a microstructure with multiple crystal structures and grain boundaries 700-G that again may still produce x-rays similar to those that are produced by a uniform structure, but may be considered to comprise an ensemble of microstructures.

The effective x-ray sub-source size in all of these situations may be approximated using the size parameter a, even though the microstructures comprise particles that are considerable smaller.

In FIG. 29 shows examples of ensemble microstructures as may occur when fabricating linear microstructures 701. If uniform pre-fabricated particles of x-ray generating material are created and coated onto the substrate, an ensemble of particles 703 of x-ray generating material may be formed. In other processes, if non-uniform particles are used, clusters of particles 704-A and 704-B may form, in some cases with a non-uniform distribution that may include gaps of voids. In other processes, an ensemble of particles 704 of x-ray generating material may approximate a line source of x-rays.

All of these ensembles, when bombarded with electrons, may still act as x-ray sub-sources similar in function to those that are produced by a uniform linear structure. The effective source size in these situations may be approximated using the size parameter a, even though the microstructures comprise particles that are considerable smaller.

Figure 30:
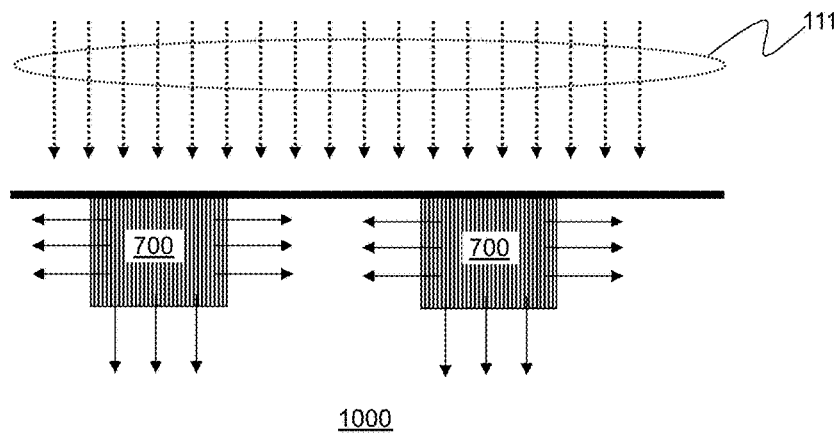
FIG. 30 illustrates a cross-section view of a portion of the target of FIG. 26, showing thermal transfer to a thermally conducting substrate under electron beam exposure according to the invention.

The heat transfer that may occur under electron bombardment is illustrated with representative arrows in FIG. 30, in which the heat generated in sub-sources 700 embedded in a substrate 1000 is conducted out of the microstructures comprising the sub-sources 700 through the bottom and sides (arrows for transfer through the sides out of the plane of the drawing are not shown). The amount of heat transferred per unit time (ΔQ) conducted through a material of area A and thickness d given by:

$$\Delta Q = \frac{\kappa \cdot A \cdot \Delta T}{d} \quad \text{[Eqn. 14]}$$

where κ is the thermal conductivity in W/(m °C.) and ΔT is the temperature difference across thickness d in °C. Therefore, an increase in surface area A, a decrease in thickness d and an increase in ΔT all lead to a proportional increase in heat transfer.

Figure 31:
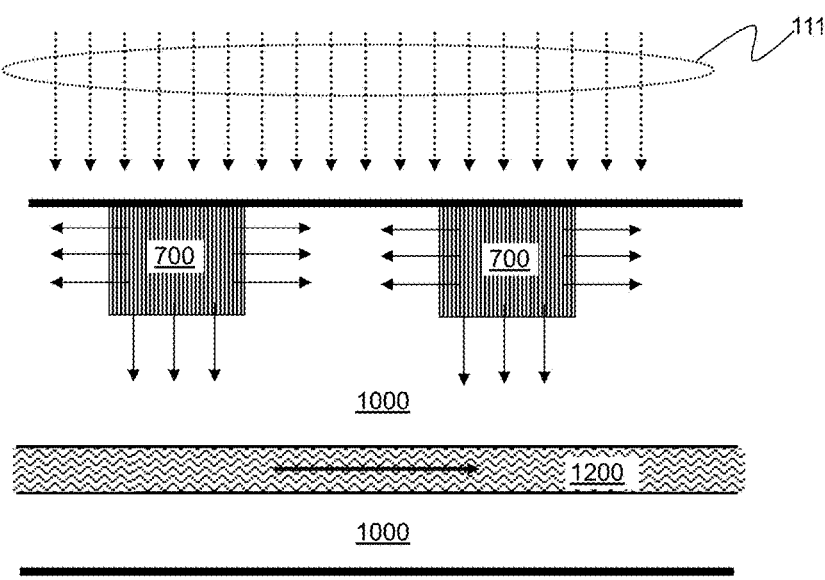
FIG. 31 illustrates a cross-section view of a variation of the target of FIGS. 26 and 30 comprising a substrate with a thermal cooling channel according to the invention.

An alternative embodiment is illustrated in FIG. 31, in which the substrate additionally comprises a cooling channel 1200. Such cooling channels may be a prior art cooling channel, as discussed above, using water or some other cooling fluid to conduct heat away from the substrate, or may be fabricated according to a design adapted to best remove heat from the regions near the embedded microstructures 700.

Other target structures for various embodiments may be understood or devised by those skilled in the art, in which the substrate may, for example, be bonded to a heat sink, such as a copper block, for improved thermal transfer. The copper block may in turn have cooling channels within it to assist in carrying heat away from the block. Alternatively, the substrate may be attached to a thermoelectric cooler, in which a voltage is applied to a specially constructed semiconductor device. In these devices, the flow of current causes one side to cool while the other heats up. Commercially available devices, such as Peltier coolers, can produce a temperature difference of up to 70° C. across the device, but may be limited in their overall capacity to remove large amounts of heat from a heat source. Heat pipes containing a heat transfer fluid that evaporates and condenses, as are used for cooling CPU chips in server farms when compact design is a consideration, may also be used to cool the substrate.

Alternatively, the substrate can be attached to a cryogenic cooler, such as a block containing channels for the flow of liquid nitrogen, or be in thermal contact with a reservoir of liquid nitrogen or some other cryogenic substance, such as an antifreeze solution, to provide more extreme cooling. When the substrate comprises a material such as diamond, sapphire, silicon, or silicon carbide, thermal conductivity generally increases with decreasing temperature from room temperature. In such a case, designing the target so that it can withstand cooling to these lower temperatures may be preferred.

Figure 32:
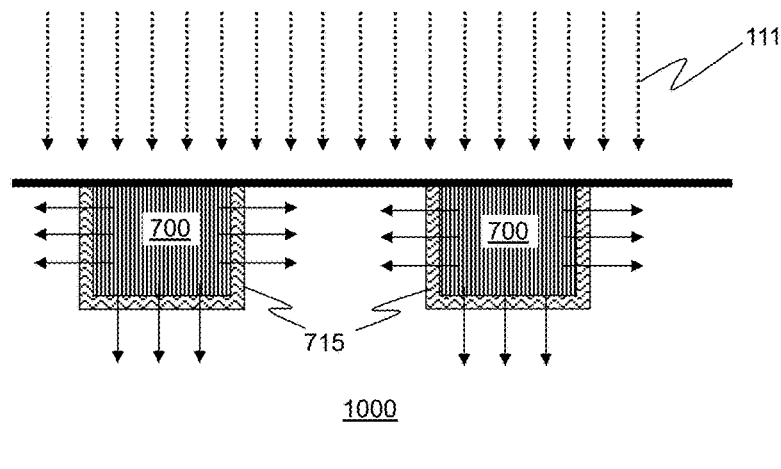
FIG. 32 illustrates a cross-section view of another variation of the target of FIG. 26 comprising an adhesion layer according to the invention.

FIG. 32 illustrates an alternative example of a target that may be used in embodiments of the invention in which the cavities formed in the substrate 1000 are first coated with an adhesion layer 715 (preferably of minimal thickness) before embedding the x-ray generating material that forms the microstructures 700. Such an adhesion layer may be appropriate in cases where the bond between the x-ray material and the substrate material is weak. The adhesion layer may also act as a buffer layer when the difference between thermal expansion coefficients for the two materials is large. For some choices of materials, the adhesion layer may be replaced or extended (by adding another layer) with a diffusion barrier layer to prevent the diffusion of material from the microstructures into the substrate material (or vice versa). For embodiments in which an adhesion and/or diffusion barrier layer is used, the selection of materials and thicknesses should consider the thermal properties of the layer as well, such that heat flow from the microstructures 700 to the substrate 1000 is not significantly impeded or insulated by the presence of the adhesion layer 715.

Figure 33:
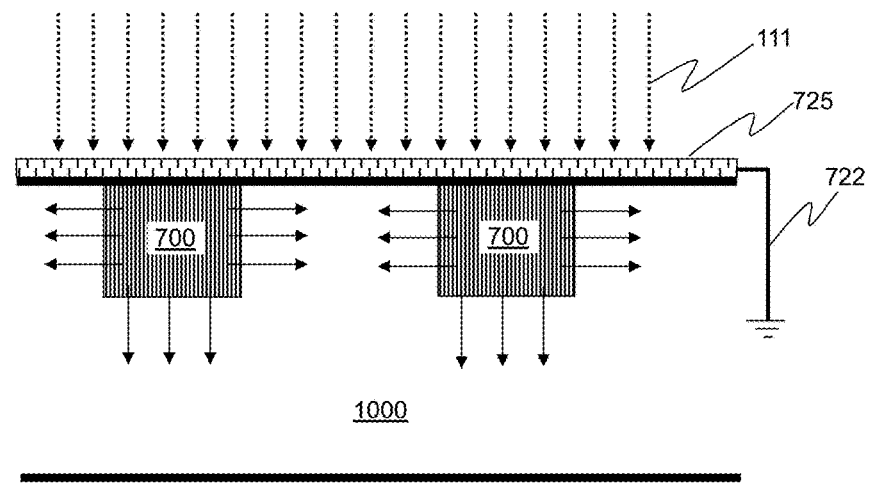
FIG. 33 illustrates a cross-section view of another variation of the target of FIG. 26 comprising an electrically conducting overcoat according to the invention.

FIG. 33 illustrates an alternative example of a target that may be used in embodiment in which an electrically conducting layer 725 has been added to the surface of the target. When bombarded by electrons, the excess charge needs a path to return to ground for the target to function effectively as an anode. If the target as illustrated in FIG. 26 were to comprise only discrete, unconnected microstructures 700 within an electrically insulating substrate material (such as undoped diamond), under continued electron bombardment, significant charge would build up on the surface. The electrons from the cathode would then not collide with the target with the same energy, or might even be repelled, diminishing the generation of x-rays.

This can be addressed by the deposition of a thin layer of conducting material that is preferably of relatively low atomic number, such as aluminum (Al), beryllium (Be), carbon (C), chromium (Cr) or titanium (Ti), that allows electrical conduction from the discrete microstructures 700 to an electrical path 722 that connects to a positive terminal relative to the high voltage supply. This terminal as a practical matter is typically the electrical ground of the system, while the cathode electron source is supplied with a negative high voltage.

Figure 34:
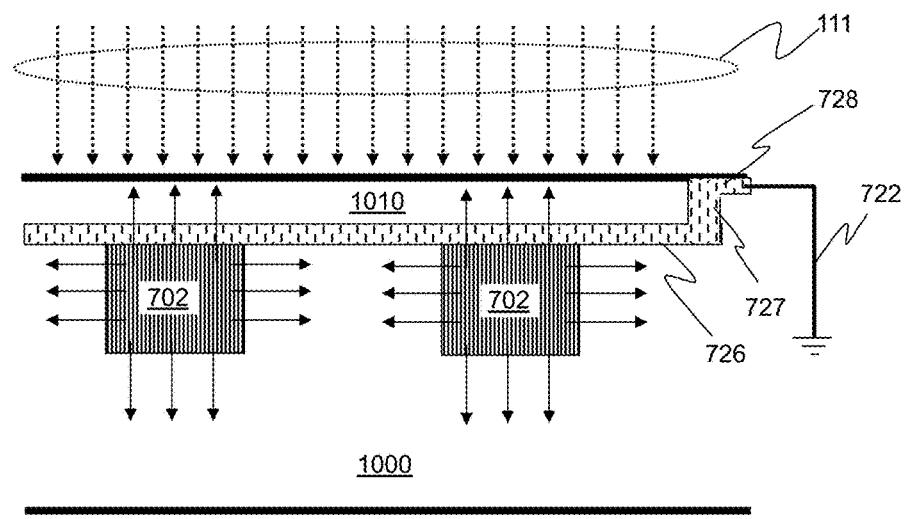
FIG. 34 illustrates a cross-section view of another variation of the target of FIG. 26 comprising buried x-ray material according to the invention.

FIG. 34 illustrates another example of a target that may be used in embodiment of the invention, in which the sub-sources 702 are embedded deeper, or buried, into the substrate 1000. Such an embedded microstructure may be further covered by the deposition of an additional layer 1010, which may be, for example, diamond, providing the same heat transfer properties as the substrate. This allows heat to be conducted away from all sides of the buried sub-source 702. For such a situation and when the additional layer 1010 does not have sufficient electrical conductivity, it is advisable to provide a path 722 to ground for the electrons incident on the structure, which may be in the form of a embedded conducting layer 726 laid down before the deposition of the additional layer 1010. In some embodiments, this conducting layer 726 will have a "via" 727, or a vertical connection, often in the form of a pillar or cylinder, that provides an electrically conducting structure to link the embedded conducting layer 726 to an additional conducting layer 728 on the surface of the target, which in turn is connected to the path 722 to ground, or the high voltage supply.

Figure 35:
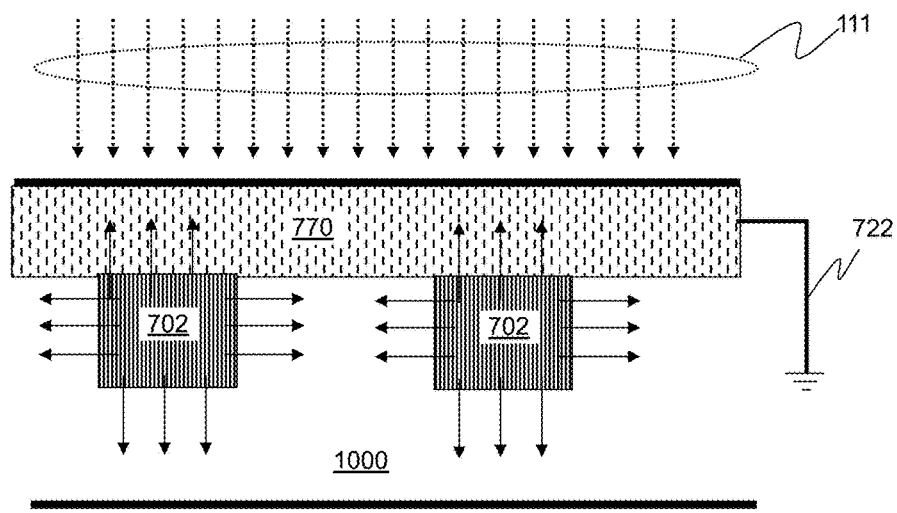
FIG. 35 illustrates a cross-section view of another variation of the target of FIG. 26 comprising buried x-ray material and a thick thermally and electrically conducting overcoat according to the invention.

FIG. 35 illustrates another example of a target that may be used in embodiments of the invention, in which the sub-sources 702 are again buried within the substrate. However, in this embodiment, instead of first providing an electrically conducting layer followed by the deposition of an additional cap layer, in this embodiment only a single layer 770 is deposited, selected for a combination of electrical properties and thermally conducting properties. This may be, for example, a deposition of carbon nanotubes (Z=6) oriented vertically relative to the surface, such that they conduct both heat and electrons away from the buried microstructures 702. This single layer 770 may in turn be connected to a path 722 to ground to allow the target to serve as an anode in the x-ray generation system. Alternatively, the material of the layer 770 may be selected to comprise aluminum (Al), beryllium (Be), chromium (Cr), or copper (Cu).

Figure 36:
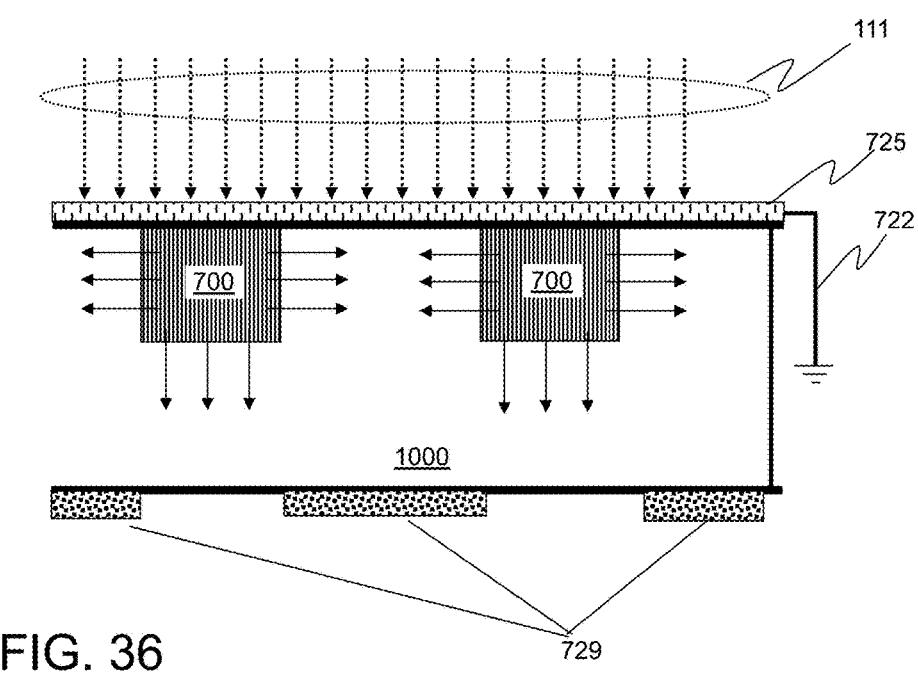
FIG. 36 illustrates a cross-section view of another variation of the target of FIG. 26 comprising an additional blocking structures on the back surface of the substrate, to block the transmission of x-rays produced by the substrate.
Figure 37:
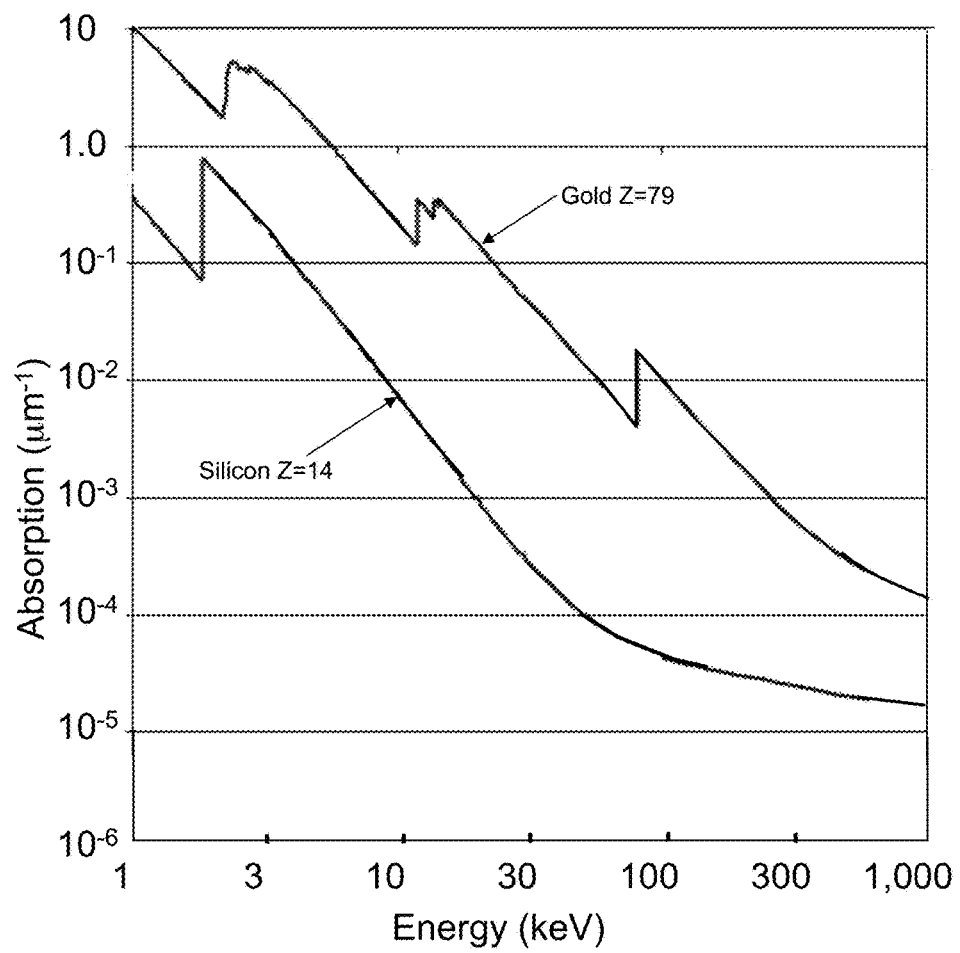
FIG. 37 illustrates a plot of the x-ray absorption of gold and silicon as a function of x-ray energy.

FIG. 36 illustrates another variation of an embodiment, in which an additional patterns of blocking material 729 have been deposited on the backside of the target substrate 1000. If the figure of merit for the selected material combination, as discussed above in Table II, is not large, there may still be significant x-rays generated by the substrate that will reduce contrast in the image. These substrate-generated x-rays can be blocked by a deposition of a suitable material, such as gold, as blocking structures 729. Gold (Z=79) has a strong x-ray absorption, as illustrated in FIG. 37. Processes to deposit these blocking structures may comprise standard deposition processes, and an alignment step may be needed to ensure alignment with the x-ray generating structures on the opposite side.

It should be clear to those skilled in the art that although several embodiments have been presented separately in FIGS. 24-36, and various processes for their manufacture will be presented later, the elements of these embodiments may be combined with each other, or combined with other commonly known target fabrication methods known in the art. For example, the buried sub-sources 702 of FIG. 35 may also comprise multiple grains of microstructures, as was illustrated in FIGS. 28 and 29. Likewise, the adhesion layer 715 as illustrated in FIG. 32 may also be applied to fabrication of embedded sub-sources 700 as shown in FIG. 33. The separation of these alternatives is for illustration only, and is not meant to be limiting for any particular process.

Although the sub-sources illustrated in FIGS. 24-36 have been shown as regularly spaced patterns with uniform size and shape, a regular pattern of sub-sources having non-uniform size and shape, can also be used in some embodiments of the invention. Additionally, each sub-source within a regular periodic pattern may further be comprised of multiple smaller microstructures of non-uniform sizes and shapes. These smaller microstructures may be non-regular and do not necessarily need to have similar x-ray emission characteristics or strength, so as long as the larger sub-sources that each group of microstructures comprise are periodic in nature.

Likewise, although some embodiments have been described with microstructures in, for example, the shape of right rectangular prisms, fabrication processes may create structures that have walls at angles other than 90°, or do not have corners that are exactly right angles, but may be rounded or beveled or undercut, depending on the artifacts of the specific process used. Embodiments in which the microstructures are essentially similar with the shapes described herein will be understood by those skilled in the art to be disclosed, even if process artifacts lead to some deviation from the shapes as illustrated or described.

In other embodiments of the system, a periodic attenuating grating $G_0$ such as are used in the prior art Talbot-Lau interferometers may also be used in conjunction with the source of the invention, so that the x-rays produced by the substrate material surrounding the sub-sources are further attenuated, allowing greater monochromaticity and therefore higher spatial coherence for the source. The apertures of the grating should be coincident with projections of the microstructured x-ray sub-sources, or may, in some embodiments, be placed at a Talbot fractional or integer distance downstream of the source and with the apertures coincident with the source self-images. It is preferable that the grating $G_0$ is of high atomic number and relatively low aspect ratio, for ease of manufacturability.

3. Fabrication of Gratings

Fabrication of the gratings used in embodiments of the invention may be made using known prior art fabrication processes such as those previously described by Christian David [C. David et al., "Fabrication of diffraction gratings for hard x-ray phase contrast imaging", *Microelectron. Eng.* 84, 1172-1177, 2007].

Gratings for x-rays may be fabricated using silicon substrates, with etched changes in topography to induce phase changes and depositions of a higher Z material, such as gold (Au, Z=79), to induce absorption changes. The x-ray absorption properties for gold and silicon are illustrated in FIG. 37.

Figure 38:
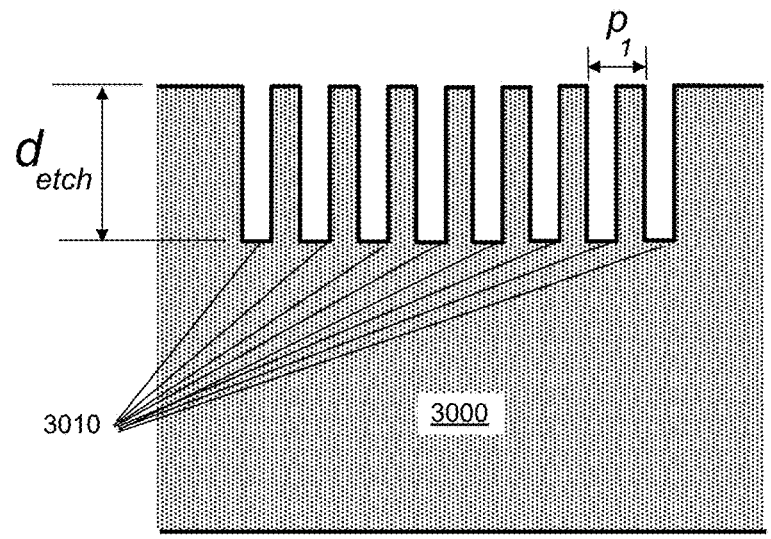
FIG. 38 illustrates a possible structure of an x-ray phase grating according to some embodiments of the invention.

As shown in FIG. 38, a periodic pattern 3010 may be etched into a silicon substrate 3000 to create a structure which introduces a periodic phase shift for x-rays falling at normal incidence. The phase shift depends on the etch depth, with a phase-shift of z radians for normal incidence x-rays achieved when the following condition is met:

$$d_{etch} = \frac{1}{2}\frac{\lambda}{|n-1|} = \frac{1}{2}\frac{\lambda}{\delta} \qquad [\text{Eqn. 15}]$$

Values for $\delta$ for silicon at several x-ray energies, along with the depth etched structures need to a phase-shift of $\pi$ radians are shown in Table IV.

TABLE IV

Etch depth for Silicon phase shift of $\pi$ radians.

| X-ray Energy (keV) | Wavelength $\lambda$ (nm) | $\delta$ | $\pi$ phase shift depth (μm) |
|---|---|---|---|
| 3.0 | 0.413 | 5.43E−05 | 3.81 |
| 5.0 | 0.248 | 1.98E−05 | 6.26 |
| 8.048 (Cu Kα) | 0.154 | 7.58E−06 | 10.17 |
| 10.0 | 0.124 | 4.89E−06 | 12.69 |
| 17.48 (Mo Kα) | 0.0709 | 1.59E−06 | 22.36 |
| 30.0 | 0.0413 | 5.36E−07 | 38.52 |
| 50.0 | 0.0248 | 1.93E−07 | 64.31 |
| 59.39 (W Kα) | 0.0209 | 1.37E−07 | 76.32 |
| 100.0 | 0.0124 | 4.82E−08 | 128.74 |

A typical grating fabrication process comprises coating a <110> oriented silicon wafer with a photoresist, and patterning the resist using conventional photolithography or electron beam lithography. The silicon then undergoes an etching process such as wet etching in, for example, a potassium hydroxide (KOH) solution, or reactive ion etching (RIE), with the etching selectively occurring only for portions of the silicon not masked by the resist. The etch depth may be controlled by adjusting the time of the etch process. Other variations of the etching process will be known those skilled in the art of semiconductor processing and manufacturing.

Figure 39:
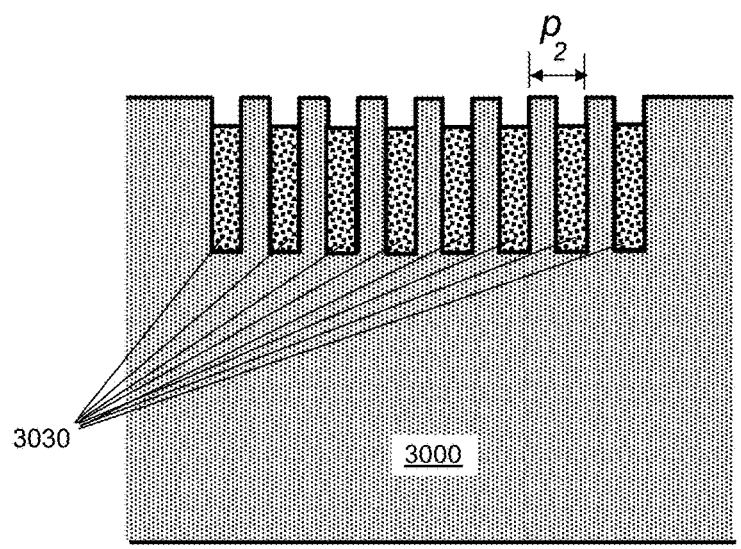
FIG. 39 illustrates a possible structure of an x-ray absorption grating according to some embodiments of the invention.

Absorption gratings such as those used for $G_2$ may be fabricated by initially crating a silicon phase grating, as described above, and then depositing an x-ray absorbing material, such as gold, into the grooves already patterned in the silicon. This is illustrated in FIG. 39, in which an amount of x-ray absorbing material 3030 such as gold has filled the grooves created in a silicon substrate 3000. One process for the deposition of gold into the silicon grooves involves a standard electroplating processes. To ensure that gold is only deposited into the grooves, a sacrificial layer of aluminum may initially deposited at an angle, and a seed layer ~50 nm thick comprising Chromium (Cr) and gold (Au) are then deposited. A phosphoric acid treatment removes the all the material deposited on the tops of the silicon structures, leaving seed material only in the bottom of the grooves in the silicon. Standard electroplating may follow, with growth of gold occurring only onto the deposited seed layers. Deposition of 10 to 20 mm of gold can create absorption gratings with a transmission modulation of 75% or more. Absorption will, however, depend on the x-ray energy and the absorption coefficient for the material, as was illustrated in FIGS. 1 and 37. Other methods for making x-ray absorption gratings will be known to those skilled in the art.

For some applications and for certain x-ray wavelengths, crystal gratings may also be used.

4.0 Detector Properties

The detector may be any one of a number of detectors used to form x-ray images. One type of commonly used x-ray detector comprises a fluorescent screen or scintillator, such as one comprising a layer of cesium iodide (CsI), thallium doped CsI, yttrium aluminium garnet (YAG) or gadolinium sulfoxylate (GOS), that emits visible photons when exposed to x-rays. The visible photons are then detected by an electronic sensor that converts visible intensity into electronic signals, often with the additional formation of a relay image using visible optics that enlarge and magnify the intensity pattern of the photons emitted by the fluorescent screen. With the relay optics, the electronic detector need not comprise a high resolution sensor itself, and inexpensive commercial CCD detectors or complementary metal-oxide-semiconductor (CMOS) sensor arrays with, for example, 1024×1024 pixels, each 24 μm×24 μm square, may be used.

Commercial flat panel digital x-ray sensors in which a layer of scintillator material is placed in close proximity to (or even coated onto) an array of conventional optical image sensors are manufactured by, for example, Varian Inc. of Palo Alto, Calif. and General Electric, Inc. of Billerica, Mass. Other configurations of image sensors may be known to those skilled in the art. In embodiments in which a G2 analyzer grating is used, it is preferable to use highly efficient, fast read-out detectors such as flat panel detectors, used for medical and industrial uses. For many applications, a flat panel detector with a resolution larger than 20 microns will require that an analyzer grating $G_2$ with a period equal to the Talbot fringe period to be placed in the x-ray beam path before the detector.

A second approach is to use an electronic sensor that directly creates an electrical signal in response to the absorption of x-rays, by, for example, the creation of direct electron-hole pairs in amorphous selenium (a-Se). These are then converted into electronic signals using an array of thin-film transistors (TFTs). Such direct flat panel detectors (FPDs) such as the Safire FPD of Shimadzu Corp. of Kyoto, Japan, are commercially available.

5.0 Variations

Embodiments may further comprise other components typically included in Talbot interferometer, including spectral filters to obtain a desired x-ray energy bandwidth and positioning control systems for all the various components of the system.

With this application, several embodiments of the invention, including the best mode contemplated by the inventors, have been disclosed. It will be recognized that, while specific embodiments may be presented, elements discussed in detail only for some embodiments may also be applied to others.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:

1. An x-ray interferometric imaging system comprising:
a source of x-rays comprising:
  a vacuum chamber;
  an electron beam emitter; and
  a target comprising:
    a substrate comprising a first material; and
    a plurality of discrete structures embedded in the substrate, the plurality of discrete structures comprising a second material that generates x-rays in response to electron irradiation, said plurality of discrete structures arranged in a periodic pattern to produce a periodic pattern of sub-sources of x-rays when irradiated by electrons from the electron beam emitter;
a beam-splitting x-ray grating comprising periodic structures that introduce a phase shift for a predetermined x-ray wavelength, the periodic structures comprising two-dimensional structures arranged in a checkerboard pattern, said beam-splitting x-ray grating positioned to diffract x-rays generated by the periodic pattern of sub-sources of x-rays;
a stage configured to hold an object to be imaged; and
an x-ray detector comprising a two-dimensional array of x-ray detecting elements, said object positioned between the beam-splitting x-ray grating and the x-ray detector, said x-ray detector positioned to detect the x-rays diffracted by the beam-splitting x-ray grating and perturbed by the object to be imaged.

2. The x-ray interferometric imaging system of claim 1, in which a ratio $(Z_2 \rho_2)/(Z_1 \rho_1)$ for the second material and the first material is greater than 12, where $Z_1$ and $\rho_1$ are the atomic number and the mass density, respectively, of the first material and $Z_2$ and $\rho_2$ are the atomic number and the mass density, respectively of the second material.

3. The x-ray interferometric imaging system of claim 1, in which the first material is selected from the group consisting of: beryllium, diamond, graphite, silicon, boron nitride, silicon carbide, sapphire and diamond-like carbon.

4. The x-ray interferometric imaging system of claim 1, in which the plurality of discrete structures have similar shapes.

5. The x-ray interferometric imaging system of claim 1, in which the periodic pattern of the plurality of discrete structures is a regular grid and a width in at least one dimension of one or more discrete structures of the plurality of discrete structures is less than 10 microns.

6. The x-ray interferometric imaging system of claim 1, in which the periodic pattern of the plurality of discrete structures is a set of parallel lines and a width in one dimension of one or more discrete structures of the plurality of discrete structures is less than 10 microns, and a length in a perpendicular dimension is greater than 20 microns.

7. The x-ray interferometric imaging system of claim 1, in which the phase shift of the beam-splitting x-ray grating is approximately $\pi$ radians for the predetermined x-ray wavelength.

8. The x-ray interferometric imaging system of claim 1, in which the phase shift of the beam-splitting x-ray grating is approximately $\pi/2$ radians for the predetermined x-ray wavelength.

9. The x-ray interferometer imaging system of claim 1, in which the x-ray detector is positioned at a distance from the beam-splitting x-ray grating that corresponds to an odd multiple of $1/16^{th}$ of a Talbot Distance for the beam-splitting x-ray grating when used with spherical wave x-rays of a predetermined wavelength spectrum and spatial coherence, the x-ray detector having a spatial resolution at least three times a Talbot fringe period for a Talbot interference pattern at said odd multiple of $1/16^{th}$ of the Talbot Distance for the beam-splitting x-ray grating when used with x-rays of said predetermined wavelength spectrum and spatial coherence.

10. The x-ray interferometric imaging system of claim 1, in which an orientation of at least two discrete structures of the plurality of discrete structures of the target are such that, when simultaneously bombarded by electrons from the electron beam emitter, the x-rays generated by a first discrete structure of the at least two discrete structures overlap in part the x-rays generated by a second discrete structure of the at least two discrete structures, and the overlapping x-rays propagate together towards the beam-splitting x-ray grating.

11. The x-ray interferometric imaging system of claim 1, wherein the stage is configured to adjust a position of the object relative to the beam-splitting x-ray grating.

12. The x-ray interferometric imaging system of claim 11, wherein the stage is configured to move the object along each of three orthogonal axes and to rotate the object along each of three orthogonal axes.

13. The x-ray interferometric imaging system of claim 1, additionally comprising: an analyzer grating placed in close proximity to a surface of the x-ray detector.

14. The x-ray interferometric imaging system of claim 13, in which the analyzer grating comprises periodic structures that form an x-ray absorption grating, in which the periodic structures of the analyzer grating have a period $p_2$ given approximately by:

$$p_2 = p_0 \frac{D}{L}$$

where $p_0$ is the period of the periodic pattern of sub-sources of x-rays, D is the distance between the beam-splitting x-ray grating and the analyzer grating, and L is the distance between the target and the beam-splitting x-ray grating.

15. The x-ray interferometric imaging system of claim 13, wherein the stage is configured to adjust a position of the object relative to the analyzer grating.

16. The x-ray interferometric imaging system of claim 1, additionally comprising:
a cooling system comprising:
a reservoir for storing a cooling fluid;
a channel within the substrate for conducting the cooling fluid;
an additional channel to conduct the cooling fluid from the reservoir to the channel within the substrate;
an additional channel to conduct the cooling fluid from the channel within the substrate to the reservoir; and
a pumping mechanism to pump the cooling fluid through the cooling system.

17. An x-ray tomography system comprising:
an x-ray source comprising:
a vacuum chamber;
an electron beam emitter; and
a target comprising:
a substrate comprising a first material; and
a plurality of discrete structures embedded in the substrate, the plurality of discrete structures comprising a second material that generates x-rays in response to electron irradiation, said plurality of discrete structures arranged in a periodic pattern to produce a periodic pattern of sub-sources of x-rays when irradiated by electrons from the electron beam emitter;
a beam-splitting x-ray grating comprising periodic structures that introduce a phase shift for a predetermined x-ray wavelength, the periodic structures comprising two-dimensional structures arranged in a checkerboard pattern, said beam-splitting x-ray grating positioned to diffract x-rays generated by the periodic pattern of sub-sources of x-rays;
a stage configured to hold an object for tomographic data collection; and
an x-ray detector comprising a two-dimensional array of x-ray detecting elements, said object positioned between the beam-splitting x-ray grating and the x-ray detector, said x-ray detector positioned to detect the x-rays diffracted by the beam-splitting x-ray grating and perturbed by the object to be imaged.

18. The x-ray tomography system of claim 17, wherein the stage is configured to controllably change a position and an orientation of the object relative to the x-ray source.

19. The x-ray tomography system of claim 18, in which the stage is configured to controllably change an angle of incidence of the x-rays on the object.

20. The x-ray tomography system of claim 19, in which the stage and the x-ray detector are configured to make a plurality of images of the object in which each of the plurality of, images is collected using a different setting for the angle of incidence of the x-rays on the object.

21. An x-ray interferometric imaging system comprising:
a source of x-rays comprising:
a vacuum chamber;
an electron beam emitter; and
a target comprising:
a substrate comprising a first material; and
a plurality of discrete structures embedded in the substrate, the plurality of discrete structures comprising a second material that generates x-rays in response to electron irradiation, said plurality of discrete structures arranged in a periodic pattern to produce a periodic pattern of sub-sources of x-rays when irradiated by electrons from the electron beam emitter;

a beam-splitting x-ray grating comprising periodic structures that introduce a phase shift for a predetermined x-ray wavelength, said beam-splitting x-ray grating positioned to diffract x-rays generated by the periodic pattern of sub-sources of x-rays;

a stage configured to hold an object to be imaged; and an x-ray detector comprising a two-dimensional array of x-ray detecting elements, said object positioned between the beam-splitting x-ray grating and the x-ray detector, said x-ray detector configured to detect the x-rays diffracted by the beam-splitting x-ray grating and perturbed by the object to be imaged, the x-ray detector positioned at a distance from the beam-splitting x-ray grating that corresponds to an odd multiple of $1/16^{th}$ of a Talbot Distance for the beam-splitting x-ray grating when used with spherical wave x-rays of a predetermined wavelength spectrum and spatial coherence, the x-ray detector having a spatial resolution at least three times a Talbot fringe period for a Talbot interference pattern at said odd multiple of $1/16^{th}$ of the Talbot Distance for the beam-splitting x-ray grating when used with x-rays of said predetermined wavelength spectrum and spatial coherence.

22. An x-ray interferometric imaging system comprising:
a source of x-rays comprising:
  a vacuum chamber;
  an electron beam emitter; and
  a target comprising:
    a substrate comprising a first material; and
    a plurality of discrete structures embedded in the substrate, the plurality of discrete structures comprising a second material that generates x-rays in response to electron irradiation, said plurality of discrete structures arranged in a periodic pattern to produce a periodic pattern of sub-sources of x-rays when irradiated by electrons from the electron beam emitter;

a beam-splitting x-ray grating comprising periodic structures that introduce a phase shift for a predetermined x-ray wavelength, said beam-splitting x-ray grating positioned to diffract x-rays generated by the periodic pattern of sub-sources of x-rays;

a stage configured to hold an object to be imaged, the stage configured to adjust a position of the object relative to the beam-splitting x-ray grating by translating the object along each of three orthogonal axes and rotating the object along each of three orthogonal axes; and an x-ray detector comprising a two-dimensional array of x-ray detecting elements, said object positioned between the beam-splitting x-ray grating and the x-ray detector, said x-ray detector positioned to detect the x-rays diffracted by the beam-splitting x-ray grating and perturbed by the object to be imaged.

* * * * *

UNITED STATES PATENT AND TRADEMARK OFFICE
CERTIFICATE OF CORRECTION

PATENT NO. : 10,349,908 B2
APPLICATION NO. : 14/943445
DATED : July 16, 2019
INVENTOR(S) : Wenbing Yun et al.

It is certified that error appears in the above-identified patent and that said Letters Patent is hereby corrected as shown below:

In the Specification

In Column 26, Line 40, delete "z" and insert --$\pi$--.

Signed and Sealed this
Thirty-first Day of December, 2019

Andrei Iancu
*Director of the United States Patent and Trademark Office*